US012385051B2

United States Patent
Venkatesan et al.

(10) Patent No.: US 12,385,051 B2
(45) Date of Patent: Aug. 12, 2025

(54) SHIGELLA-BASED MINIMAL PLASMID RECOMBINANT INVASION CONSTRUCT

(71) Applicant: THE GOVERNMENT OF THE UNITED STATES AS REPRESENTED BY THE SECRETARY OF THE ARMY, Fort Detrick, MD (US)

(72) Inventors: Malabi M. Venkatesan, Bethesda, MD (US); Lakshmi Chandrasekaran, Gaithersburg, MD (US); Akamol E. Suvarnapunya, Rockville, MD (US)

(73) Assignee: THE GOVERNMENT OF THE UNITED STATES AS REPRESENTED BY THE SECRETARY OF THE ARMY, Fort Detrick, MD (US)

( * ) Notice: Subject to any disclaimer, the term of this patent is extended or adjusted under 35 U.S.C. 154(b) by 471 days.

(21) Appl. No.: 17/923,853

(22) PCT Filed: May 5, 2021

(86) PCT No.: PCT/US2021/030882
§ 371 (c)(1),
(2) Date: Nov. 7, 2022

(87) PCT Pub. No.: WO2021/236327
PCT Pub. Date: Nov. 25, 2021

(65) Prior Publication Data
US 2023/0183719 A1    Jun. 15, 2023

Related U.S. Application Data

(60) Provisional application No. 63/021,463, filed on May 7, 2020.

(51) Int. Cl.
| | | |
|---|---|---|
| C12Q 1/68 | (2018.01) | |
| C12N 15/00 | (2006.01) | |
| C12N 15/70 | (2006.01) | |
| C12N 15/74 | (2006.01) | |

(52) U.S. Cl.
CPC .............. *C12N 15/74* (2013.01); *C12N 15/70* (2013.01)

(58) Field of Classification Search
None
See application file for complete search history.

(56) References Cited

U.S. PATENT DOCUMENTS 9,434,772 B2    9/2016   Maurelli

FOREIGN PATENT DOCUMENTS

WO    20210236327 A2    11/2021

OTHER PUBLICATIONS

PCT/US2021/030882, PCT Search Report & Written Opinion mailed Feb. 2, 2022, 10 pages.
Coster, Trinka S. et al., "Vaccination against Shigellosis with Attenuated Shigella flexneri 2a Strain SC602", Infection and Immunity, Jul. 1999, vol. 67, No. 7, pp. 3437-3443.
GenBank CP050984.1, Shigella flexneri strain FDAARGOS_716 plasmid unnamed1, complete sequence, downloaded from Internet Jan. 7, 2022, 15 pages.
Kotloff, Karen L. et al., "Shigella flexneri 2a Strain CVD 1207, with Specific Deletions in virG, sen, set, and guaBA, Is Highly Attenuated in Humans", Infection and Immunity, Mar. 2000, vol. 68, No. 3, pp. 1034-1039.
Levine, Myron M. et al., Clinical trials of Shigella vaccines: two steps forward and one step back on a long, hard road, Nature, July 1007, vol. 5, pp. 540-553.
Maurelli, Anthony T. et al., "Temperature-Dependent Expression of Virulence Genes in *Shigella* Species", Infection and Immunity, Jan. 1984, vol. 43, No. 1, pp. 195-201.
Venkatesan, Malabi M. et al., "Use of Shigella flexneri ipaC and ipaH Gene Sequences for the General Identification of *Shigella* spp. and Enteroinvasive *Escherichia coli*", Journal of Clinical Microbiology, Dec. 1989, vol. 27, No. 12, pp. 2687-2691.
Yang, Fan et al., "Genome dynamics and delivery of *Shigella* species, the etiologic agents of bacillary dysentery", Nucleic Acids Research, 2005, vol. 33, No. 19, pp. 6445-6458.
EESR mailed Jun. 6, 2024, 8 pages.
Bliven, Kimberly A. "Pathoadaption of the intracellular bacteria Shigella and Chalmydia: Virulence, antivirulence, and tissue tropism", 2015, XP093159307.

*Primary Examiner* — Jennifer E Graser
(74) *Attorney, Agent, or Firm* — Timothy H. Van Dyke; Wolter Van Dyke Davis, Pllc

(57) ABSTRACT

Recombinant *Shigella* minimal invasion plasmid constructs pRISM and pRISM-G and a method of inducing an immune response to *Shigella* in a subject, the method comprising administering the composition to the subject in an amount sufficient to induce an immune response to *Shigella* in the subject.

12 Claims, 10 Drawing Sheets

Figure 1:
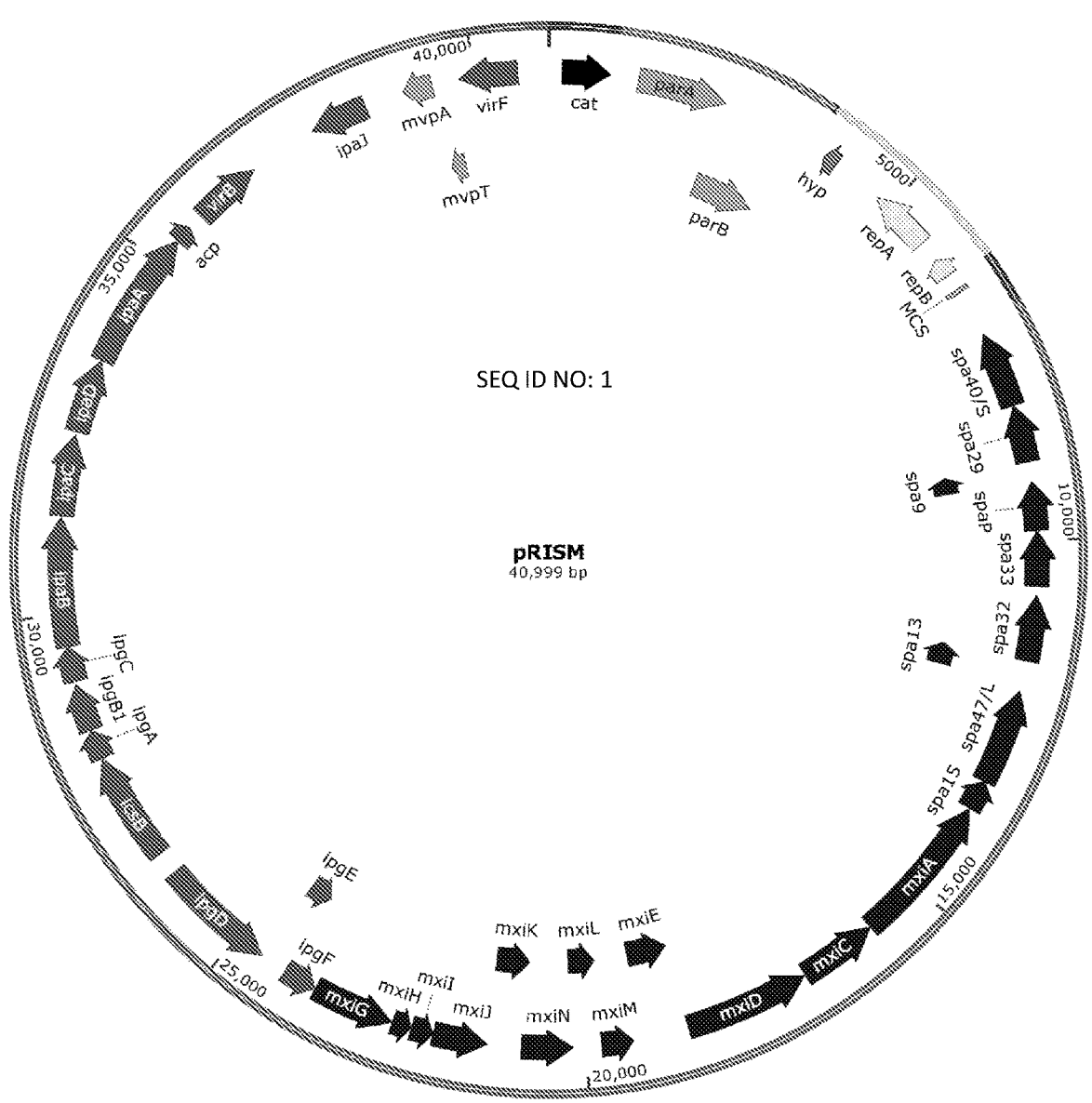
Figure 2:
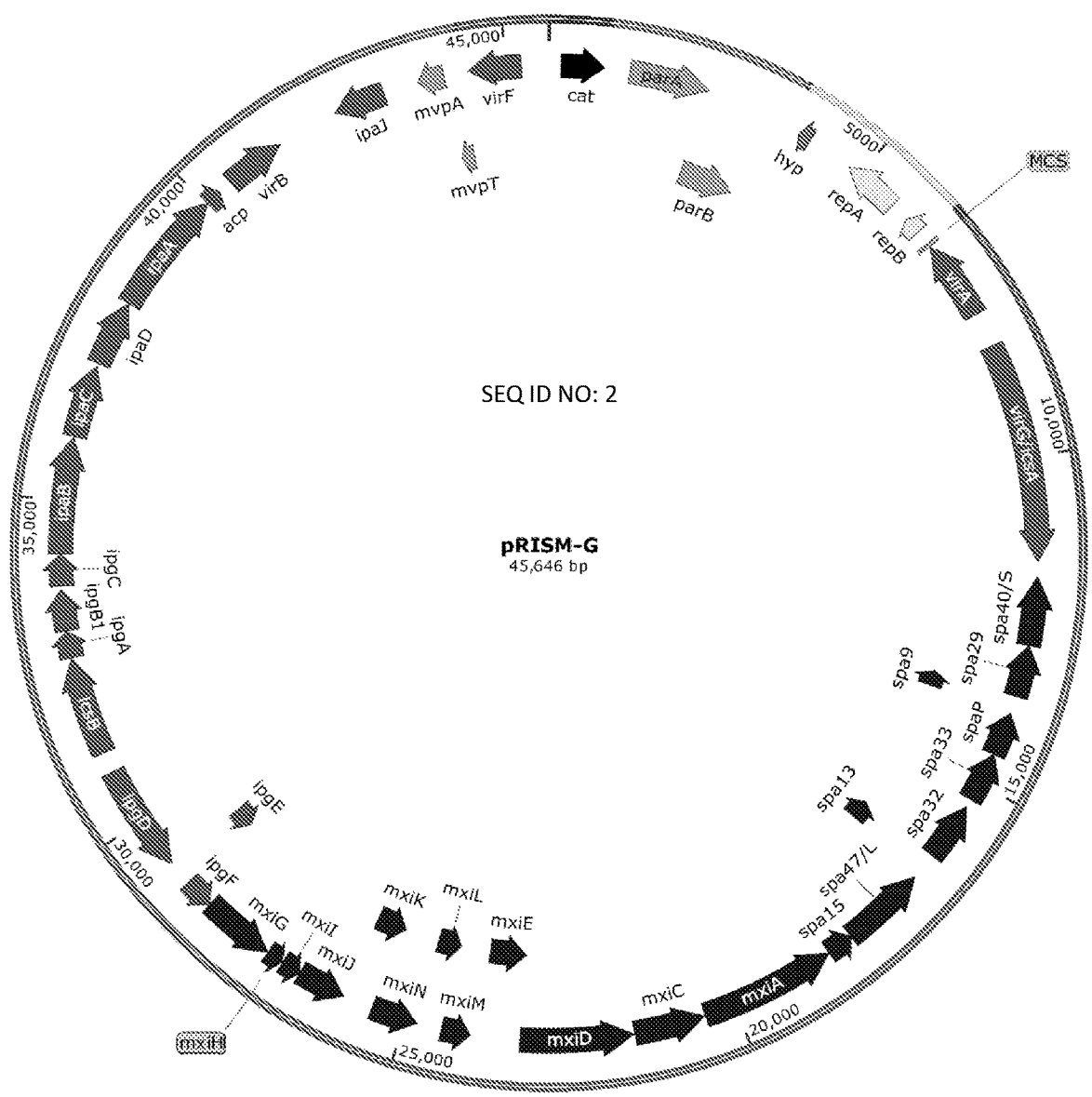
Figure 3:
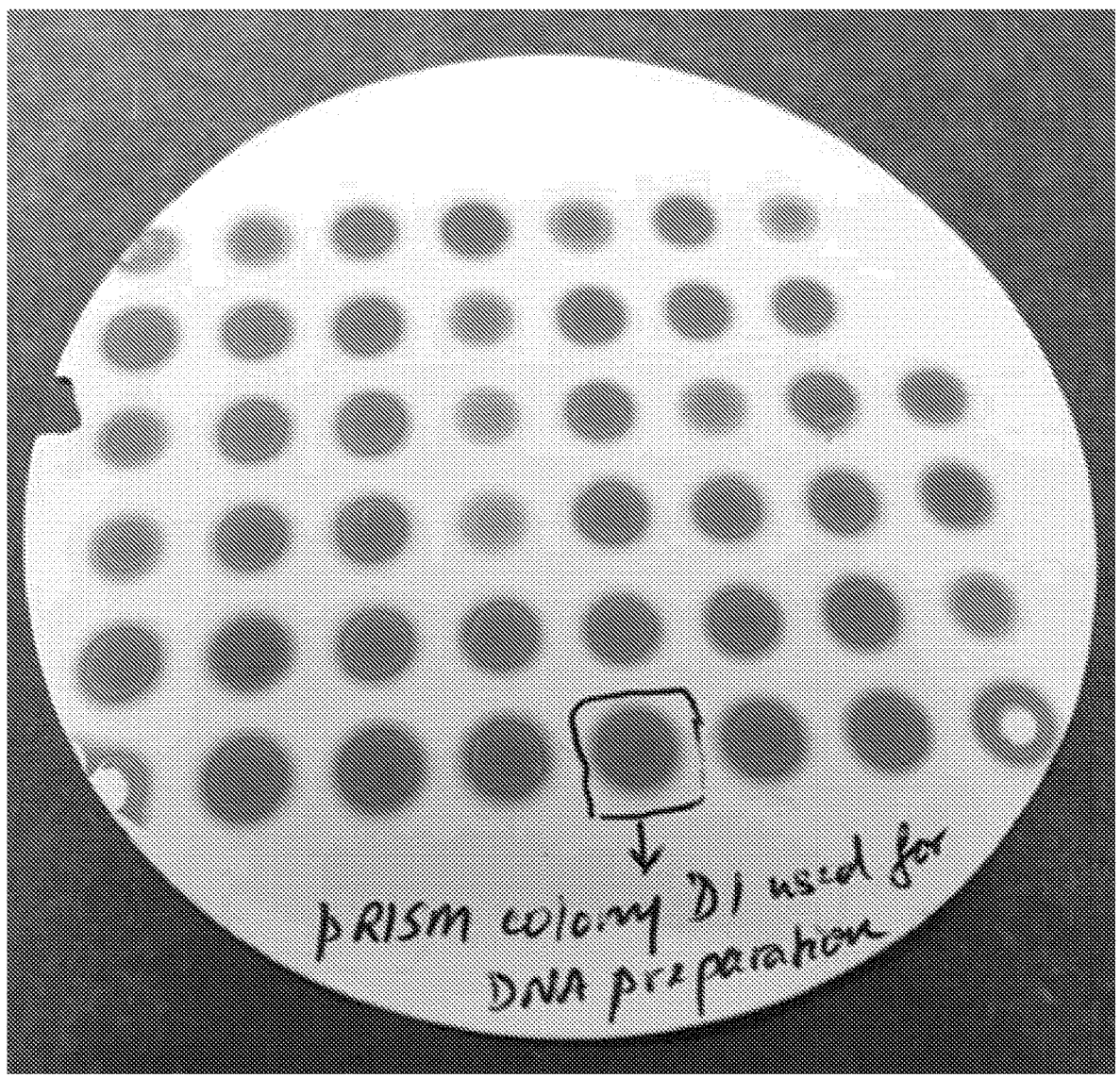
Figure 4:
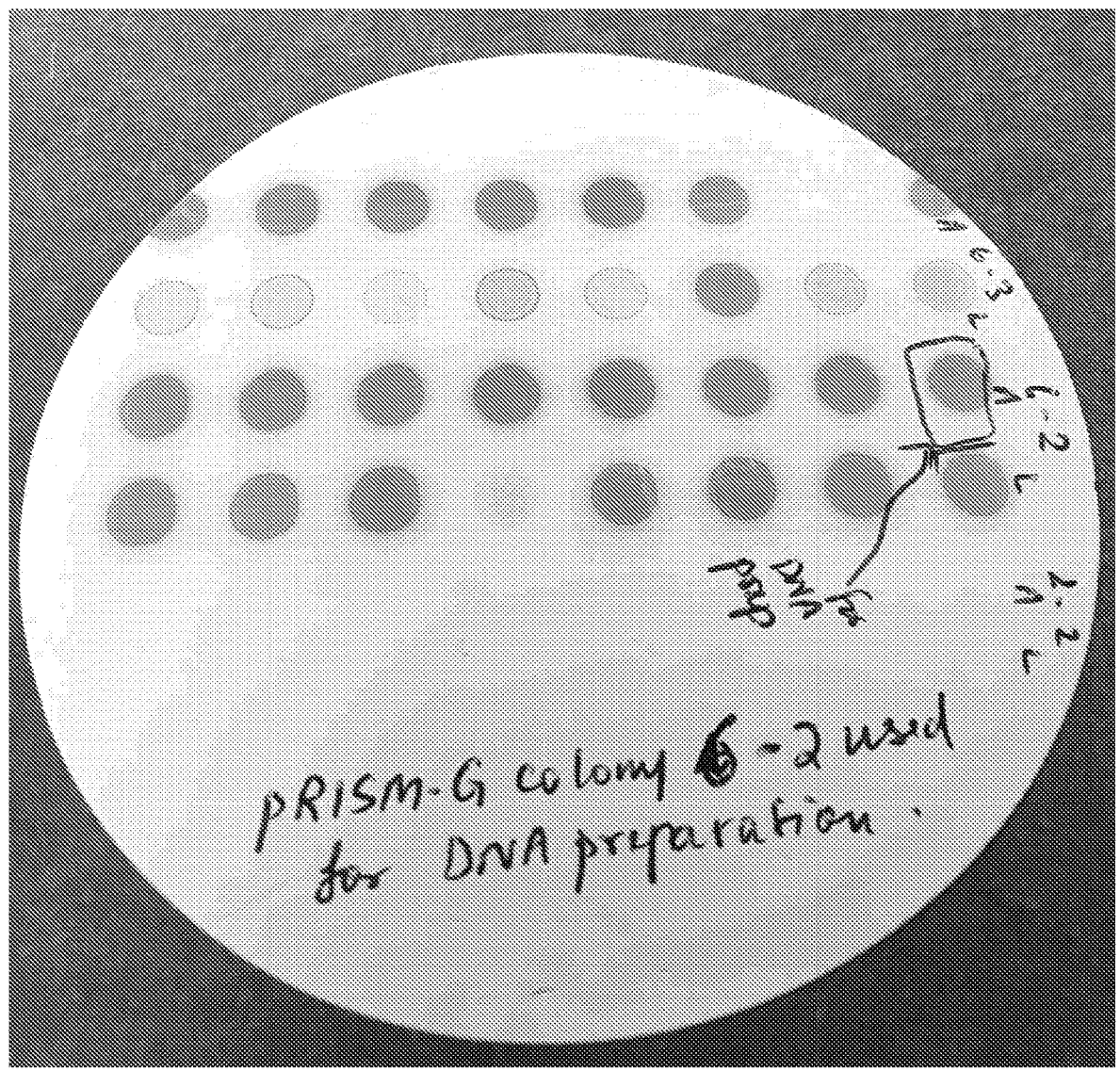

Specification includes a Sequence Listing.

Study 42: mucosal anti-S. flex 2a LPS IgA

Study 42: mucosal anti-S. flex 2a IVP IgA

SEQUENCE LISTING

```
<160> NUMBER OF SEQ ID NOS: 2

<210> SEQ ID NO 1
<211> LENGTH: 40999
<212> TYPE: DNA
<213> ORGANISM: Artificial Sequence
<220> FEATURE:
<223> OTHER INFORMATION: Recombinant Plasmid

<400> SEQUENCE: 1
gctagcatgc gcaaatttaa agcgctgata tcgatcgcgc gccctgcagg taccgttcgt      60
atagcataca ttatacgaag ttattgatcg gcacgtaaga ggttccaact ttcaccataa     120
tgaaataaga tcactaccgg gcgtatttt  tgagttgtcg agattttcag gagctaagga     180
agctaaaatg gagaaaaaaa tcactggata taccaccgtt gatatatccc aatggcatcg     240
taaagaacat tttgaggcat tcagtcagt tgctcaatgt acctataacc agaccgttca     300
gctggatatt acggcctttt taaagaccgt aaagaaaaat aagcacaagt tttatccggc     360
ctttattcac attcttgccc gcctgatgaa tgctcatccg gaattacgta tggcaatgaa     420
agacggtgag ctggtgatat gggatagtgt tcacccttgt tacaccgttt tccatgagca     480
aactgaaacg ttttcatcgc tctggagtga ataccacgac gatttccggc agtttctaca     540
catatattcg caagatgtgg cgtgttacgg tgaaaacctg gcctatttcc ctaaagggtt     600
tattgagaat atgttttttcg tctcagccaa tccctgggtg agtttcacca gttttgattt     660
aaacgtggcc aatatggaca acttcttcgc ccccgttttc accatgggca aatattatac     720
gcaaggcgac aaggtgctga tgccgctggc gattcaggtt catcatgccg tttgtgatgg     780
cttccatgtc ggcagatgct taatgaatac aacagtactg cgatgaataa cttcgtataa     840
tgtatgctat acgaacggta cctgcagggt catgatgatc attgcaattg gatccaagca     900
```

-continued

| | |
|---|---|
| ctaccccgc ctgttgcgac agtcacgtca tcgccgtccg ttaccggaac atgtttccg | 960 |
| cgaaatacac catctggagc ctgaagaaag ctgttgtccg gagtgtggtg gtgaactgga | 1020 |
| ttattcgggg gaaatcagcg tctttctccc ggaaaggcat actatcttac agtaatattc | 1080 |
| attccgatga ttaataaatc agcaatgcgc gcattttaa tataagcatg tacaatatgt | 1140 |
| acttgcatgc attaccctgc taatgcagtt ttttttgtaa taagttaaaa tcctacatag | 1200 |
| cacggagggg gaatgactag ttttgagcag ttaagtaagg ttgcgcagcg tgcagataaa | 1260 |
| atgttgctcg ccctaacaaa acagattcag gagcaaaagc aggagtttca ggctgatgtt | 1320 |
| ttttatcaag tctattcaaa gtctgctgta gctaagcttc caaaattaac gcgcgcaagc | 1380 |
| gtggatggtg cagtcggtga gatggaggct cagggctatc agtttgaaaa acgcccagca | 1440 |
| ggaaccgcga caaatatgc attaaccatc cagaacatta tcgatatcta tgcacatcgt | 1500 |
| ggcattccta aatatcgcga tcgttatagt gaggcatatt ccatattcat cggtagtcta | 1560 |
| aaaggcggtt tgtctaaaac cgtgagtagt gttccgtag ctcacgccct gcgtgctcat | 1620 |
| cctcacctgc tgtcagaaga tttacgtatt ctgctccttg atttagatcc ccagtcatca | 1680 |
| gccactatgt ttctgaacta cttgcatgcg gtggggctgg ttgatacaac cgcaccgcag | 1740 |
| gctatgttgc agaacgtgag tcgtgaggaa ttactggaag attttatcgt tccgtcagtt | 1800 |
| atccctggcg tttatgttat gccggcttct attgacgacg cctttattgc atcaaactgg | 1860 |
| gatactctgt gcgaggagca tctattagga caaaacaaac acgcgatatt gcgtgagaat | 1920 |
| attattgata agctgaagca tgatttcgac ttcatccta ttgatacagg cccgcatctg | 1980 |
| gacgcatttt tgaaaaatgc cattgctgcc gcagatatca tgtttacacc ggtgccgcca | 2040 |
| gcacaagttg atttccattc cacgcttaaa tatttggctc gtttacctga acttgtacag | 2100 |
| attattgaac aggatggatg ttcatgccgt ttgcaggcaa atattggctt catgtcgaaa | 2160 |
| ctggcgaata agtcagatca taaatactgc catagcctga caaaagagat tttcggtggt | 2220 |
| gacatgcttg atgtttcaat gccacgtctt gatggttttg agagaagcgg cgagtcgttt | 2280 |
| gataccgtga tatctgcgaa tcctgttact tatgttggca gtggtgaagc tttgaaaaat | 2340 |
| gcacgtatgg cagcagaaga tttcgctaaa gcagttttg atcgtattga atttataagg | 2400 |
| gccaactact gatggaaaac agaaagcacc gaccgactat tggccgtacg ctgaatacaa | 2460 |
| atatcctgaa taatactgaa gaaatatcgg ctccagttca tgtatttacc ctcaatactg | 2520 |
| gccgaaaggc aaaatttact gagatcaagg ttgatcatga caaagtggat actcaaactt | 2580 |
| ttgtggttga gaggtgaat ggccgcgaac agacagccct gacgccggac tcactaaaag | 2640 |
| acatcaccag aactatacgt ttacaacaat tctatccatg tattgggatt cggactggcg | 2700 |
| atcttattga gattttggat ggttcccgtc gtcgggcagc agctttgcta tgcaaggttg | 2760 |
| gattacgtgt acttgtaacg gatgatgagc ttactgtttc tgaagctcag catctggcga | 2820 |
| aagatttgca gacgtcactt gaacataata ttcgtgaaat tgggttgcgt ttagtacgtc | 2880 |
| tcaaagaggc cggtatgaac cagaagcaaa ttgcggaaag agaggggattg tcggcagcta | 2940 |
| aggtgactcg tgccctccaa gcagcgtccg tacctaaaga ttttgtgtct cttttcctg | 3000 |
| ttcagtctga gctgacatac gccgattaca ggcaactggc tgaattaagt gaacgactga | 3060 |
| ggctgggtga tatatctatt gatgaagttg tgaagaatat ctcgccgagt attgagctta | 3120 |
| ttactgctga tgcaatctt tctgaagacg aggttaaaaa cagtattatg cggcttataa | 3180 |
| ccaaggaaat gtcttcattg cttgattcag gagtaaagga taaagcggtt gtaactttgt | 3240 |
| tatggaaatt tgatagtaaa gataaatttg ctcgaaaacg agtaaaggga cgtacgttct | 3300 |

```
catatgaatt cggcagatta ccgttggaag ttcaggataa gttagatcgt atgattgctc    3360
ttgtactaaa agataatctg aattcgctgt gaaaattcaa gttttcgcc agcaactcgc    3420 cagttttaa ttggctgttt taaaagaaat tttgctttta ttagcgtttt ttttgaacag    3480
tatttcacgg tgaaatcgcc tgtttcaccg tatcttcttt gcttgaaaaa gatagtttct    3540
cttagccgtt taacagtaac cgatgagata gtcttccccc tctttcacgg cagccttcaa    3600
ttgcgccatg atggataaac tttaacaaca aaagtaagcg ggataccatg tctgaacaga    3660
aaatcaccgg cggatccata tagggcccc gggttataat tacctcaggt cgacgtccca    3720
tggccattcg aattcgccct tatgcaatga atcaatcaga gccatccagt ttaatcgtcg    3780
gttccgttca tatggagcaa aagtggtgtt gaagaaacat ccgttttgtg gtgtttttttt   3840 aatcttttg gggttttaat tcctatcgct caagtcttaa cgatatccct gaaacgacca    3900
cttaatatta ctcacacttt tgcaaatgca ttaaatgctg cttgtattat tctgatgccg    3960
caccagcggc atggaaggcg gcacgctgtg gttacatgtg ataccggagt aaaaccgccg    4020
aagcccggcg tcagccggta ctgattgaca gatttcacct tacccatccc cagccctgcc    4080
aagccatacc cgttttcagc catgatagag cttctgtgcg cggtcggagt ggtcccgacg    4140
agggttttac ccgaagtcgg ggcgtatctc cgcgttagcg ggccgtgagg gccgcttacg    4200
agcgtgtatt cgatacgtcc agccagaaga ctgacagcga tgatgatgta gttacaacat    4260
tcacaattaa aagcgactct gttcccgccc tttgggcggg ggcggcggcg cttttcagtt    4320 atgaggggg cgttgtggtt tcagttttgc gttggacttg ggttttttag gggtttatgt    4380
ttgcatgttg taactaaacc ggcttcggtt ggggccccgc cgcttgcggt gggaggtgca    4440
tatttgtctg tccacaggac aggcagtgaa caggttttct ttttaaatga atgtaattaa    4500
gtagtttaaa ggagatataa acaggtgttt aaaagataca ttgcaccctg tagggttgac    4560
gtctggcgct ttatgacgtg aacggttgta accttatggt gaagtccctt gcagtttaat    4620
gtggataagc aaaattcccc gtctgtgagg cgtgttttgt atcaaaaaca gggggaccg    4680 gatgcacctg aagtggatg atgaggttgt ttttgtatg tagcgctgat ttttgtgca    4740 ctggcgggct tcaggcgtgc gaatgcctcc ggcgcgtgcc ggattattct gaggaggtca    4800
ctttcagggg gaagctgtgg ccagccggct gtaattacgg ttacgtgaca gaatcatgcg    4860
ctccttcaca cgacgctcca cttcacgttt taccgcctca cgactggcag tgaagcgccc    4920
ttccgagatt tcacgcgtca gttgccgttt caccagggtg acaatatcct gacgctgcct    4980
gtccgcatca cgacgcgcac gggcacgctt cattccacgg gacttaagct ctgtctggta    5040
actgcggaaa cgctcacgaa caaaacgcca ggctttcgcc atcagttcat ccatacccag    5100
ggtatccagc cctgcttttt tgcgctgtct gttttcccat tccacacgac tgcggcgcgc    5160
ggcggccact gcctcctctg atacatcgag ggcagcaaac agtgcagatg tgaacgtgat    5220
atcggtcgga atgtagcacc cgataagcgg gtcatattcc gtctggtagg taatcagtcc    5280
cagctctgca aggaacgtca gggcccgggt ggcccgggtg atggagagtt ttccggcagc    5340
agactccgtc gccagtccgc actcaatggc cagcgtggtg atggaacact ggacgcggtt    5400
ggccagtggg tcatagtgaa aacacagccc ctgcagcagc gcatcaatgg cccggcgacg    5460
tagtaccggt ggcatgcgcc gacgcagacc aagcgaacgg gcatgtgcca catgaatggc    5520
gaaatcaaaa cggagtgga agcccaccgc cttttccatc agtttcccgc agaacggaag    5580
cgtccgggca ccttcacggg gtgtgaacac cggattcggg ttctttacct ggcggtaata    5640
```

-continued

```
agtttgttga agatcagtca caccatcctg cacttacaat gcgcagaagg agcgagcaca    5700
gaaagaagtc ttgaactttt ccgggcatat aactatactc cccgcatagc ttgattgttg    5760
gctgtacggt ttaagtgggc cccggtaatc tttctgactc gccaaagtta agaagatta    5820
tcggggtttt tgcttttctg gctcctgtac atccacatca gaaccagttc cctgccacct    5880
tatggcgtgg ccagccataa aattccttaa acgatcagta atctagcatg ctacgccaca    5940
aagtaaagtc tttactttag tatatccagt ctctgcagtt catctttgat gattttctca    6000
acgaactgag cctgtgttat cccctctctc tcgcagtact caaccatgag atctttcaga    6060
ggatttttga caaaacttt tatctctttg tgtgtaagac gttttcttgc aacagcggcc    6120
agttgtttct cagagtcagt cataggctta cctctgcgca caaaccgctt ttgactcaat    6180
gaggaagtca ctgcattttc tgtctgcgac atctcgcctc ctcaatactc aaacagggat    6240
cgtttcgcag aggatactat tgcataaggg cgaattctag ctcactcatt aggcacccca    6300
ggctttacac tttatgcttc cggctcgtat gttgtgtgga attgtgagcg ataacaatt    6360
tcacacagga aacagctatg accatgatta cgccaagctt aaggtgcacg cccacgtgg    6420
ccactagtac ttctcgagct cacatgtgtt taaactgtac atgtggcgcg ccacatgtca    6480
tggccggcca gtgctaatca tttggtatct ttcgtgtat tctccttta cgtaagtact    6540
taagggaac gtatttacta ctttaaaga aagctccgtt actatctgaa atgcaatgag    6600
ataataaacg attactctcg gttagtatct catgatcatt tacagacttt gcataatcgc    6660
gaatactaca taacagagtt ttaacattac aggatgaata gtctctctta tcaactccta    6720
ataaaagaag gattatggtc agtcgttttt gctgtcttat catatattat ttagtgcagt    6780
tcctaacaaa aacataacaa ttttctacaa ttgatcctgt gactacataa atatcttcaa    6840
caaaatatt tatatcagca aaagagttat tatgaatgat tataaatcat caggtgtttt    6900
ttcaacgacc aactccagag cacaacgata aatgtctttt ctaaccaggt cacattcaga    6960
tgaaatcttt ctgagtaaaa catttattat atccttattg ctaaggaaag atattgggtt    7020
caatacctca ttagcaatgg agttaatgat ggaagattct atttcaaatt cagactgatc    7080
aatacctatt ttattacaga aattaactcc catataacac atctccttta cttattaatg    7140
agtgttttca acctgctcaa gccaaacaat aagacgtagg acttcatcca agtgttcaaa    7200
atcaacaaaa ctatattttg tatgtgtttt atatagtttt ctagctaatt tcacatcacg    7260
cacagtcggt ataccaactt catttgcata tttttctgaca gccaaggcac actggttagt    7320
ttcaatgaga gaaataaaag gtgcaggcgc tatttctgga ttaaaataaa taccaattgc    7380
aatatgagtc gggttcatta ccactaattt tgaattacgt atatcagatt tagtctgctc    7440
tgaaagaatc tcgatatgca actcacgcct tctcgacttt gtctcaaagt gtccctcttg    7500
ctctatatat tctcttttta tctcctgttt atccatcatc atatctttca tgtataaaat    7560
gaactcaatc acaaagtcaa gaataataac aagaatagaa aatgccaaga aaaataatat    7620
tatatcctta aacagcctcc cccaaataag atataagcca tcaacactag aaaacacctg    7680
agaaaaaatt attttttcggt cattaatcca aaagaaatag gttgttaatg ctagaataat    7740
aagaagcaga atgctttga aaaattcttt tattgtcttt atactaaata ttttttttaa    7800
ccctttaaca gggtttaata ctgaaaaatc aatcttgata gctttagtcg caagaacaaa    7860
ctttgtttga accaatgttg gcaacacagc cgaaagaaca cagaaaaaaa gtgggaagcc    7920
aattatctta aaaagacaa taccactgc aaaaaagtat ttaccctcat taatttcgaa    7980
gtcattaatt attacatatc tgtataagag cattacatca cttaaggaaa agaatgatat    8040
```

```
tatagtaaat gtccctacca gaataataac aacagtcgtt aaatccttaa atttaaatga    8100 ctgtccttttt tttgcggcat cctttagttt tttaggtgtc ggcttttctg ttttatttgc    8160
cataatattt tatctaacaa atagatttgt gaaaaattta tgttcaccga ggaaaaattg    8220
aactttagaa aagtaaatag tagaagaaca gatgaaaata ataaatattg caagtaaact    8280
tttaatagtt aatgatacgg aaaaagcatt catctgcgga gcaaatctcg ataatacacc    8340
aagtaatact tctgatagta acaatactat cataacagga ctggctaaaa taacagcctg    8400
acttgccaat aaagtcagaa atgttaagat atttgagaca cggaaagaac attgagaaaa    8460
taacgggcat atattataag acaattgtat ggattctaaa ataagacca taccaccact    8520 gtatagaaat acaactgcag aaaaaagatt gaaaaatttt gccaactcag acgtatcaac    8580
accattggca ggatcaattg aactactaag cgttgccccg cgctggttgt caataatgct    8640
accaacagca tgaaatatcc aaaagggaag agacaagcaa aaagagagaa ggaggccaac    8700
aattatttcc ttgaacataa ggaaataaac atgttcaaaa acagaagaac ctatgtctac    8760
cttaccagaa gtaattaatc ctgatgcaac aagaaaaatc acaggtattc taatagatgg    8820
agaaattata ccgttattta aaaatggaag aaagaaaaat aatggagcca atctaaaaaa    8880
aacgccgttc aggagtatta aaaacacatg aatactttcg aaccagcttg aaatgtccat    8940
caaaccccac tcttaattaa aaacattatt tcatgacaaa aagacaataa aacctcacca    9000
taccatccag aaagaagtag caaagatatt gagacaccta taagctttat accaaaagga    9060
agtgtctgct cttggagttg agtcactgtc tgtaacaaac caatagataa tccaataacc    9120
gtagctatac ctactggcca taaggaaaag ataaggatta aataaagagc cttattaccc    9180
atataaacta tatcagacac attacctcca tcatctaagc aggaatattg atatattgtt    9240
caatcaaggc cttagacagg atacccccacc catcaagcgc aacaaataat acaagtttta    9300
ttggtactga tattgtgatt ggactcatca tcatcatacc aagtgcaagt aaaatgcttg    9360
aaataacaag atcaacaaca acaaatggca aatataaata aaaacctatt ttgaacgcat    9420 cttttgatttc acttagcgca tatgcaggca agagggaaaa caatgaataa tcattattct    9480
ctgcactctt taaatcagca ttttcttctt cagacctttg gaaaaaacgt gctaactcaa    9540
gatctgtatg cttttttcaag tattgcttat attccatcaa gccagaatca gaaaaacgga    9600
caatatcaga tattgtatca aatttttgag ggccatttag ataattttca taccagctt    9660 caataatggg tttcatcacg aacaaagcca taatcaatgc aataccattg agagtcatat    9720
ttgatggaac ctgctgcaaa ccaagtgcat ttcgtaccat tacaaaaaca atagaaaact    9780
ttatataaca ggtaccagca gcaactaaaa atggtaatag cgtaaaaaaa gaaagtgtag    9840
cgatgaggga catgtcactc agcatgagat tactccttta ccatccaaga actaatctcg    9900
ataccataac catcctcaat agaaacaagt tccccatgcc caaccaaaga accatttact    9960
ttaatattta catgtttaac tatgtcatcg ggaaacttga ataattcgtt ttctacatac   10020
atttttagtt cattgattgt catatttttt tctaaaagaa taaagtccac ttttacattg   10080
atatcatcat aattgaataa tgccaaagaa acttctgtgt gttctgactc accattactt   10140
tctgacagat taatttttgc ctcattatta tcattcacaa tataatcccc aataataact   10200
tgattacaca ataataaatt ataaagtttc tgaactatga ttatatcacc agtgcgaatt   10260
ctttttaaag tagccagcct tacattagat gaacctaagc aaaactctaa aagatgatgc   10320
aatgagtcaa gagaaacttg attacgtaat accggcatct tgtcaaaata aataataccct   10380
```

```
aaagaagagg aaaaacagca taaatgactc ccagtagttg catactggat ttcattcgtg  10440
atccggaaag taatcttatc agacagttct ggaatcgaaa atacagatga cgactctata  10500
aagacacatt ttgataaatg cagtaaagat tcttgtgtag aaaatcctga aaataccctcg 10560
tattttttt  tcaaaaaaga taatgtatca atacgaatta cccaatcccc acacacggaa  10620
gtaagagtga ctaaactttc actgcctgta aatttatttt tgaatgtctg aatcgaaaaa  10680
cgctcgcaga gttgctttgc atataaaatc tgtagttttt cgttagcgtc aaaatgttta  10740
attcttagca ttcttcttca ctctgttcat tatatcctgt actattattt ttattcccct  10800
tattatgttg actgctatca aatctgtaat taccctcagc atcttgtttc aaaattaagt  10860
caagtttatt tcctacaaat tgatctgacg gttttagaac aaaagaacca gactccactg  10920
aaatactaac agaatgtcca gcccccccact gtttaaagtg gtaagtcatt tcactatttt  10980
tttgaaaaac attttatca  ttttcaacta ttgattttc  ttgcaatgac atggatgggg  11040
ttatgtctgc agtattttta ttcattacag gcagctcaaa tgatttagca acacttccat  11100
ttagtaaaga aatgatgtca gcaatattct tatcaataga caagctatga ttttttaaac  11160
caatttgacc atttctatta tcagattcta gcagattatc agggtttaca gaagaagtat  11220
gacttctttc gaagttcttg tctgcatttc cactcttatt tatgaaaag atcccccctca 11280
tatcgccgat atttatttt  tcccttgctt tgatatcttg atctggtatc aaaatatttt  11340
ctttaatggc cattgattct ggaatatcag aatatgtcgc tcgttcgttt ctaagttcga  11400
acgcattttt aatgccacta taaatttctc ctttatcatg cttatgttca aagtgcttat  11460
caatagtaaa atagttagat gcaattaaag agtactcagg aatttcaacc ttcctcttct  11520
tcttcaaaac gagactatca atattatcta ttgaagatag tttctcacat ttttctatct  11580
gtttgtcact actaaaattt aggtttatat tatctaatgc catacttcat atcctcttgt  11640
gataactcat caagtatcaa ctgtttggca aagttatttc ttttaatcaa gccaatccgt  11700
ttacatattt tactctcttt atgaagcagt tttcttttag aagcatttgc ctcatcaata  11760
tcttttgaa  tttcttcaat tcttcccttt agaagaattc gttcagactg atattggata  11820
atatgctttt ttactatagc gatcttacgt cttgtattga aaagctgact aacactctga  11880
gcgcctacag gttctaagtc attctccagt tgcaggaagt atataatcct tttatctaat  11940
gcctccacat ctcgatacaa agagttttt  ttttagtgtt aatatgtgtg cttcaattaa  12000
tttaacagac cgttgatatt tatctttgat ttttaaaacc ttatctaatt gtttcaccaa  12060
taagctccat tgtctgctca taagtaaaac cgagtcgata atcttgcttc agaaaactct  12120
caacaacaga tattttgttg tagattttat cctgagaggc attctccccc ggtttgtatt  12180
caccaaagtc aataattgtc cttagctctt ctatttcaga aagtagctcc cgaaatgcag  12240
cggccataat acgatgtttt tcatcaacaa cctgtgtaaa taccctgctt atactttta   12300
aggaatcaat tgcaggaaat tgtccttttt gggctagatt tctgctcaaa tatatatgtc  12360
catctaaaat ggatcttacc tcttcagcta atggatcagc aaaatcatca tcctccaaaa  12420
gaacagtgta aaatgcagta atagagccac ctgcctttaa cttttcctggc ctttcaagaa 12480
gtctgggtaa gctatcaaaa accgaaaccg atagcctct  tctggcaggt gattctccag  12540
cggctaaggc cacatcacgt aatgctctgg catccttgt  taatgaatca ataaaaagcg  12600
ctactttatg tccttcagtc ctaaaaaatt cggctatagc agtggctata tatgcagcat  12660
tacaacgatc aaccgaagag taatccgaag ttgcatatac taaaacacac ctgctttttt  12720
tctcagagtt tttcaaataa tcaaccgttt cagtaacctc tcgacctcgc tcaccaatta  12780
```

```
acccaataac atatatatca gcaccactat gttcaatgag catattcatg agaaaagttt    12840
tgccacaacc agctgacgca aaaatcccca ttcgctgtcc ttcaccacac gtgagtaaag    12900
aatcaataac cttaatacct gttaaaaaag gcttctcaat tgcagcccct tcactatata    12960
gcggaggagc attatctaca ggtcgataaa gaatttcact gttatctgta acagcaaact    13020
tatcagtaac ctcccctaaa ggattgacta ctgctcccaa taatccacgg ccgacttgcg    13080
tatgaagaaa ctgggcagtg gcttaatcaa acgtttgccg tgaaagtcca cgagaatttc    13140
caatcaagct taatattgtt ttttcatcat gaaatcctac aacctgagct cttgcaacaa    13200
tttcattact ttcaattcca gcctgaatgt tacaaatctc accaatcgaa acatcgctaa    13260
gacttgtttc caagattggc cccgagattc tattaggaaa agataattga gtgagcaatt    13320
ttgtatagct cattgattat aagaccccat ttaagatttc catcctctga taaaactcat    13380
gcagaatctc tgcaaaaaca atcccatcgt gaacgtagtc atctttaata caactcttta    13440
actgtaagta ctcatcagaa cgatgaagct ctaccagctc attaatgcta taactaaagt    13500
tcattaacat taaatttaat atgttataag cagatgactg aagttttaca tcacttggtg    13560
catcaaaatt agcccataac ataacctgct cattgacaag agctatatta atagcaggca    13620
tactatccaa agaaatggta atcgctgaat ggctgtctaa atctgtaata attgatggag    13680
gacaaccaat cgtgaaaaga ctatctctaa ctaattgaac taaattaatg ttactcatat    13740
ttaaacctca ctaaatagtc tttaatacat taatggtata tgcttcatca atctcagcat    13800
acgatataac gagtatactc ttaaatctgt tatctataag tcttttaaca aacctacgta    13860
tatctactga taccaaaaga acgaaatttt tttttgcatt tctcaattct ctcaaagcat    13920
gtgctaaagt ttccattacc tcatccgaaa cctctatatc catattcaag aaagagccac    13980
cagaggtttg ccttatccct tttcttattg catcctcaat atatccggaa agcatcacaa    14040
ctttaatctc accagaaaca gctatttttac tacaaatata cctagaaagt gatgcacgga    14100
catgttcaac taatgttatg acatcttttt ctctgggagc ccaaagcgcc aaagactcca    14160
taataagttt taaattgcga acagaaatat tttctccaag caatctttgt aatacctcag    14220
aaattctctg tatagtcaca tgtcggaaga cttcctttaa tagatcagga taccgatttt    14280
caaactgatc taacatattt tttgtttctt gtataccaaa aatctcattt atgttgttta    14340
ataaagcttg tgacaactgg tgataaaatt catcttgagc actttaatt ttagcatcaa     14400
tattagttag atttttctgta tatgaaacgt ctacccaaga aataacacgt tcattatatg    14460
aagttgaaac aacaggaata cctagagcat ctatatctcc attttcatct gtaatacaca    14520
ctttgtcaaa atatatatta aaactatcgg cacgcacctc atttattaac aaaacaatat    14580
catcgacctt aagctcattg cttgttctat ataaaatagt tggaagcctg acaccataat    14640
caataaagaa ctgacttctt atcctttcaa taagaccttc catatcattt gcatttatct    14700
tatttttcggc aaataataaa attaaggaa cggtttctga actaatagca tccagatttt    14760
ctatcattgc caaagatgag tcatggctat tatcaatatc aaatgtacca gtatagccac    14820
tagaatcaga ctcagacaga cttttttctt tttctacgac cttttttataa tagaataaag    14880
ccgtcaaagt aactgctatc aggaaaaaaa caaaaacgg aaaacctggc aacatcccta     14940
tcgccaaggc aagagctgat gtaacaatga aacaaaagg attcccaaat atctgggaca     15000
ttatgttacg tcccatatta tcgctatcac cattaactct tgtaacgata aatcctgcac    15060
ttatagaaat taacagagca ggaatctgag agaccaatcc gtcaccaata gttagtatgg    15120
```

-continued

```
tataagtaga taatgcacca gatagggaca ttccatgttg actcatacca acagaaatac    15180
ctcctattaa attgacaaaa ataataatga tgccagcaat tgcatcacct ttaatgaact    15240
tcattgctcc atcaaatgaa ccatacaatt gactctcacg ttccagaata ctgcgtcttt    15300
ctttagctcc tgcggcatca ataattccag cctttaaatc cgcatcaatg ctcatttgtt    15360
tccccggcat accgtcaaga gaaaagcgag cagctacctc cgcaacccft tcagatcctt    15420 ttgttataac aatgaactgc acaacagtta ctattgaaaa ataacaaaa cctacagcca    15480 gactatcacc aatgacaaac tggccaaatg tagtaataat tttacccgca tccgcatcaa    15540
ctaaaattag tcgactagta cttattgata aagcgagacg aaataatgtc gttatcaaca    15600
aaaccgaagg gaatgtagaa aaactcaata ttctttcaat ataaaatgat cccataaaaa    15660
cgagaatagc aagtacaata ttaagcccta ttaaaaaatc aacaaggtat gtaggtaatg    15720
gtatgatcaa catagcaatg atcataacca taagcactaa tataattaat tcaggcttag    15780
tacttacttg cttaagaaaa gactggatca ctttttatctc ctgttatcta gaaagctctt    15840
tcttgtatgc acttgtgaca agctctcgta gaatattgat cgcaatttct ctttcacttt    15900
cacttttaaa tatatcatga ggactttcat taacagaaga tagatatgtt tgatacacta    15960
cagaatcctc atgactggct cgtgatactt ctataacaga agtaagaatt tgctcacttt    16020
cacttggata ttgaaaaata tataataaag ttagcaatag ctgctctgca cttaaactgc    16080
catcttttag caagcttgag gattccagtt tcttcataaa aattacgtct gaagttctaa    16140
tcatcttaat tgcaattaat ttagataaca caaaccaaa ctcataagca ttacagctcg    16200
gtttctcaga atccatgtct acaatcagtg actgctctac aaaattcaca attgtatgtc    16260
tgtgattaaa accaaaatta ccaagccatt ctatatactg atctgttgtt gatatgttcc    16320
ccatgataaa accacgataa catgcacgca aaagctgtgg ttcaagtttc attttgttgc    16380
caaataattt agcctgtata gctgaattta ttccagcatt aacactttt tcactacctg    16440 atattatctc attaataatt ttagttaata attcgacttg ttcagcagta agatcttttt    16500
cattcaaaag ttcccttaat gctaagactt gatcacttgg atctttaaaa tatctcttta    16560
gtctgtctat aaaatcccga tctagaggaa ggttatcttt taacgttctc tttaaatcaa    16620
aaatcttgtg attaatttca tcttcttccc catctaaaat acgttcctga ctatcactat    16680
ttgttccttt cagtttctca aggtctcttc tgtttataaa tgacgaaaga gcggaagcca    16740
tctcatcaga tgagtcaata tacttgctat tagccaagcc agaatcaagc tctgcatcag    16800
cagtctcatc tccatcatct gaatttgtca ttgcattcaa cttatcaatg aatgcagagc    16860
taaaaactcc tgtatttta acatcaagca tacatcacct actttatagt tagtaattta    16920
agtatgaaac caatgatttt tcgtcttcca gcaaagtagt ttcagatggg attatttgtg    16980
tagtcttttg tatttctctt tcagatatga ggctttata ttctgcagta ttataataac    17040
ttgactcctt tatctcacgg ggttgaatca gaaaaaccct tacaatatta ctgatattac    17100 ttgtttata cttgaacaca ttaccgatta caggaataga ggagagaaaa ggaatagata    17160
ttatttcgtt agagttcgtt tcatgcgtat aaccacctat caacaaactt tgccttgtg    17220 gaactctcgc tattgtactg attttggtcc ttccaacttc tggaaggaca gatgtatttt    17280
cattattata attgtaattt gactgactat ttcctgttcc atcctctatc gttaaagaca    17340
tctcaatttg tccccgagat gaaaagcgag gtataacatt tatcaatgtt ccatacgtaa    17400
catgctccaa cgaagaattg cgctcaccaa ctaatgacac ataaaaagtc ctgttattat    17460
caaatatagc cggaatattc tcttgtgtca aaatcaccgg ccttgaaact acatttgctt    17520
```

```
tcttttctg atttaatgcc ataactgaag caataaactt attgccgtcc aaagtgctta   17580
tcgatgctga tgagctcata ttaaatgacg caccaaacga atcaccaaat gaagccgttc   17640
cttgccaatt aacaccaagg ttatttaatt cagatttatc aatatcgatt atccataatg   17700
ataattctat atgtcgtttg gctatatcta actgagtgat aatatcgcga ataatctgta   17760
tttgctgatc attacctttg actaatatag aattggtttc tggatatgca ataagtgata   17820
catcctctaa tatagaacta ttggtaactg aactaaatga aaagtcatta ctatcctcag   17880
atactttctg tgtaatatta aagggtggca tcggatcatt ttgggcttgt ctgttactca   17940
gagccttacc attatttaat aaacgttcta caacagtagc caccctggg atgacaatat    18000 cctcccctct catattataa gttctgtcac taacaaatgt attttttaat tttataaccc   18060
caaaattaac tttatctgtc ccaatagaag aaacctgctt atcaagcaaa gttgctgtat   18120
tagctaccag ttcaaccaat gccggaggac cagatatata gaatgtttta tcactaatgt   18180
ttcctcttat aggatatctg tgatcataaa ggttagcatc cttcagatac tgaataagat   18240
aattaagtga tatattctcc agcaaaataa ctttgcttat taattctcca gagtcatata   18300
tgtataatgc atttccatct ttataccata tgagtcccac aagtaatgtc agttttcaa    18360 gcatttcttc tggattagat aaatcaaact ccccagatat tctcttttt gcagcttgtt    18420 tgctaacaac aataggataa tttaataacg cagaaaaacg ttcaaaaaaa gatcctaccg   18480
tatcactttg agcaacatat ttcgctatgt cattttgttc taataaatga gagtcaatat   18540
tattagcatt aactatcaat ggtaacaata caatcaagag agtcaaagat ttaatattaa   18600
attttttcat ttatttttt cactaaaaaa gtaatattcg ataattctct tgcagaaaag    18660
cctagtcgtg ttttatctc atttgaaaaa tgggatgttg atgcataccc attattcatg    18720
gcagctgaag tgattgtttg attgtgcaaa aatacatcta ataaaccatt tactaaccgc   18780
caagtgttca gttgttcttt gactttgcc cctaaagctt ttctacataa agatctaaaa    18840
taagcctccg acacaccata atgctctgtc agactcttta ttcttacctc cttttctttc   18900
tcaatagttc tcagaagata aagaaccaaa tgatatgact cagtcattcg tatcatagcc   18960
agtgcattac ttcattctg gtcagatgaa aagatgaatc ttaacattaa cttatcaagc    19020
atcgattcgg tattcaaact atcccgaaga tcattctcat gatagaaatg aatacatttt   19080
tcagcatggc tatgctctac tagagcacca ctgaaatagt cccaaaaagc aagaaatttt   19140
gcacaactat taatgttaaa gcgataatga tagttcacat tatcactgaa ttttatattt   19200
tgatttcgga caaaaaaaaa cccttccatg ctggagccag ctcaattatg ttacgttctt   19260
tatcttttac aagctcaacg ttaactggtt catgtccact agagtaaatg taaacatat    19320 tacttgtatt tagaccttta tatttactca caatacaatt atatccctcg aattaatttt   19380
aatttaactt ccccatcctt ctctataagg atggtatcat ttatcttatt acctttaaa    19440 acaaccccgt ctttcagcat agaaaatagt ttatctatag ctatcttttg tgcatccatg   19500
aagcacccat ctacttcctt aacattaaag ttgcccatga atttacctgc attaaaacta   19560
taaaccgcct taccactaat acatttagag taaacattta acttttatt ggttgtatta    19620 aacgaccata ataaatcatt tggaatagaa aaataatcct tacttacagg aacaatatgc   19680
cattcttttt cagaattaga tgatgacttt aaagcacacc cactcagtgt taatagcaat   19740
atacttaaaa taaatatttt caacttatta ctaccatgtc gaatcatctg cctctctccc   19800
tgcttcaaag acactaatta atgaatcgaa ggttgtagtc ttaatataga aatcaatatt   19860
```

```
gttatatatg gacaatgatg cataaaatcc ctcatgcaaa tcgacatatt gatttgcatc    19920
tatgagttta ttaagaagtg aactttttg tgcagctgta agataaggaa aacgtgaatt    19980
gaataattgt tcaatcttat tgtgcagttc atcattatct atggaattta attcactctg    20040
tgagaaatat tgcattattt catagattat atcctcatca aatgattgcg aagatgataa    20100
tctctcattt aaattaacaa cttcttcact atttaatctt tgctgcagag cattgcttgc    20160
atttatttga ttaatcatta acaggattct cttttaacaa gtcttctgca atttgtctca    20220
gtttcttatg tgctaactct ttgaaatatt ttttatcatt ttttgttaat ttttccgcaa    20280
gttctatttt aacacctgat attacatcct gaggactaaa ctccactact tgattaccac    20340
tacagaatat ataattattc ccttcagaat attttaaaat aatcttgaca tctgagcgat    20400
atttatggag atcaagttct aacttttcc tcagtgctaa attacacttg ggcaaaacca    20460
cttttaattc tgttactgta ttacgcaacg aactaagcca ctgctccaat aaagtgctaa    20520
tgatcctctc atcatgtaaa ttttctgaaa gcaaactagt tatatagtcc tcaatatttc    20580
ttctattttc attttgcttt aacttccatt cacaaatata gtcaataata tgctcaaaag    20640
cagtctgtat accaatttga taaccatcac atacagcatc tatacgcagt gattcagctt    20700
ttttcgtagc ctcctttata acacaaattg ctttcttctt actctcagtg tctctatctt    20760
ttatggtttt acataattcc ttttcaattc tctttataac aacaccatca taggcatgat    20820
gtctggatac cggtaaagtg ccttttgca tattgcatac cttcatttaa tcgggacaaa    20880
tttctttcta caggcgtata atttccctcc aaagcaattg gattaaataa taagtttatt    20940
ctttcatata taccaacaga tatattttcc ttccacgcaa taagatgcca aaaccactt    21000 cgaatagcgg cctcccctttg cttactgatt ttgcccccat aataactaat aaccatctca    21060
ctatgattaa ttaaccgaga ctcttgacta ccgataaaat aagcaacagc tggaagtaaa    21120
ttccagttgg caacaaacat agcggttacc ccgcttaaag gttcaatatc gcaatttaga    21180
tcatatttat taattatgag attattaatc tcacttctga ttacgccatt ttctaacagt    21240
tcagaaggca aattcaaccg atttctattt atatagaacg ctggatcaaa aattattgaa    21300
agatattttt tataaattcc atccattctt atcatatttt gtttctcttg aaccaccctg    21360
ttttgaatgc ccataccaaa agaatgacaa ctagtacagc catcccgaga aataaatata    21420
ttacttcatt tgttaaaaat tccgatttaa cttccttaac aggttgtaca tttgtataaa    21480
catattcttc tttcggagtt aatatgacag atatattttc atacttaaca tcagaaaagg    21540 tgttttcaa aaatcgctta atattactaa ctaatagttc agactctttc ggtgagtcat    21600
atatagcgat tactgatata tgcatcggtt ttgaagatat attttttct tcaagatcat    21660 agctaacatg tattttgcc gaaataacac caccaataga aactaaagac tgttccagcc    21720
gttgctcaat agcactatat aaacgggcct tttcagctct tggagaagac actaatgaat    21780
ctgtaggaaa catttgtgag atatcaactc tctccggatt tggcaaatcg tacatgcgca    21840
tcaaatcaac tgccgatgca aatgtcccct tttcgacttg taccgagatc ccctgtttac    21900
ctccatcaac ttttctagca gtaatattat ggcgttctag cacagatatt atttcatttg    21960
cctgtctttg agataaatta gaattaact cttcacgttg ctcacatcca atcaacatca    22020
gcaacaagaa taaataaaa cctttatacc taatcatata aattaagact ttaataaagt    22080
ttcaacagcc gaaactgttt tcttgctaa cgtgccagct aatgatactc ctattgaata    22140
atttgagagc gtcgtctgta acttggccaa agattctggg tttaatgatt ctggattgct    22200
taccatctcc attatttgtg atacttgaat atctgtatcc atcttaatat cactatattt    22260
```

```
agccgacacg acgtcttcca gacttgatat ctcttgagat tgaaaatcac tggctttgat   22320
aatatcaacc tgattgactg gataaatgta attcatgaat gctccctatt atctgaagtt   22380
ttgaataatt gcagcatcaa catccttaat cactttcact gtattggatt gcgcgttcct   22440
atataatgta tattcagata atttactttg gtattcagcc agcaactgtg gattcgaagg   22500
atttttagct aatttatcta gtgccaatgt tagttcacct tgtaatgttt gagttccatc   22560
atcaaaagtt tcagataatg aactcaatgt ccaatcatca ttcggtactg taacactcat   22620
tttatcctca cttatttta tctaaaaaaa accagtgttt atcattcaac attacataac   22680
tgtctttgct gttaagatat gatttacctt taaaatcatc atctatcaaa agtacagaaa   22740
actcaatata ctgatctcca tatatatttt tatgttcaga aatcagtcta ttaatgagct   22800
caagcttttc atctgtcagt tcttctctga cagaatatgt aactttatta ttttcacaaa   22860
tctctttata ctggacattt accttttgtga aaataccttt agcatccccc cttgcattat   22920
gatcgctaag atagttgaat ttaatatttt tgatatacgg aaattcaaca atcagagcat   22980
ttttcaattt atcaagttcg gtatcttttg aactattct ttctttactt aaaaacacca   23040
gtaattccgc tttatcactc actaaattca acacatacaa attgataaat gggaatcgtt   23100
gattgatata ttgttgaatt ctatttattt ctttgtttga caccagaata tatctgcatt   23160
tggtaaatcc ggttttattt aaggctacag acgcccatac cgcatcattt tgtgtttcgg   23220
caagaatata attgcactgt ccagtgttga ctattccata tctcttatca tctataattt   23280
cagcaatttc ttttacttca tctttctttta aagagaggga aaaattata attaacacaa   23340 caataacagc aaagaaaaaa aacaccgagt ggttcttata cattccgttt agtatatggc   23400
ctctcgattt atcctccctc atatttttaa ggtgaaaaga atcccgtca tattcaaatg   23460 aattaaattg tgaattgata tcaatttgct cacctttttc atcactaaat tgacagatat   23520
tatctttgct tatggtcaaa taaattatac catccgattt actatctgtt acaggaataa   23580
tattttctgg gaaattgtcg tttccaaact caagtgtttc tatcgtccgt ccgagaacaa   23640
ttaagttatt cccataatat aacggaaact catccccgac accgtttgtg agtttcacta   23700
ataacctgaa tggtgcaaga tttgagttct ttgcctcaga cataaatcct cttatatcct   23760
tcgattattc tgcttgctct ctgctgctat ccgcaaatag cgtctataga tatcctctgc   23820
gtactttaat ctttcttttt tctttttcgg agacgttcct gcattatagg ctccaacagc   23880
ctcccaccct cttccataca tcatcataaa ctcatttaat aactttgctg cataatgtac   23940
agaaagacat ggatgactaa ttagcatttc ctcagaatat cccatttctc taagtctttt   24000
agaatgaaag tcatttattt gcattatacc ataatcttta cttccattgt tattaacatt   24060
gactgcagat ttattaaatc cggattcttt ttccgcaatc gcttttaaca aacttgatgg   24120
aatattgtac ctttcaccag ccttatccca acaatcagct ctccctaaat atgggataaa   24180
acacagcaaa ataaatacga aacgggacat taataccccct tcattcttcg cgcaaattca   24240
tccttcagcc aacgcacacg cgaaatataa tattctgtat taacatatac atcctcgaat   24300
tcatttatcc cggtaagatc taatcgcgca attagatttc cgccttcatc atcagtagct   24360
aagcatatct tttctgagta attaggctc aacgcatata aagatcatt tatattttca   24420 ggcaatgcac aaaaagggca taataaattt attgaatctc cttctttttc aatatatatt   24480
agcacatcat catcaagcat gattgcttga tcatcgatat caattaaagg gatacccaag   24540
gctcggcaaa taacatctgc taaatcttcc atatattcct cttatacaaa tgacgaatac   24600
```

-continued

| | | | | | |
|---|---|---|---|---|---|
| cctttcacca | tattccatat | tttgggtcc | cctattcttt | cagaataaga | tagctctaac | 24660 |
| gaagatagcg | gcaattttt | catgactta | tttccgggca | caccagtatt | catctcttgg | 24720 |
| atttccatat | taccactatt | cattagaata | gtagaaaata | atcttttctc | ttctgaggat | 24780 |
| aatttactat | ttaattgaga | aaactgacct | gtttcatgtt | ttcttattat | ttctctttta | 24840 |
| atttcagcat | cctgcatacc | tgttctgtcc | ttcccactct | tacaattcca | gcaaggtaca | 24900 |
| gcacctatag | tataagccaa | tagagtcatt | ctttgtgaca | atttatacgg | ctctccatta | 24960 |
| tcattttt | gtaactttt | ggttacaatc | tcttttatct | ggttagccag | atatatcaca | 25020 |
| tcattcttac | atggtggatt | tttttctatt | gcttctgcag | cccaacctcc | aatcacacca | 25080 |
| tttttgagga | aattatcccc | caacaaagaa | catattgatt | catcattaag | cttgtcaaca | 25140 |
| ttcctccagc | ctaagcccat | ttttagcgct | aattcattta | caccaaagtt | aaatgtcacc | 25200 |
| actttagat | taacgcttac | ttctttcaga | agaccatcac | tattccgaat | taataatttc | 25260 |
| gttggctccc | ccctttaga | gtttaaccct | tttaatgcgt | tcacctgatc | ttttaacata | 25320 |
| ctctcctctc | ccccggttaa | actggtcggc | gtcagaagag | aagtcgaaac | aatctttaaa | 25380 |
| tctactgttt | taccagacaa | agcctgtgat | aataactctg | gtctgctata | taatgctgcg | 25440 |
| cttactaact | cctcagcttt | attacgagca | gcaacagctc | ttcagatga | gttttttc | 25500 |
| aatccatagg | ctgatataac | tccatgtctg | atacccgaaa | aaattcctt | ccctcatca | 25560 |
| tccaccactt | ttgaaagcca | catattcgcg | atatgatcac | tctctctcgt | agaagcacaa | 25620 |
| caaattcctt | ttccattata | ctctttgaca | aatatattt | tattccctat | cttcatatga | 25680 |
| gaggcaggag | ttaattgaaa | accataattt | ttcccatgat | gactaatatt | cttgtcgacc | 25740 |
| ggtccccaat | tcttattatt | taaataatca | gtaaatattt | gtttatttt | cgtttgcaat | 25800 |
| tcctttat | tttaatgcc | tagctgtgct | cttatctctt | cacttattac | tttattaagc | 25860 |
| tcattaatat | gtcttttatt | aacttcacca | agtttatagg | tatctaatcg | ttccatcatg | 25920 |
| gctttaattt | ttgacgtatc | accacctgcc | aactttattg | cctcgcaaaa | aacttcagct | 25980 |
| ctgtcacgcg | caaacaaaag | gctttttcct | gttaagcttg | tttggttctg | taaatataat | 26040 |
| cgattaagcg | cttcgatccc | cttatttctt | tctccatttt | taactctttg | atatgaaatc | 26100 |
| acgcttacac | ctttgtgctt | tccggtttct | tctgcgcctt | tataggaatc | tccgctttga | 26160 |
| aatgaaacct | gatgcaatcc | caaattagtt | atgtgcattt | aattatcctc | agtcataaat | 26220 |
| ggggcattga | ttgcagtttt | gtacctcgtt | ttacaacaaa | aaagatactt | attcaacagg | 26280 |
| gttctctctt | ttctataac | actccgagcc | tgatacatca | ggcactttat | cttgtgggat | 26340 |
| ttcatgatga | aacgagcact | acatatgctc | acgaggtaca | tattatgtac | agcaaaagaa | 26400 |
| aatttgatta | tgttaacagg | ctcaagtttc | taaatttatt | aattgaatat | attatatacc | 26460 |
| aaatacattt | tacatcccca | caatcaccaa | gtaatggaga | gttaataaag | tatgatcctc | 26520 |
| aaaattagca | atttcattga | cgcaagcaat | acaaaagggc | ctatacgcgt | tgaagataca | 26580 |
| gagcatggac | ctatattgat | agcacagaaa | ttcaacctaa | aggatctctt | tttcagaaca | 26640 |
| ttaagcacta | ttaatgcaaa | gataaattca | cagatattaa | atgaacaact | aaaaaattat | 26700 |
| cgactagaga | atcaaaaatc | cttattgctt | ttcctcaata | cattagctag | cgaaaaatct | 26760 |
| gcagaaagtg | cgtttgccgc | ctatgaagca | gctaaaaact | caattcaaca | ctctttcaca | 26820 |
| ggtagagaca | tcaaattaat | gttgaatacc | gcagagcgtt | tcatggcat | cggtacagcc | 26880 |
| aaaaatcttg | aaagacattt | agttttcgt | tgctggggaa | atagaggcat | aacccattta | 26940 |
| gggcatacta | gtatcagtat | aaaaaacaat | ttactacagg | aaccaactca | tacctatctc | 27000 |

```
agctggtatc ccggcgggaa tgttacaaaa gatacagaaa taaactacct ttttgaaaaa    27060
cgctcaggtt acagtgtcga tacctataag caagacaaac taaatatgat ttcagaccaa    27120
acagccgaaa gacttgatgc aggccaagag gttagaaact tattaaattc aaaacaagat    27180
caaaataaca acaaaaaaat attttttccc agagctaatc aaaaaaaaga cccctatggt    27240
tattgggggg tcagtgctga taaagtatac attccattat caggtgataa taaaacaaag    27300
gatggtaaaa tcagccataa cctttttggc cttgatgaaa caaacatgtc aaaatttata    27360
tgcaaaaaga aagcagatgc tttcagacaa ttggcaaatt ataaattaat cagtaaatct    27420
gaaaactgtg ctggtatggc acttaatgtt cttaaagcag gaaattctga aatatacttt    27480
ccactccctg acgttaaatt ggttgctaca cctaacgatg tatacgcgta tgcaaataaa    27540
gttaggcaac gcattgaaag tctcaatcag tcttataacg aaataatgaa gtatattgaa    27600
tctgattttg atcttttccag attgactcaa ttacgacgca gctatcttaa aagtttcaat    27660
aaaattaacc ttatccacac accaaaaaca ttcaagcctt tatcaatttc actttacaaa    27720
catcctactg aaaatgtatc ttcagaagac tttgatgcgg tcatcaacgc ttgccactca    27780
tacttagtaa aatcagcacc cagcaatatg actcgtgtat taaacgaatt aaaaaccgaa    27840
gcaacagata aaaagaaga aatcatcgaa aaatcaataa aaattattga ttattacaat    27900
tctcttaaat cgccagatct tggaaccaaa ctttacattc acgacttatt acagatcaat    27960
aagcttttat tgaataactc tcattctaat atatagaagg ccatagaaat gtgtcgcaaa    28020
ctatatgata aactttatga aataacaggt gcaaagcttg attttaacga taaaaatcaa    28080
gcctttatat tgctcgaaga acaaataccct gtttgtataa cagataatga tgaatacatc    28140
tttttgaccg gacttcttaa tgaacatgaa cttttttacag aaaatattat taatccagaa    28200
cacatactca tccttaacta ctctttgagt agagattatg gttcttctat ctgtcttctc    28260
cctgatactc atcaatgtgt tttgaccaag aaacactaca aaaaatatct ttcacctgat    28320
gaactcattg aatctttgta tgaattttta ttttgtatta aactaaccat tgcaaacatc    28380
acttcagaag tgaactaaca tatagggggt atcatgcaaa ttctaaacaa aatacttcca    28440
caggttgaat tcgcgattcc tcgcccatca tttgattcgt taagtcgcaa taagcttgta    28500
aagaaaatat tatctgtttt taacttaaaa caacgctttc ctcagaagaa ttttggatgc    28560
ccggtgaata taaataaaat cagggacagc gtcatagaca aaataaaaga tagtaattcg    28620
gggaatcaac tattttgttg gatgagccaa gagcgaacca cttatgtctc ttcaatgata    28680
aacagaagta tagatgaaat ggccatacac aatggagttg ttttgacctc agataacaaa    28740
aaaaacatat ttgcagctat tgaaaaaaaa ttcccggata taaaacttga tgaaaaatca    28800
gcacaaacat ctatcagtca tacagcacta acgagattg cctcatctgg cctcagagca    28860
aagattttaa aacgctatag cagtgacatg gatttgttta acacacaaat gaaggatctt    28920
acaaatctag tatccagttc cgtctacgat aaaaatatta tgaatcaac aaaagtttta    28980 caaatagaaa taagcgcaga ggttctaaag gctgtatacc gtcaaagcaa tacaaattaa    29040 atctttata ttaaatctta tacttattaa agtaaagcag acaaaaagga gaccttatgt    29100
ctttaaatat caccgaaaat gaaagcatct ctactgcagt aattgatgca attaactctg    29160
gcgctacact gaaagatatt aatgcaattc ctgatgatat gatggatgac atttattcat    29220
atgcttatga cttttacaac aaaggaagaa tagaggaagc tgaagttttc ttcaggtttt    29280
tatgtatata cgacttttac aatgtagact acattatggg actcgcagct atttatcaga    29340
```

```
taaaagaaca gttccaacaa gcagcagacc tttatgctgt cgcttttgca ttaggaaaaa    29400
atgactatac accagtattc catactggac aatgccagct tcggttgaaa gccccctta     29460 aagctaaaga gtgcttcgaa ctcgtaattc aacacagcaa tgatgaaaaa ttaaaaataa    29520
aagcacaatc atacttggac gcaattcagg atatcaagga gtaattatta tgcataatgt    29580
aagcaccaca accactggtt ttcctcttgc caaaatattg gcttccactg agcttggaga    29640
caatactatc caagctgcaa atgatgcagc taacaaatta ttttctctta caattgctga    29700
tcttactgct aaccaaaata ttaatacaac taatgcacac tcaacttcaa atatattaat    29760
ccctgaactt aaagcaccaa agtcattaaa tgcaagttcc caactaacgc ttttaattgg    29820
aaaccttatt caaatactcg gtgaaaaatc tttaactgca ttaacaaata aaattactgc    29880
ttggaagtcc cagcaacagg caagacagca aaaaaaccta gaattctccg ataaaattaa    29940
cactcttcta tctgaaactg aaggactaac cagagactat gaaaaacaaa ttaataaact    30000
aaaaaacgca gattctaaaa taaaagacct agaaaataaa attaaccaaa ttcaaacaag    30060
attatccgaa ctcgacccag agtcaccaga aaagaaaaaa ttaagccggg aagaaataca    30120
actcactatc aaaaaagacg cagcagttaa agacaggaca ttgattgagc agaaaaccct    30180
gtcaattcat agcaaactta cagataaatc aatgcaactc gaaaaagaaa tagactcttt    30240
ttctgcattt tcaaacacag catctgctga acagctatca acccagcaga aatcattaac    30300
cggacttgcc agtgttactc aattgatggc aacctttatt caactagttg gaaaaaataa    30360
tgaagaatct ttaaaaaatg atctggctct attccagtct ctccaagaat caagaaaaac    30420
tgaaatggag agaaaatctg atgagtatgc tgctgaagta cgtaaagcag aagaactcaa    30480
cagagtaatg ggttgtgttg ggaaaatact tggggcactt ttaactatcg ttagtgttgt    30540
tgcagcagct ttttctggag gagcctctct agcactggca gctgttggtt tagctcttat    30600
ggttacggat gctatagtac aagcagcgac cggcaattcc ttcatggaac aagccctgaa    30660
tccgatcatg aaagcagtca ttgaacccct aatcaaactc ctttcagatg catttacaaa    30720
aatgctcgaa ggcttgggcg tcgactcgaa aaaagccaaa atgattggct ctattctggg    30780
ggcaatcgca ggcgctcttg tcctagttgc agcagtcgtt ctcgtagcca ctgttggtaa    30840
acaggcagca gcaaaacttg cagaaaatat tggcaaaata ataggtaaaa ccctcacaga    30900
ccttatacca aagtttctca agaatttttc ttctcaactg gacgatttaa tcactaatgc    30960
tgttgccaga ttaaataaat ttcttggtgc agcgggtgat gaagtaatat ccaaacaaat    31020
tatttccacc catttaaacc aagcagtttt attaggagaa agtgttaact ctgccacaca    31080
agcgggagga agtgtcgctt ctgctgtttt ccagaacagc gcgtcgacaa atctagcaga    31140
cctgacatta tcgaaatatc aagttgaaca actgtcaaaa tatatcagtg aagcaataga    31200
aaaattcggc caattgcagg aagtaattgc agatctatta gcctcaatgt ccaactctca    31260
ggctaataga actgatgttg caaaagcaat tttgcaacaa actactgctt gatacaaata    31320
aggagaatgt tatggaaatt caaaacacaa aaccaaccca gatttatat acagatatat    31380 ccacaaaaca aactcaaagt tcttccgaaa cacaaaaatc acaaaattat cagcagattg    31440
cagcgcatat tccacttaat gtcggtaaaa atcccgtatt aacaaccaca ttaaatgatg    31500
atcaactttt aaagttatca gagcaggttc agcatgattc agaaatcatt gctcgcctta    31560
ctgacaaaaa gatgaaagat cttcagagat gagtcacac ccttactcca gagaacactc    31620
tggatatttc cagtctttct tctaatgctg tttcttttaat tattagtgta gccgttctac    31680
tttctgctct ccgcactgca gaaactaaat tgggctctca attgtcattg attgcgttcg    31740
```

```
atgctacaaa atcagctgca gagaacattg ttcggcaagg cctggcagcc ctatcatcaa   31800
gcattactgg agcagtcaca caagtaggta taacgggtat cggtgccaaa aaaacgcatt   31860
cagggattag cgaccaaaaa ggagccttaa gaaagaacct tgccactgct caatctcttg   31920
aaaaagagct tgcaggttct aaattagggt taaataaaca aatagataca aatatcacct   31980
caccacaaac taactctagc acaaaatttt taggtaaaaa taaactggcg ccagataata   32040
tatccctgtc aactgaacat aaaacttctc ttagttctcc cgatatttct ttgcaggata   32100
aaattgacac ccagagaaga acttacgagc tcaatacect ttctgcgcag caaaaacaaa   32160
acattggccg tgcaacaatg gaaacatcag ccgttgctgg taatatatcc acatcaggag   32220
ggcgttatgc atctgctctt gaagaagaag aacaactaat cagtcaggcc agcagtaaac   32280
aagcagagga agcatcccaa gtatctaaag aagcatccca agcgacaaat caattaatac   32340
aaaaattatt gaatataatt gacagcatca accaatcaaa gaattcgaca gccagtcaga   32400
ttgctggtaa cattcgagct taatatatcc aagagccata ataatatatg gctcttcctg   32460
taaggaaata accatgaata taacaactct gactaatagt atttccacct catcattcag   32520
tccaaacaat accaacggtt catcaaccga aacagttaat tctgatataa aaacaacgac   32580
cagttctcat cctgtaagtt cccttactat gctcaacgac acccttcata atatcagaac   32640
aacaaatcag gcattaaaga aagagctttc acaaaaaacg ttgactaaaa catcgctaga   32700
agaaatagca ttacattcat ctcagattag catggatgta aataaatccg ctcaactatt   32760
agatattctt tccaggcacg aatatccaat taataaagac gcaagagaat tattacattc   32820
agctccgaaa gaagccgagc ttgatggaga tcaaatgata tctcatagag aactgtgggc   32880
taaaattgca aactccatca atgatattaa tgaacagtat ctgaaagtat atgaacatgc   32940
cgttagttca tatactcaaa tgtatcaaga ttttagcgct gttctttcca gtcttgccgg   33000
ctggatctct cccggaggta acgacggaaa ctccgtgaaa ttacaagtca actcgcttaa   33060
aaaggcattg gaagaactca aggaaaaata taagataaa ccgctatatc cagcaaataa   33120
tactgttagt caggaacaag caaataaatg gcttacagaa ttaggtggaa caatcggcaa   33180
ggtatctcaa aaaacggggg gatatgttgt cagtataaac atgaccccaa tagacaatat   33240
gttaaaaagc ttagataatc taggtggaaa tggcgaggtt gtgctagata atgcaaaata   33300
tcaggcatgg aatgccggat tctctgccga agatgaaaca atgaaaaata atcttcaaac   33360
tttagttcaa aaatacagta atgccaatag tatttttgat aatttagtaa aggttttgag   33420
tagtacaata agctcatgta cagatacaga taaacttttt ctccatttct gaggtgcgcc   33480
atgcataatg taaataatac tcaagcgcca acattcttat ataaggcaac ttcaccatca   33540
tcaacagaat acagcgagtt aaaaagcaaa atatccgata tccatagttc gcaaacttct   33600
ctaaaaacac cagcatcagt gtctgaaaaa gaaaactttg caacgtcttt taatcagaaa   33660
tgtcttgatt ttttattttc ttcctcaggg aagaagatg tgttaagaag catttattcc   33720
aactcaatga atgcgtatgc caaaagcgag attctcgaat tttcaaatgt tttgtactcc   33780
ttagtacatc aaaatggtct taattttgaa aacgaaaagg gacttcaaaa aattgtcgca   33840
cagtattcgg aactaattat aaaagataaa ttatcccaag attctgcctt tggaccatgg   33900
tcggcaaaga ataagaaact ccatcaatta cgacaaaaca ttgagcacag acttgcacta   33960
ttagcacaac aacacacatc tggtgaagct ttatcattgg gacaaaaact cctcaatact   34020
gaagtatcat catttatcaa gaataatatt cttgctgaat taaagttaag taatgaaact   34080
```

-continued

```
gtttcatctc tcaaactaga tgatttagtt gacgcacagg caaaacttgc ctttgatagt   34140
ttgcgcaatc aacgtaaaaa tactattgat agtaaaggat ttggtatagg taaactgtca   34200
agagacttaa atacagtagc cgtgtttcct gagctgttga gaaaagtcct taatgatatt   34260
ttagaagata taaagattc gcatcctatc caagatggcc tccctacacc tcccgaagat    34320
atgccagatg gcggaccaac ccccggagcc aatgagaaaa catcccaacc tgtaattcac   34380
tatcatataa ataatgataa tagaacttac gataatagag tttttgacaa cagagtatat   34440
gacaatagct atcacgagaa cccagaaaat gatgcacagt ctcctacttc tcagacaaac   34500
gatctattat cccgtaacgg aaactcatta ctaaatccac aaagagcact agttcaaaaa   34560
gtaacttccg ttctaccaca ctctatatca gatactgtcc agacatttgc aaataattca   34620
gctttagaaa aggctttcaa ccatactcca gataattcgg atggaatagg ttcagacctg   34680
ttaactacga gtagtcaaga aagatctgca ataactctc tttctcgggg acacaggcct    34740
ctgaacatac agaactcttc aaccaccccc cctctccacc cggaaggagt gacaagcagt   34800
aatgataact catcagatac aactaaaagt agcgcttctc tttctcatag agtagcttcg   34860
caaatcaata aattcaactc aaacactgat tcaaaagtac ttcagactga ttttttatca    34920
agaaatggag acacatattt aacacgggaa acgatatttg aagcttcaaa aaaagtaaca   34980
aactccctaa gtaatcttat atctctcatt ggaactaaat caggaacaca agaacgagag   35040
ttacaggaaa aatcaaagga cattacaaaa tccacaacag aacatagaat aaacaacaaa   35100
ttaaaagtta cagatgcaaa tataagaaac tacgtaacag aaaccaacgc agatacaatt   35160
gataaaaatc atgcgatcta tgaaaaggca aagaagtat ctagcgccct cagcaaggta    35220
ttgtcaaaaa ttgacgatac ctctgcagaa ttacttacag atgatatatc tgatttaaaa   35280
aataacaatg atattacagc tgaaacaat aatatatata aagcagcaaa agatgtaacc    35340
acttccctat caaaagtatt aagaatatc aataaggatt aaaatatgat aaaagaaaaa    35400
atattatcaa tagtggcctt ttgctatggt atagcgtaca gcaaactatc tgaagaaact   35460
aaatttattg aagatctttc tgccgattct cttttctctga ttgaaatgct ggatatgatt   35520
agttttgagt tcaatctacg tatagatgaa tctacattag aacacattat tactattgga   35580
gatcttattt ctgtagtcaa aaatagtaca aaatcaatat agtaattgat aagcattttt   35640
tcatctatgg agctctcaca tcagagctcc acaagaatat tattcttta tccaataaag    35700 ataaattgca tcaatccagc tattaaaata gtaattttta agactaccgt tgactatcat   35760
caacagttac atacaatctt gctcacactg catttaactt ttgtcaatat aaatcaatat   35820
gaataaacag ggtgtgatat ggtggatttg tgcaacgact tgttaagtat aaaggaaggc   35880
caaaagaaag agtttacact ccattctggt aataaagttt cctttatcaa agccaagatt   35940
cctcataaaa ggatccaaga tttaaccttc gtcaaccaaa aaacgaatgt acgcgatcaa   36000
gaatccctaa cagaagaatc attagccgat atcataaaaa ctataaagct acaacaattc   36060
ttccctgtaa taggaaggga gattgatggt agaattgaaa ttctggatgg cactcgtaga   36120
agagcatctg caatatatgc aggagcagat cttgaagttc tatattcaaa agaatatata   36180
tctactcttg atgccagaaa actagcaaac gatatacaaa cagcaaaaga gcatagcatc   36240
cgagaacttg gtattggtct taattttctg aaagtatcag ggatgtccta taagacata    36300 gccaaaaaag agaatctgtc tcgcgcgaaa gtcactcgtg cctttcaggc agcaagcgtt   36360
ccacaggaaa taatatctct atttccaatc gcgtcagaac ttaactttaa tgactacaag   36420
atattattca attattataa aggacttgaa aaggctaatg aatctcttag ttctacacta   36480
```

```
ccaatattaa aggaagaaat aaaagacctt gatacaaatt tgcccccgga catatataaa   36540
aaagaaattt taaacatcat aaagaaaagc aaaaacagaa agcaaaaccc ttcgctaaaa   36600
gttgactcgt tatttatttc taaagacaaa cggacttaca taaaaagaaa agagaataaa   36660
acaaacagaa ctctaatatt tacattatct aaaataaaca aaacagttca gagagaaata   36720
gatgaagcta ttcgggatat aatttctcgc catctatcgt cttcataaac atcgaacact   36780
gatgtaaact gcccaattca gataataaaa atcttcgttg aacttgactt tcagccggtg   36840
gggtaattcc gtcggctatc tgttattcaa tccccacgca ctgtgtttcc ttaaaattac   36900
ggtgaaaact catacccctgc tgaccacgag aaaattatct ggtgaaatta gtaatattca   36960
tatcattgaa aatgaattgt gcaactaagg gatgcggcat gatggtcaaa attttatgtg   37020
aatatgagtg actggccgaa aatattcagc gtattttaa tcgtttcaat aaaaacagcg   37080
aggattagca gtcaacgctt ttactactca attttttta catggtgata aacaaaaaat   37140
ccaccattaa cagacttcgt tcacagtatc aaaaagctt taagaatata ttagcagatt   37200
tctcaaatat aattactgtt ttattctcct aatcttccca taaaatgacc gacttacatt   37260
attttataat tataaacaag tttgatttta aaatcatatt aattattaac aagagattta   37320 ttttctaac cccaaaagtt atgcttggtc aaagagtaac ttataatatc catcccctc    37380 ataggggctta cagtttaaat tgcgggtata aaatacatct atttcaaat aaaataaagc   37440 atactccaat tacaacgagt gactaaaata aaaatatcat ccaagtcaat cactgtttgc   37500
tctgcaaaat atgtcagcct tctcaaactt accagcactt aaatatttaa gcacacaatc   37560
attccttgag ggagttcact tatttcaaga gaaacatttc gtcttcccac acaactaatc   37620
cgcccaatat agctaaattt gtactcagta atatcatttg ttatgccccc cacccaaaa    37680 tattcaagct ccttcacaga taaaaaacga caatttacaa agcctcatta gttataacta   37740
tggaaatacc tattttagta tatcctataa agttagaatt acttcttctt gcacctaatt   37800
ccatagttga aaaacaagaa taatttctc ctacagctgg atccatatag cttccatcag    37860
gtctacacaa cacccagtgg aggccgacag gaactccaat aaaggataca gcaacagctt   37920
ccaaaactct ttggttagaa gataacacat ctcgttgatg tactatatta catcccatgc   37980
caattaataa gtcccttgca tcgggataaa taaaactaat tacttgcgaa aaaatgttac   38040
tttcttcaac gacataagca ttcaatccaa gaagcctcgt agccatgact atcttatcag   38100
gcatagaata accggcatcc gcgatattat ctttgtgtat tctcggatta taattaccac   38160
tagttattaa gtataaatcc cgctcacaac gattatccaa atcaagagaa ctcttccttg   38220
tcatttcgga catagaccct ttgtattgtg gtattttatc aaccctaat tcctttgcag     38280 cacagagtaa actggcagct ccacaagaat tgtcatacat ctgcttcctc gccaaaaac    38340 aaccttgttc gtttactcta ttctcattta ccctcacatc agtctgatga gatatcatat   38400
attctcttgg tatagcccc tgcaataaaa cccatataa cataacacct gtatgaatac     38460
atccccgttt gcaaggcttc cgttgttccg acatcgacga gtaattgcag cacagtattg   38520
catccagcaa tgcgaactac tatgagaatt agctgaccgg gtccttattc cccgaacgaa   38580
ctttaaatcc aaaacctcat actctttcc gtcgtcatca cgtccgtcac cataacaacc    38640
tttcagcatc caccctttta ttaagagtta atgtccatca gcatcagcaa ttaataccgc   38700
ctgatactga catattttg tcgtatttac gtccataatc ggttattgtg atacaggtca    38760
caccagctta tttgctattg ttacaataac caccttggtt gagagctgtt ttttcaactt   38820
```

```
tgttatcaac tcccccaact ccttggtcag taaggctgcc gaccgagcac agtgaataga    38880
tagtatccgc aggtaccacc atgcttactt aatactcaga aggcgaacat atgaatatcc    38940
tccttagttc ctattccgaa gttcctattc tctagaaagt ataggaactt cgaagcagct    39000
ccagcctaca cggcccgggc ggccgctcag ctccagtctt cagttctcag gccgcccaca    39060
cgttcaaatt cccgggtgtt attagtcaca ataatcagcc cccgactgcg ggcatgacct    39120
gcgatcattt gatcaaatgg cccgacaggg cgtccctgac gggcaagttc tgctcttatc    39180
tggccggtgt gtgtggctgc agcagcgtcg taatccagaa catcaatgcg ggaaacaaat    39240
ccctcgatca cagcgagatt acgttcaggc atctggcttt tttctgcacc atatatcagc    39300
tccatcaggg tgaccgaact gatacacatt ttcccctggt tcaggttaaa acgctccctg    39360
acgctggcgg gtttgttctt tatcgtaaaa atgcagatgt tggtatcgag cataaacttc    39420
agcatcagaa tgactccctt tcttgcatgc cgggctgttc cctgttatcc ataaaatcgg    39480
tgctgacgct gtgtccgtcg aaccattcgt cccatgtctc tccggctggc gtaatgattc    39540
tggttcgtcc gacagcaatc acttcaacgc gttttacgtt ttccggcaat gcaaccgctt    39600
ttggcagtct gaccgcctgg ctgcggttgc tgagaaatac ggtggtttcc attatttgcc    39660
tccttatgtg gatatgtctt gtgtatatct attgtgggat tgatacccta ggcctattaa    39720
tattccggag tatacgtagc cggctaacgt taacaaccgc gatcgcacat gtacatgatc    39780
aacaacaggt accttaaaat ttttatgat ataagtaaaa tttctttgga gttataccat    39840
aatattcatt aaatttcctt ataaaataag atgggcttga tattccgata agtcttgata    39900
catcattaat atagctttga ctattcaata aaagctttgc tgcatgatgc atgcgaatat    39960
caagaaggat ttgttgaaat gttaatttt cactctccaa tcgttttcta acagctattt    40020
ctgataaatt caagttattt gaaatatcag aaagacgcca tctcttctcg atgttttttt    40080
caacaatctt ccttatctga tcagaaaaac taagagaaga agctatcgat atcgaagtat    40140
ataaagcttc ctcatcagaa acagctgata aaaggcaagc taaactatag atctttcttt    40200
tgccgaaagg catctctttt atagatttga acaaatcgat agaaacctcc tcctcagaga    40260
ggaggaatat tttttgttt aaccccctt tctcctcaga ataggagtgt tgaaatgaat    40320
aaattggttc cattattcta ataatgctta ataataaatt tctgtcaagg cttataatct    40380
caaatggatt aatgctatca gatttttta tggagacgtt tatttgtata tttcgctcta    40440
taaaagcaat ttgcccttca tcgatagtca aagtttcatt gcctgagcta accgtcattg    40500 aacaccttt tgcatataaa ataatatagt tatgcaagcg aacctttata tctattttgt    40560
ttttatgtcc catatccatc ataaattcaa cagaatatac caaactatat ttagtgttta    40620
cagagtaact aagaaatttc tgtaacagtg attgtataca aaatctttcc gttattaaga    40680
tagattaagt aattttcct atatttaact ttatttacat ttttgaaga aagagcttat    40740 gcagcttcta tttctctgtg caacaagcta agtatttgca ctgaaaggga ctataaccat    40800
attatggttt cacttttctt aggcaatatc tgtgtaaatg ttcggaaagg agtggagctt    40860
cgcaaaactc cagcatcata atatcctata cggaacgcat aaagcccctt cagactggag    40920
gctccacaaa tccggttggt gttgatattg gtaagcgtta accgaatgcc gcattgacga    40980
ttctcccgat gacagcgtt                                                40999
```

<210> SEQ ID NO 2
<211> LENGTH: 45646
<212> TYPE: DNA
<213> ORGANISM: Artificial Sequence
<220> FEATURE:
<223> OTHER INFORMATION: Recombinant Plasmid

<400> SEQUENCE: 2

```
gctagcatgc gcaaatttaa agcgctgata tcgatcgcgc gccctgcagg taccgttcgt      60
atagcataca ttatacgaag ttattgatcg cacgtaaga ggttccaact ttcaccataa      120
tgaaataaga tcactaccgg gcgtattttt tgagttgtcg agattttcag gagctaagga     180
agctaaaatg gagaaaaaaa tcactggata taccaccgtt gatatatccc aatggcatcg     240
taaagaacat tttgaggcat ttcagtcagt tgctcaatgt acctataacc agaccgttca     300
gctggatatt acggcctttt taaagaccgt aaagaaaaat aagcacaagt tttatccggc     360
ctttattcac attcttgccc gcctgatgaa tgctcatccg gaattacgta tggcaatgaa    420
agacggtgag ctggtgatat gggatagtgt tcacccttgt tacaccgttt tccatgagca    480
aactgaaacg ttttcatcgc tctggagtga ataccacgac gatttccggc agtttctaca    540
catatattcg caagatgtgg cgtgttacgg tgaaaacctg gcctatttcc ctaaagggtt    600
tattgagaat atgttttttcg tctcagccaa tccctgggtg agtttcacca gttttgattt    660
aaacgtggcc aatatggaca acttcttcgc ccccgttttc accatgggca atatattatac   720
gcaaggcgac aaggtgctga tgccgctggc gattcaggtt catcatgccg tttgtgatgg    780
cttccatgtc ggcagatgct taatgaatac aacagtactg cgatgaataa cttcgtataa    840
tgtatgctat acgaacggta cctgcagggt catgatgatc attgcaattg gatccaagca    900
ctaccccgc ctgttgcgac agtcacgtca tcgccgtccg ttaccggaac atgtttcccg     960
cgaaatacac catctggagc ctgaagaaag ctgttgtccg gagtgtggtg gtgaactgga   1020
ttattcgggg gaaatcagcg tctttctccc ggaaaggcat actatcttac agtaatattc   1080
attccgatga ttaataaatc agcaatgcgc gcatttttaa tataagcatg tacaatatgt   1140
acttgcatgc attccctgc taatgcagtt tttttgtaa taagttaaaa tcctacatag    1200
cacggagggg gaatgactag ttttgagcag ttaagtaagg ttgcgcagcg tgcagataaa   1260
atgttgctcg ccctaacaaa acagattcag gagcaaaagc aggagtttca ggctgatgtt   1320
ttttatcaag tctattcaaa gtctgctgta gctaagcttc caaaattaac gcgcgcaagc   1380
gtggatggtg cagtcggtga gatggaggct cagggctatc agtttgaaaa acgcccagca   1440
ggaaccgcga caaatatgc attaaccatc cagaacatta tcgatatcta tgcacatcgt   1500
ggcattccta aatatcgcga tcgttatagt gaggcatatt ccatattcat cggtagtcta   1560
aaaggcggtg tgtctaaaac cgtgagtagt gtttccgtag ctcacgccct gcgtgctcat   1620
cctcacctgc tgtcagaaga tttacgtatt ctgctccttg atttagatcc ccagtcatca   1680
gccactatgt ttctgaacta cttgcatgcg gtggggctgg ttgatacaac cgcaccgcag   1740
gctatgttgc agaacgtgag tcgtgaggaa ttactggaag attttatcgt tccgtcagtt   1800
atccctggcg tttatgttat gccggcttct attgacgacg cctttattgc atcaaactgg   1860
gatactctgt gcgaggagca tctattagga caaacaaac acgcgatatt gcgtgagaat   1920
attattgata agctgaagca tgatttcgac ttcatcctta ttgatacagg cccgcatctg   1980
gacgcatttt tgaaaaatgc cattgctgcc gcagatatca tgtttacacc ggtgccgcca   2040
gcacaagttg atttccattc cacgcttaaa tatttggctc gtttacctga acttgtacag   2100
attattgaac aggatggatg ttcatgccgt ttgcaggcaa atattggctt catgtcgaaa   2160
ctggcgaata agtcagatca taaatactgc catagcctga caaaagagat tttcggtggt   2220
```

-continued

```
gacatgcttg atgtttcaat gccacgtctt gatggttttg agagaagcgg cgagtcgttt    2280
gataccgtga tatctgcgaa tcctgttact tatgttggca gtggtgaagc tttgaaaaat    2340
gcacgtatgg cagcagaaga tttcgctaaa gcagttttg atcgtattga atttataagg     2400
gccaactact gatggaaaac agaaagcacc gaccgactat tggccgtacg ctgaatacaa    2460
atatcctgaa taatactgaa gaaatatcgg ctccagttca tgtatttacc ctcaatactg    2520
gccgaaaggc aaaatttact gagatcaagg ttgatcatga caaagtggat actcaaactt    2580
ttgtggttga agaggtgaat ggccgcgaac agacagccct gacgccggac tcactaaaag    2640
acatcaccag aactatacgt ttacaacaat tctatccatg tatttggatt cggactggcg    2700
atcttattga gattttggat ggttcccgtc gtcgggcagc agctttgcta tgcaaggttg    2760
gattacgtgt acttgtaacg gatgatgagc ttactgtttc tgaagctcag catctggcga    2820
aagatttgca gacgtcactt gaacataata ttcgtgaaat tggttgcgt ttagtacgtc     2880
tcaaagaggc cggtatgaac cagaagcaaa ttgcggaaag agagggattg tcggcagcta    2940
aggtgactcg tgccctccaa gcagcgtccg tacctaaaga ttttgtgtct ctttttcctg    3000
ttcagtctga gctgacatac gccgattaca ggcaactggc tgaattaagt gaacgactga    3060
ggctgggtga tatatctatt gatgaagttg tgaagaatat ctcgccgagt attgagctta    3120
ttactgctga tgacaatctt tctgaagacg aggttaaaaa cagtattatg cggcttataa    3180
ccaaggaaat gtcttcattg cttgattcag gagtaaagga taaagcggtt gtaactttgt    3240
tatggaaatt tgatagtaaa gataaatttg ctcgaaaacg agtaaaggga cgtacgttct    3300
catatgaatt cggcagatta ccgttggaag ttcaggataa gttagatcgt atgattgctc    3360
ttgtactaaa agataatctg aattcgctgt gaaaattcaa gttttcgcc agcaactcgc     3420
cagttttaa ttggctgttt taaagaaat tttgcttta ttagcgtttt ttttgaacag       3480
tatttcacgg tgaaatcgcc tgtttcaccg tatcttcttt gcttgaaaaa gatagtttct    3540
cttagccgtt taacagtaac cgatgagata gtcttccccc tctttcacgg cagccttcaa    3600
ttgcgccatg atggataaac tttaacaaca aaagtaagcg ggataccatg tctgaacaga    3660
aaatcaccgg cggatccata tagggccc gggttataat tacctcaggt cgacgtccca     3720
tggccattcg aattcgccct tatgcaatga atcaatcaga gccatccagt ttaatcgtcg    3780
gttccgttca tatggagcaa aagtggtgtt gaagaaacat ccgttttgtg tgttttttt    3840
aatcttttg gggttttaat tcctatcgct caagtcttaa cgatatccct gaaacgacca    3900
cttaatatta ctcacacttt tgcaaatgca ttaaatgctg cttgtattat tctgatgccg    3960
caccagcggc atggaaggcg gcacgctgtg gttacatgtg ataccggagt aaaaccgccg    4020
aagcccggcg tcagcggta ctgattgaca gatttcacct tacccatccc cagccctgcc     4080
aagccatacc cgttttcagc catgatagag cttctgtgcg cggtcggagt ggtcccgacg    4140
agggttttac ccgaagtcgg ggcgtatctc cgcgttagcg ggccgtgagg gccgcttacg    4200
agcgtgtatt cgatacgtcc agccagaaga ctgacagcga tgatgatgta gttacaacat    4260
tcacaattaa aagcgactct gttcccgccc tttgggcggg gcggcggcg cttttcagtt     4320
atgaggggg cgttgtggtt tcagttttgc gttggacttg gtttttttag gggtttatgt     4380
ttgcatgttg taactaaacc ggcttcggtt ggggccccgc cgcttgcggt gggaggtgca    4440
tatttgtctg tccacaggac aggcagtgaa caggttttct ttttaaatga atgtaattaa    4500
gtagtttaaa ggagatataa acaggtgttt aaaagataca ttgcaccctg tagggttgac    4560
gtctggcgct ttatgacgtg aacggttgta accttatggt gaagtccctt gcagtttaat    4620
```

```
gtggataagc aaaattcccc gtctgtgagg cgtgttttgt atcaaaaaca gggggggaccg    4680 gatgcacctg aaggtggatg atgaggttgt tttttgtatg tagcgctgat ttttgtgca      4740 ctggcgggct tcaggcgtgc gaatgcctcc ggcgcgtgcc ggattattct gaggaggtca    4800 cttcagggg gaagctgtgg ccagccggct gtaattacgg ttacgtgaca gaatcatgcg      4860
ctccttcaca cgacgctcca cttcacgttt taccgcctca cgactggcag tgaagcgccc    4920
ttccgagatt tcacgcgtca gttgccgttt caccagggtg acaatatcct gacgctgcct    4980
gtccgcatca cgacgcgcac gggcacgctt cattccacgg gacttaagct ctgtctggta    5040
actgcggaaa cgctcacgaa caaaacgcca ggctttcgcc atcagttcat ccatacccag    5100
ggtatccagc ccctgctttt tgcgctgtct gttttcccat tccacacgac tgcggcgcgc    5160
ggcggccact gcctcctctg atacatcgag ggcagcaaac agtgcagatg tgaacgtgat    5220
atcggtcgga atgtagcacc cgataagcgg gtcatattcc gtctggtagg taatcagtcc    5280
cagctctgca aggaacgtca gggcccgggt ggcccgggtg atggagagtt ttccggcagc    5340
agactccgtc gccagtccgc actcaatggc cagcgtggtg atggaacact ggacgcggtt    5400
ggccagtggg tcatagtgaa aacacagccc ctgcagcagc gcatcaatgg cccggcgacg    5460
tagtaccggt ggcatgcgcc gacgcagacc aagcgaacgg gcatgtgcca catgaatggc    5520
gaaatcaaaa cggaggtga agcccaccgc ttttccatc agtttcccgc agaacggaag     5580
cgtccgggca ccttcacggg gtgtgaacac cggattcggg ttctttacct ggcggtaata    5640
agtttgttga agatcagtca caccatcctg cacttacaat gcgcagaagg agcgagcaca    5700
gaaagaagtc ttgaactttt ccgggcatat aactatactc cccgcatagc ttgattgttg    5760
gctgtacggt ttaagtgggc cccggtaatc tttctgactc gccaaagtta aagaagatta    5820
tcggggtttt tgcttttctg gctcctgtac atccacatca gaaccagttc cctgccacct    5880
tatggcgtgg ccagccataa aattccttaa acgatcagta atctagcatg ctacgccaca    5940
aagtaaagtc tttactttag tatatccagt ctctgcagtt catctttgat gattttctca    6000
acgaactgag cctgtgttat cccctctctc tcgcagtact caaccatgag atctttcaga    6060 ggattttga caaaaacttt tatctctttg tgtgtaagac gttttcttgc aacagcggcc    6120
agttgtttct cagagtcagt cataggctta cctctgcgca caaaccgctt ttgactcaat    6180
gaggaagtca ctgcattttc tgtctgcgac atctcgcctc ctcaatactc aaacagggat    6240
cgtttcgcag aggatactat tgcataaggg cgaattctag ctcactcatt aggcacccca    6300
ggctttacac tttatgcttc cggctcgtat gttgtgtgga attgtgagcg gataacaatt    6360
tcacacagga aacagctatg accatgatta cgccaagctt aaggtgcacg gcccacgtgg    6420
ccactagtac ttctcgagct cacatgtgtt taaactgtac atgtggcgcg ccacatgtca    6480
tggccggccc caatataata ttggcttaaa catcaggaga tatgatggca aatgatactt    6540
gacgactttc tggagggata gcattgcgaa gcccttcact gcttggaagt gttccagcat    6600
gaacgagata gcttgtttct atttattaa taccaacacc attacatgtt atgtgcgatg    6660
gtaatattga tgagctaact tcgtaagccc tccccccaga ggcagagatt gcagtgtcgt    6720
ttttagggac aactgcgttg attttttataa tatgtccaca attgttaata actcgttgtt    6780
caggcatgaa attaagcctg ttttctatgt tttcggacat aatttgggca tatatgtgtt    6840
ccacagagga agacgtgatg tgaagagatt gccagaatgc agatgttagt gcagatataa    6900
atgcagggtc ttgaaagagt gaagtaaaca aaagtttttc tgtttgaaaa cataggtctt    6960
```

```
gttgggggaa gtttgaattg attattttat ttacttggtt gtaacttagc atttgaagct    7020
cttttttgct atcaatgaat tcattaattc ctaactcatt aattagatct gcaattaatt    7080
ttagtggtat ttcaatattg ttgaaatata tttttgtact attgctgtca gatgctcgaa    7140
tatctctgta aatatcatgc caaacactat taaaatcagt gtctttaacg tggaagtaat    7200
catcgtttgg tattatcgat gtacagcaat taatggctgt ttcaataact tctggtgcag    7260
gcttgtgagt tttaaaattc cctgataccg gagctgtaat agtatgtact tttcctaagt    7320
tgaattgttt ggggggagt gaacttaaca agttattata ttcttttgat gaaagttgag     7380
tggattgtat tttatctcca tcaagataaa aaaccgaaca tatgcctttg ttaaggcata    7440
gccgtattga aatgccatct atgtttgcgt gggcaaactc tccgtccatt ttatcttgtg    7500
atagtgatgg tgagaaacta tccattagtt ttttttcgct atgtttttcg gctagagttt    7560
cgtgtggaga atatatgccg aaagttatta ttttcagtaa aatgtcacaa aaactcaatt    7620
tattccaact tacttctgta gttgattga cagttgacat ccatgatgag tcatttctt      7680
catggttagt tatgtttgat gtctgcattt gatttctcct gatgtatttt cctattaatg    7740
ccaatatata ttaatataat taaattggga acataataaa atggaatgtt attcttctct    7800
ttaagaaaac gatacatttc cactaaaaac aattatgcag ttattgcatt ggagagtctg    7860
gtaggaaagt tgtgatatga atacattcat gttattggct ttggggatta acatcaaggg    7920
gcagatagaa ccattgggtg tatagaaaaa caaagtggtt aaactttggg caagcgtaca    7980
gaaagaactg aaaagttgcg gtctgaagca gactatcata gtaaaattat taatttatta    8040
tcgaacatat agctttcccc ctcttttttt caaagcaaga cacaggtaaa tttctcccgt    8100
tgcattgata tataacacag ctctcatgtt ttggttgagg ctttgtttaa tatgttttg     8160
catatatcgt cccttattc cggataaaac ggaatctttt caggggttta tcaaccactt     8220
actgataata tagtgcatga atcaaattca caaattttt tgtaatatga cccaatgttc     8280
acagggggg gccggagaat tacctacggt aaaggaaaaa acatgcaaat tgtctttttc     8340
tccttttgtt gttggtgcat ccctgttgct cggggggcca atagcttttg ctactcctct    8400
ttcgggtact caagaacttc attttttcaga ggacaattat gaaaaattat taacacctgt   8460
tgatggactt tctcccttgg gagctggtga agatggaatg gatgcgtggt atataacttc    8520
ttccaacccc tctcatgcat ctagaactaa gctacggatt aactctgata ttatgattag    8580
cgcaggtcat ggtggtgctg gtgataataa tgatggtaat agttgtggcg gtaatggtgg    8640
tgactctatt accggatctg acttgtctat aatcaatcaa gcatgattc ttggtggtag     8700
cggcggtagc ggtgctgacc ataacggtga tggtggtgag gctgttacag agacaatct     8760
gtttataata aatggagaaa ttatttcagg tggacatggt ggcgatagtt atagtgatag    8820
tgatgggggg aatggaggtg atgccgtcac aggagtcaat ttacccataa tcaacaaagg    8880
gactatttcc ggtggtaatg gaggtaacaa ttatggtgag ggtgatggcg gtaatggagg    8940
tgatgccatc acaggaagca gcctctctgt aatcaataag ggcacgttcg ctggaggcaa    9000
cggaggtgct gcttacggtt atggttatga tggctacggt ggtaatgcta tcacaggaga    9060
taacctgtct gtaatcaaca atggagctat tttaggcgt aatggtggac attgggggga     9120
tgctataaat ggtagcaata tgaccattgc taatagcgga tatataattt caggtaaaga    9180
agatgatgga acacaaaatg tagcaggtaa tgctatccac atcactggtg aaacaattc     9240
attaatactc catgaaggtt ctgtcattac tggtgatgta caggttaaca attcatccat    9300
tctgaaaatt atcaacaatg attacactgg gaccacacca actattgaag gtgatttatg    9360
```

```
tgctggtgat tgtacaactg tttcactatc aggtaacaaa ttcactgttt caggtgacgt    9420
ttcttttggt gagaacagtt ctttaaattt agctggaatc agtagtctgg aagcttctgg    9480
aaatatgtca tttggcaaca atgtaaaagt ggaggctatt ataaataact gggcgcagaa    9540
ggactataaa ctgctaagtg cagataaagg gataacaggt ttcagtgttt ctaatatatc    9600
tatcatcaat ccgttactca ctactggtgc tattgactat acaaaaagct atatcagtga    9660
ccagaataaa ttgatctacg gtttgagctg gaatgataca gatggcgaca gtcatggaga    9720
gttcaatctg aaagaaaacg ctgaacttac tgttagtact attctggcag ataatctcag    9780
ccatcataat ataaatagct gggacggaaa atccctaaca aaatcagggg agggaactct    9840
cattttggcg gaaaaaaata cctactctgg tttcaccaac atcaatgcag gcattctaaa    9900
aatggggaca gttgaagcta tgacacgtac cgctggtgtt attgttaata aaggtgctac    9960
cttgaatttt tcaggcatga accaaactgt taacacttta ttaaatagtg ggactgtgct   10020
aatcaataat attaatgccc cttttttgcc tgaccccgtc attgtcacag gtaacatgac   10080
tctggagaaa aacggtcatg ttattctcaa taatagttcg tcaaatgtcg gtcagaccta   10140
tgttcagaaa ggtaattggc atggaaaggg cggaatatta tctttgggcg cggttctcgg   10200
caatgacaac agtaaaactg accggctgga aattgcaggc catgcgtctg gtattaccta   10260
tgttgcagtg acaaatgagg gaggctctgg agataaaact cttgaaggtg ttcaaattat   10320
ttcgacagat tcttctgata agaatgcttt tattcagaaa ggccgtattg ttgctggtag   10380
ttatgactat cgcctgaaac agggcactgt atctggactg aataccaata agtggtatct   10440
aactagtcag atggataatc aagaatcaaa acagatgagc aatcaagagt ctactcaaat   10500
gagtagtcgc cgagctagtt cacagcttgt atcttcactt aatttgggtg aaggtagtat   10560
tcacacatgg cgccctgaag ctggcagtta tattgctaac ctgatagcaa tgaacacgat   10620
gtttagtcct tctctctatg accgacacgg tagcactatt gttgatccta ctacaggtca   10680
gctcagcgaa accaccatgt ggattcgtac tgttggtgga cataatgagc ataatttagc   10740
tgatagacaa ttaaaaacca cagctaacag gatggtttat cagattggtg gagatatttt   10800
gaagacaaac ttcactgatc atgatggctt gcatgtgggt attatgggag cttatggata   10860
tcaggatagc aaaactcata ataagtatac tagttatagt tcacgaggaa ctgtgagcgg   10920
ttatactgcc ggtttgtaca gttcttggtt tcaggatgaa aaagaacgaa caggtctata   10980
tatggatgct tggttgcagt acagttggtt taataataca gtcaaaggag atgggttaac   11040
tggtgagaaa tattccagca aaggaataac aggagctttg gaagctggct atatctaccc   11100
aaccatacgc tggactgctc ataataatat tgacaacgca ttgtatctca atccacaagt   11160
ccagataact aggcatgggg taaaagcaaa cgactatatt gaacacaatg gcactatggt   11220
cacatcctct gggggcaata atattcaagc aaaattggga ttgcgtacat ccttaattag   11280
tcagagttgt atcgataagg agactcttcg taagttcgaa ccattttggg aagtgaattg   11340
gaaatggagc tcaaagcaat atggtgtaat tatgaatggc atgtcaaatc accagatagg   11400
caaccgtaat gtgattgaac tcaaaactgg tgtgggggggg cgtcttgcag ataacctaag   11460
catctgggga aacgtatctc agcaattggg taataacagt tacagagaca cccaaggtat   11520
tttgggtgtg aaatatacct tctgataata aaaatgcagg gcgtgttgat gtcctgcatt   11580
tctcggtccg accaggtcac attcagatga aatcttctg agtaaaacat ttattatatc   11640
cttattgcta aggaaagata ttgggttcaa tacctcatta gcaatggagt taatgatgga   11700
```

```
agattctatt tcaaattcag actgatcaat acctatttta ttacagaaat taactcccat    11760
ataacacatc tcctttactt attaatgagt gttttcaacc tgctcaagcc aaacaataag    11820
acgtaggact tcatccaagt gttcaaaatc aacaaaacta tattttgtat gtgttttata    11880
tagttttcta gctaatttca catcacgcac agtcggtata ccaacttcat ttgcatattt    11940
tctgacagcc aaggcacact ggttagtttc aatgagagaa ataaaaggtg caggcgctat    12000
ttctggatta aaataaatac caattgcaat atgagtcggg ttcattacca ctaattttga    12060
attacgtata tcagatttag tctgctctga aagaatctcg atatgcaact cacgccttct    12120
cgactttgtc tcaaagtgtc cctcttgctc tatatattct cttttatct cctgtttatc    12180 catcatcata tctttcatgt ataaaatgaa ctcaatcaca aagtcaagaa taataacaag    12240
aatagaaaat gccaagaaaa ataatattat atccttaaac agcctccccc aaataagata    12300
taagccatca acactagaaa acacctgaga aaaaattatt tttcggtcat taatccaaaa    12360
gaaataggtt gttaatgcta gaataataag aagcagaatg cttttgaaaa attcttttat    12420
tgtctttata ctaaatattt tttttaaccc tttaacaggg tttaatactg aaaaatcaat    12480
cttgatagct ttagtcgcaa gaacaaactt tgtttgaacc aatgttggca acacagccga    12540
aagaacacag aaaaaaagtg ggaagccaat tatcttaaaa aagacaataa ccactgcaaa    12600
aaagtattta ccctcattaa tttcgaagtc attaattatt acatatctgt ataagagcat    12660
tacatcactt aaggaaaaga atgatattat agtaaatgtc cctaccagaa taataacaac    12720
agtcgttaaa tccttaaatt taaatgactg tcctttttt gcggcatcct ttagtttttt    12780
aggtgtcggc ttttctgttt tatttgccat aatatttat ctaacaaata gatttgtgaa    12840
aaatttatgt tcaccgagga aaaattgaac tttagaaaag taaatagtag aagaacagat    12900
gaaaataata aatattgcaa gtaaactttt aatagttaat gatacggaaa aagcattcat    12960
ctgcggagca aatctcgata atacaccaag taatacttct gatagtaaca atactatcat    13020
aacaggactg gctaaaataa cagcctgact tgccaataaa gtcagaaatg ttaagatatt    13080
tgagacacgg aaagaacatt gagaaaataa cgggcatata ttataagaca attgtatgga    13140
ttctaaaata aagaccatac caccactgta tagaaataca actgcagaaa aaagattgaa    13200
aaattttgcc aactcagacg tatcaacacc attggcagga tcaattgaac tactaagcgt    13260
tgccccgcgc tggttgtcaa taatgctacc aacagcatga aatatccaaa agggaagaga    13320
caagcaaaaa gagagaagga ggccaacaat tatttccttg aacataagga aataaacatg    13380
ttcaaaaaca gaagaaccta tgtctaccct accagaagta attaatcctg atgcaacaag    13440
aaaaatcaca ggtattctaa tagatggaga aattataccg ttatttaaaa atggaagaaa    13500
gaaaaataat ggagccaatc taaaaaaaac gccgttcagg agtattaaaa acacatgaat    13560
actttcgaac cagcttgaaa tgtccatcaa accccactct taattaaaaa cattatttca    13620
tgacaaaaag acaataaaac ctcaccatac catccagaaa gaagtagcaa agatattgag    13680
acacctataa gctttatacc aaaaggaagt gtctgctctt ggagttgagt cactgtctgt    13740
aacaaaccaa tagataatcc aataaccgta gctatacctta ctggccataa ggaaaagata    13800
aggattaaat aaagagcctt attacccata taaactatat cagacacatt acctccatca    13860
tctaagcagg aatattgata tattgttcaa tcaaggcctt agacaggata ccccacccat    13920
caagcgcaac aaataataca agttttattg gtactgatat tgtgattgga ctcatcatca    13980
tcataccaag tgcaagtaaa atgcttgaaa taacaagatc aacaacaaca aatggcaaat    14040
ataaataaaa acctattttg aacgcatctt tgatttcact tagcgcatat gcaggcaaga    14100
```

```
gggaaaacaa tgaataatca ttattctctg cactctttaa atcagcattt tcttcttcag   14160
acctttggaa aaacgtgct aactcaagat ctgtatgctt tttcaagtat tgcttatatt   14220
ccatcaagcc agaatcagaa aaacggacaa tatcagatat tgtatcaaat ttttgagggc   14280
catttagata attttcataa ccagcttcaa taatgggttt catcacgaac aaagccataa   14340
tcaatgcaat accattgaga gtcatatttg atggaacctg ctgcaaacca agtgcatttc   14400
gtaccattac aaaacaata gaaaacttta tataacaggt accagcagca actaaaaatg   14460
gtaatagcgt aaaaaagaa agtgtagcga tgagggacat gtcactcagc atgagattac   14520
tcctttacca tccaagaact aatctcgata ccataaccat cctcaataga aacaagttcc   14580
ccatgcccaa ccaaagaacc atttacttta atatttacat gtttaactat gtcatcggga   14640
aacttgaata attcgttttc tacatacatt tttagttcat tgattgtcat attttttct   14700 aaaagaataa agtccacttt tacattgata tcatcataat tgaataatgc caaagaaact   14760
tctgtgtgtt ctgactcacc attactttct gacagattaa tttttgcctc attattatca   14820
ttcacaatat aatccccaat aataacttga ttacacaata ataaattata agtttctga   14880 actatgatta tatcaccagt gcgaattctt tttaaagtag ccagccttac attagatgaa   14940
cctaagcaaa actctaaaag atgatgcaat gagtcaagag aaacttgatt acgtaatacc   15000
ggcatcttgt caaaataaat aatacctaaa gaagaggaaa aacagcataa atgactccca   15060
gtagttgcat actggatttc attcgtgatc cggaaagtaa tcttatcaga cagttctgga   15120
atcgaaaata cagatgacga ctctataaag acacattttg ataaatgcag taaagattct   15180
tgtgtagaaa atcctgaaaa tacctcgtat tttttttca aaaagataa tgtatcaata   15240 cgaattaccc aatccccaca cacggaagta agagtgacta aactttcact gcctgtaaat   15300 ttattttga atgtctgaat cgaaaacgc tcgcagagtt gctttgcata taaaatctgt   15360 agttttcgt tagcgtcaaa atgtttaatt cttagcattc ttcttcactc tgttcattat   15420
atcctgtact attattttta ttcccccttat tatgttgact gctatcaaat ctgtaattac   15480
cctcagcatc ttgtttcaaa attaagtcaa gtttatttcc tacaaattga tctgacggtt   15540
ttagaacaaa agaaccagac tccactgaaa tactaacaga atgtccagcc ccccactgtt   15600
taaagtggta agtcatttca ctattttttt gaaaaacatt tttatcattt tcaactattg   15660 attttcttg caatgacatg gatggggtta tgtctgcagt attttattc attacaggca   15720 gctcaaatga tttagcaaca cttccattta gtaaagaaat gatgtcagca atattcttat   15780
caatagacaa gctatgattt tttaaaccaa tttgaccatt tctattatca gattctagca   15840
gattatcagg gtttacagaa gaagtatgac ttctttcgaa gttcttgtct gcatttccac   15900
tcttattata tgaaaagatc cccctcatat cgccgatatt tatttttcc cttgctttga   15960 tatcttgatc tggtatcaaa atattttctt taatggccat tgattctgga atatcagaat   16020
atgtcgctcg ttcgtttcta agttcgaacg cattttttaat gccactataa atttctcctt   16080
tatcatgctt atgttcaaag tgcttatcaa tagtaaaata gttagatgca attaaagagt   16140
actcaggaat ttcaaccttc ctcttcttct tcaaaacgag actatcaata ttatctattg   16200
aagatagttt ctcacatttt tctatctgtt tgtcactact aaaatttagg tttatattat   16260
ctaatgccat acttcatatc ctcttgtgat aactcatcaa gtatcaactg tttggcaaag   16320
ttatttcttt taatcaagcc aatccgttta catatttac tctctttatg aagcagtttt   16380
cttttagaag catttgcctc atcaatatct ttttgaattt cttcaattct tccctttaga   16440
```

```
agaattcgtt cagactgata ttggataata tgcttttta ctatagcgat cttacgtctt    16500
gtattgaaaa gctgactaac actctgagcg cctacaggtt ctaagtcatt ctccagttgc    16560
aggaagtata taatccttt atctaatgcc tccacatctc gatacaaaga gttttttttt    16620
tagtgttaat atgtgtgctt caattaattt aacagaccgt tgatatttat ctttgatttt    16680 taaaaccta tctaattgtt tcaccaataa gctccattgt ctgctcataa gtaaaaccga    16740
gtcgataatc ttgcttcaga aaactctcaa caacagatat tttgttgtag attttatcct    16800
gagaggcatt ctccccggt tgtattcac caaagtcaat aattgtcctt agctcttcta    16860
tttcagaaag tagctcccga aatgcagcgg ccataatacg atgttttca tcaacaacct    16920 gtgtaaatac cctgcttata cttttaagg aatcaattgc aggaaattgt ccttttggg    16980 ctagatttct gctcaaatat atatgtccat ctaaaatgga tcttacctct tcagctaatg    17040
gatcagcaaa atcatcatcc tccaaaagaa cagtgtaaaa tgcagtaata gagccacctg    17100
cctttaactt tcctggcctt tcaagaagtc tgggtaagct atcaaaaacc gaaaccggat    17160
agcctcttct ggcaggtgat tctccagcgg ctaaggccac atcacgtaat gctctggcat    17220
accttgttaa tgaatcaata aaaagcgcta ctttatgtcc ttcagtccta aaaaattcgg    17280
ctatagcagt ggctatatat gcagcattac aacgatcaac cgaagagtaa tccgaagttg    17340
catatactaa aacacacctg cttttttct cagagttttt caaataatca accgtttcag    17400
taacctctcg acctcgctca ccaattaacc caataacata tatatcagca ccactatgtt    17460
caatgagcat attcatgaga aaagttttgc cacaaccagc tgacgcaaaa atccccattc    17520
gctgtccttc accacgcgtg agtaaagaat caataacctt aatacctgtt aaaaaaggct    17580
tctcaattgc agcccttca ctatatagcg gaggagcatt atctacaggt cgataaagaa    17640
tttcactgtt atctgtaaca gcaaacttat cagtaacctc ccctaaagga ttgactactg    17700
ctcccaataa tccacggccg acttgcgtat gaagaaactg ggcagtgggc ttaatcaacg    17760
tttgccgtga agtccacga gaatttccaa tcaagcttaa tattgttttt tcatcatgaa    17820
atcctacaac ctgagctctt gcaacaattt cattactttc aattccagcc tgaatgttac    17880
aaatctcacc aatcgaaaca tcgctaagac ttgtttccaa gattggcccc gagattctat    17940
taggaaaaga taattgagtg agcaattttg tatagctcat tgattataag accccattta    18000
agatttccat cctctgataa aactcatgca gaatctctgc aaaaacaatc ccatcgtgaa    18060
cgtagtcatc tttaataaca actcttaact gtaagtactc atcagaacga tgaagctcta    18120
ccagctcatt aatgctataa ctaaagttca ttaacattaa atttaatatg ttataagcag    18180
atgactgaag ttttacatca cttggtgcat caaaattagc ccataacata acctgctcat    18240
tgacaagagc tatattaata gcaggcatac tatccaaaga aatggtaatc gctgaatggc    18300
tgtctaaatc tgtaataatt gatggaggac aaccaatcgt gaaaagacta tctctaacta    18360
attgaactaa attaatgtta ctcatatta aacctcacta aatagtcttt aatacattaa    18420
tggtatatgc ttcatcaatc tcagcatacg atataacgag tatactctta aatctgttat    18480
ctataagtct tttaacaaac ctacgtatat ctactgatac caaaagaacg aaatttttt    18540 ttgcatttct caattctctc aaagcatgtg ctaaagtttc cattacctca tccgaaacct    18600
ctatatccat attcaagaaa gagccaccag aggtttgcct tatcccttt cttattgcat    18660 cctcaatata tccggaaagc atcacaactt taatctcacc agaaacagct atttactac    18720 aaatatacct agaaagtgat gcacggacat gttcaactaa tgttatgaca tcttttctc    18780 tgggagccca aagcgccaaa gactccataa taagttttaa attgcgaaca gaaatatttt    18840
```

```
ctccaagcaa tctttgtaat acctcagaaa ttctctgtat agtcacatgt cggaagactt    18900
cctttaatag atcaggatac cgattttcaa actgatctaa catattttt gtttcttgta     18960 taccaaaaat ctcatttatg ttgtttaata aagcttgtga caactggtga taaaattcat    19020
cttgagcact tttaatttta gcatcaatat tagttagatt ttctgtatat gaaacgtcta    19080
cccaagaaat aacacgttca ttatatgaag ttgaaacaac aggaataccct agagcatcta   19140 tatctccatt ttcatctgta atacacactt tgtcaaaata tatattaaaa ctatcggcac    19200
gcacctcatt tattaacaaa acaatatcat cgaccttaag ctcattgctt gttctatata   19260
aaatagttgg aagcctgaca ccataatcaa taaagaactg acttcttatc ctttcaataa   19320
gaccttccat atcatttgca tttatcttat tttcggcaaa taataaaatt aaggaacgg    19380 tttctgaact aatagcatcc agattttcta tcattgccaa agatgagtca tggctattat   19440
caatatcaaa tgtaccagta tagccactag aatcagactc agacagactt ttttctttt    19500 ctacgacctt tttataatag aataaagccg tcaaagtaac tgctatcagg aaaaaaacaa   19560
aaaacggaaa acctggcaac atccctatcg ccaaggcaag agctgatgta acaatgagaa   19620
caaaaggatt cccaaatatc tgggacatta tgttacgtcc catattatcg ctatcaccat   19680
taactcttgt aacgataaat cctgcactta tagaaattaa cagagcagga atctgagaga   19740
ccaatccgtc accaatagtt agtatggtat aagtagataa tgcaccagat agggacattc   19800
catgttgact cataccaaca gaaataccct ctattaaatt gacaaaaata ataatgatgc   19860
cagcaattgc atcaccttta atgaacttca ttgctccatc aaatgaacca tacaattgac   19920
tctcacgttc cagaatactg cgtctttctt tagctcctgc ggcatcaata attccagcct   19980
ttaaatccgc atcaatgctc atttgttttcc ccggcatacc gtcaagagaa aagcgagcag   20040
ctacctccgc aaccctttca gatccttttg ttataacaat gaactgcaca acagttacta   20100
ttgaaaaaat aacaaaacct acagccagac tatcaccaat gacaaactgg ccaaatgtag   20160
taataatttt acccgcatcc gcatcaacta aaattagtcg actagtactt attgataaag   20220
cgagacgaaa taatgtcgtt atcaacaaaa ccgaagggaa tgtagaaaaa ctcaatattc   20280
tttcaatata aaatgatccc ataaaaacga gaatagcaag tacaatatta agccctatta   20340
aaaaatcaac aaggtatgta ggtaatggta tgatcaacat agcaatgatc ataaccataa   20400
gcactaatat aattaattca ggcttagtac ttacttgctt aagaaaagac tggatcactt   20460
ttatctcctg ttatctagaa agctcttttct tgtatgcact tgtgacaagc tctcgtagaa   20520
tattgatcgc aatttctctt tcactttcac ttttaaatat atcatgagga ctttcattaa   20580
cagaagatag atatgtttga tacactacag aatcctcatg actggctcgt gatacttcta   20640
taacagaagt aagaatttgc tcactttcac ttggatattg aaaatatat aataaagtta   20700 gcaatagctg ctctgcactt aaactgccat cttttagcaa gcttgaggat tccagtttct   20760
tcataaaaat tacgtctgaa gttctaatca tcttaattgc aattaattta gataacacaa   20820
aaccaaactc ataagcatta cagctcggtt tctcagaatc catgtctaca atcagtgact   20880
gctctacaaa attcacaatt gtatgtctgt gattaaaacc aaaattacca agccattcta   20940
tatactgatc tgttgttgat atgttcccca tgataaaacc acgataacat gcacgcaaaa   21000
gctgtggttc aagtttcatt ttgttgccaa ataatttagc ctgtatagct gaatttattc   21060
cagcattaac acttttttca ctacctgata ttatctcatt aataatttta gttaataatt   21120
cgacttgttc agcagtaaga tcttttttcat tcaaaagttc ccttaatgct aagacttgat   21180
```

```
cacttggatc tttaaaatat ctctttagtc tgtctataaa atcccgatct agaggaaggt   21240
tatcttttaa cgttctcttt aaatcaaaaa tcttgtgatt aatttcatct tcttccccat   21300
ctaaaatacg ttcctgacta tcactatttg ttcctttcag tttctcaagg tctcttctgt   21360
ttataaatga cgaaagagcg gaagccatct catcagatga gtcaatatac ttgctattag   21420
ccaagccaga atcaagctct gcatcagcag tctcatctcc atcatctgaa tttgtcattg   21480
cattcaactt atcaatgaat gcagagctaa aaactcctgt attttttaaca tcaagcatac   21540 atcacctact ttatagttag taatttaagt atgaaaccaa tgattttttcg tcttccagca   21600 aagtagtttc agatgggatt atttgtgtag tcttttgtat ttctctttca gatatgaggc   21660
ttttatattc tgcagtatta taataacttg actcctttat ctcacggggt tgaatcagaa   21720
aaacccttac aatattactg atattacttg ttttatactt gaacacatta ccgattacag   21780
gaatagagga gagaaaagga atagatatta tttcgttaga gttcgtttca tgcgtataac   21840
cacctatcaa caaactttttg ccttgtggaa ctctcgctat tgtactgatt ttggtccttc   21900
caacttctgg aaggacagat gtattttcat tattataatt gtaatttgac tgactatttc   21960
ctgttccatc ctctatcgtt aaagacatct caatttgtcc ccgagatgaa aagcgaggta   22020
taacatttat caatgttcca tacgtaacat gctccaacga agaattgcgc tcaccaacta   22080
atgacacata aaaagtcctg ttattatcaa atatagccgg aatattctct tgtgtcaaaa   22140
tcaccggcct tgaaactaca tttgcttttct ttttctgatt taatgccata actgaagcaa   22200
taaacttatt gccgtccaaa gtgcttatcg atgctgatga gctcatatta aatgacgcac   22260
caaacgaatc accaaatgaa gccgttcctt gccaattaac accaaggtta tttaattcag   22320
atttatcaat atcgattatc cataatgata attctatatg tcgtttggct atatctaact   22380
gagtgataat atcgcgaata atctgtattt gctgatcatt acctttgact aatatagaat   22440
tggtttctgg atatgcaata agtgatacat cctctaatat agaactattg gtaactgaac   22500
taaatgaaaa gtcattacta tcctcagata ctttctgtgt aatattaaag ggtggcatcg   22560
gatcattttg ggcttgtctg ttactcagag ccttaccatt atttaataaa cgttctacaa   22620
cagtagccac ccctgggatg acaatatcct cccctctcat attataagtt ctgtcactaa   22680
caaatgtatt ttttaatttt ataaccccaa aattaacttt atctgtccca atagaagaaa   22740
cctgcttatc aagcaaagtt gctgtattag ctaccagttc aaccaatgcc ggaggaccag   22800
atatatagaa tgtttttatca ctaatgtttc ctcttatagg atatctgtga tcataaaggt   22860
tagcatcctt cagatactga ataagataat taagtgatat attctccagc aaaataactt   22920
tgcttattaa ttctccagag tcatatatgt ataatgcatt tccatctttta taccatatga   22980 gtcccacaag taatgtcagt ttttcaagca tttcttctgg attagataaa tcaaactccc   23040
cagatattct cttttttgca gcttgtttgc taacaacaat aggataattt aataacgcag   23100
aaaaacgttc aaaaaaagat cctaccgtat cactttgagc aacatatttc gctatgtcat   23160
tttgttctaa taaatgagag tcaatattat tagcattaac tatcaatggt aacaatacaa   23220
tcaagagagt caaagattta atattaaatt ttttcattta ttttttttcac taaaaaagta   23280 atattcgata attctcttgc agaaaagcct agtcgtgttt ttatctcatt tgaaaaatgg   23340
gatgttgatg catacccatt attcatggca gctgaagtga ttgtttgatt gtgcaaaaat   23400
acatctaata aaccatttac taaccgccaa gtgttcagtt gttctttgac ttttgcccct   23460
aaagcttttc tacataaaga tctaaaataa gcctccgaca caccataatg ctctgtcaga   23520
ctctttattc ttacctcctt ttctttctca atagttctca gaagataaag aaccaaatga   23580
```

```
tatgactcag tcattcgtat catagccagt gcattactta cattctggtc agatgaaaag   23640
atgaatctta acattaactt atcaagcatc gattcggtat tacaactatc ccgaagatca   23700
ttctcatgat agaaatgaat acatttttca gcatggctat gctctactag agcaccactg   23760
aaatagtccc aaaaagcaag aaattttgca caactattaa tgttaaagcg ataatgatag   23820
ttcacattat cactgaattt tatattttga tttcggacaa aaaaaaaccc ttccatgctg   23880
gagccagctc aattatgtta cgttctttat cttttacaag ctcaacgtta actggttcat   23940
gtccactaga gtaaatgtaa acatattac ttgtatttag acctttatat ttactcacaa    24000
tacaattata tccctcgaat taattttaat ttaacttccc catccttctc tataaggatg   24060
gtatcattta tcttattacc ttttaaaaca accccgtctt tcagcataga aaatagttta   24120
tctatagcta tcttttgtgc atccatgaag cacccatcta cttccttaac attaaagttg   24180
cccatgaatt tacctgcatt aaaactataa accgccttac cactaataca tttagagtaa   24240
acatttatac ttttattggt tgtattaaac gaccataata aatcatttgg aatagaaaaa   24300
taatccttac ttacaggaac aatatgccat tcttttcag aattagatga tgactttaaa    24360
gcacacccac tcagtgttaa tagcaatata cttaaaataa atattttcaa cttattacta   24420
ccatgtcgaa tcatctgcct ctctccctgc ttcaaagaca ctaattaatg aatcgaaggt   24480
tgtagtctta atatagaaat caatattgtt atatatggac aatgatgcat aaaatccctc   24540
atgcaaatcg acatattgat ttgcatctat gagtttatta agaagtgaac ttttttgtgc   24600
agctgtaaga taaggaaaac gtgaattgaa taattgttca atcttattgt gcagttcatc   24660
attatctatg gaatttaatt cactctgtga gaaatattgc attatttcat agattatatc   24720
ctcatcaaat gattgcgaag atgataatct ctcatttaaa ttaacaactt cttcactatt   24780
taatctttgc tgcagagcat tgcttgcatt tatttgatta atcattaaca ggattctctt   24840
ttaacaagtc ttctgcaatt tgtctcagtt tcttatgtgc taactctttg aaatattttt   24900 tatcatttt tgttaatttt tccgcaagtt ctattttaac acctgatatt acatcctgag    24960
gactaaactc cactacttga ttaccactac agaatatata attattccct tcagaatatt   25020
ttaaaataat cttgacatct gagcgatatt tatggagatc aagttctaac ttttttcctca   25080 gtgctaaatt acacttgggc aaaaccactt ttaattctgt tactgtatta cgcaacgaac   25140
taagccactg ctccaataaa gtgctaatga tcctctcatc atgtaaattt tctgaaagca   25200
aactagttat atagtcctca atatttcttc tattttcatt ttgctttaac ttccattcac   25260
aaatatagtc aataatatgc tcaaaagcag tctgtatacc aatttgataa ccatcacata   25320
cagcatctat acgcagtgat tcagcttttt tcgtagcctc ctttataaca caaattgctt   25380
tcttcttact ctcagtgtct ctatctttta tggttttaca taattccttt tcaattctct   25440
ttataacaac accatcatag gcatgatgtc tggataccgg taaagtgcct ttttgcatat   25500 tgcataccctt catttaatcg ggacaaattt cttctacag gcgtataatt tccctccaaa   25560
gcaattggat taaataataa gtttattctt tcatatatac caacagatat attttccttc   25620
cacgcaataa gatgccaaaa accacttcga atagcggcct ccccttgctt actgattttg   25680
cccccataat aactaataac catctcacta tgattaatta accgagactc ttgactaccg   25740
ataaaataag caacagctgg aagtaaattc cagttggcaa caaacatagc ggttaccccg   25800
cttaaaggtt caatatcgca atttagatca tatttattaa ttatgagatt attaatctca   25860
cttctgatta cgccatttc taacagttca gaaggcaaat tcaaccgatt tctatttata    25920
```

```
tagaacgctg gatcaaaaat tattgaaaga tattttttat aaattccatc cattcttatc   25980
atattttgtt tctcttgaac caccctgttt tgaatgccca taccaaaaga atgacaacta   26040
gtacagccat cccgagaaat aaatatatta cttcatttgt taaaaattcc gatttaactt   26100
ccttaacagg ttgtacattt gtataaacat attcttcttt cggagttaat atgacagata   26160
tattttcata cttaacatca gaaaaggtgt ttttcaaaaa tcgcttaata ttactaacta   26220
atagttcaga ctcttcggt gagtcatata tagcgattac tgatatatgc atcggttttg    26280
aagatatatt ttttcttca agatcatagc taacatgtat ttttgccgaa ataacaccac    26340
caatagaaac taaagactgt tccagccgtt gctcaatagc actatataaa cgggcctttt   26400
cagctcttgg agaagacact aatgaatctg taggaaacat ttgtgagata tcaactctct   26460
ccggatttgg caaatcgtac atgcgcatca aatcaactgc cgatgcaaat gtccccttt    26520
cgacttgtac cgagatcccc tgtttacctc catcaacttt tctagcagta atattatggc   26580
gttctagcac agatattatt tcatttgcct gtctttgaga taaattagaa attaactctt   26640
cacgttgctc acatccaatc aacatcagca acaagaataa aataaaacct ttatacctaa   26700
tcatataaat taagacttta ataaagtttc aacagccgaa actgttttc ttgctaacgt    26760
gccagctaat gatactccta ttgaataatt tgagagcgtc gtctgtaact tggcaaaga   26820
ttctgggttt aatgattctg gattgcttac catctccatt atttgtgata cttgaatatc   26880
tgtatccatc ttaatatcac tatatttagc cgacacgacg tcttccagac ttgatatctc   26940
ttgagattga aaatcactgg ctttgataat atcaacctga ttgactggat aaatgtaatt   27000
catgaatgct ccctattatc tgaagttttg aataattgca gcatcaacat ccttaatcac   27060
tttcactgta ttggattgcg cgttcctata taatgtatat tcagataatt actttggta   27120
ttcagccagc aactgtggat tcgaaggatt tttagctaat ttatctagtg ccaatgttag   27180
ttcaccttgt aatgtttgag ttccatcatc aaaagtttca gataatgaac tcaatgtcca   27240
atcatcattc ggtactgtaa cactcatttt atcctcactt ttttatct aaaaaaaacc    27300
agtgtttatc attcaacatt acataactgt ctttgctgtt aagatatgat ttacctttaa   27360
aatcatcatc tatcaaaagt acagaaaact caatatactg atctccatat atattttat    27420
gttcagaaat cagtctatta atgagctcaa gcttttcatc tgtcagttct tctctgacag   27480
aatatgtaac tttattattt tcacaaatct ctttatactg gacatttacc tttgtgaaaa   27540
tacctttagc atcccccctt gcattatgat cgctaagata gttgaattta atattttga    27600
tatacggaaa ttcaacaatc agagcatttt tcaatttatc aagttcggta tcttttgaac   27660
tatttctttc tttacttaaa aacaccagta attccgcttt atcactcact aaattcaaca   27720
catacaaatt gataaatggg aatcgttgat tgatatattg ttgaattcta tttatttctt   27780
tgtttgacac cagaatatat ctgcatttgg taaatccggt tttatttaag gctacagacg   27840
cccataccgc atcattttgt gtttcggcaa gaatataatt gcactgtcca gtgttgacta   27900
ttccatatct cttatcatct ataatttcag caatttcttt tacttcatct ttctttaaag   27960
agagggaaaa aattataatt aacacaacaa taacagcaaa gaaaaaaaac accgagtggt   28020
tcttatacat tccgtttagt atatggcctc tcgatttatc ctccctcata tttttaaggt   28080
gaaagaaat cccgtcatat tcaaatgaat taaattgtga attgatatca atttgctcac    28140
cttttttcatc actaaattga cagatattat ctttgcttat ggtcaaataa attataccat   28200
ccgatttact atctgttaca ggaataatat tttctgggaa attgtcgttt ccaaactcaa   28260
gtgtttctat cgtccgtccg agaacaatta agttattccc ataatataac ggaaactcat   28320
```

```
ccccgacacc gtttgtgagt ttcactaata acctgaatgg tgcaagattt gagttctttg   28380
cctcagacat aaatcctctt atatccttcg attattctgc ttgctctctg ctgctatccg   28440
caaatagcgt ctatagatat cctctgcgta ctttaatctt tcttttttct ttttcggaga   28500
cgttcctgca ttataggctc caacagcctc ccaccctctt ccatacatca tcataaactc   28560
atttaataac tttgctgcat aatgtacaga aagacatgga tgactaatta gcatttcctc   28620
agaatatccc atttctctaa gtcttttaga atgaaagtca tttatttgca ttataccata   28680
atctttactt ccattgttat taacattgac tgcagattta ttaaatccgg attcttttc    28740 cgcaatcgct tttaacaaac ttgatggaat attgtacctt tcaccagcct tatcccaaca   28800
atcagctctc cctaaatatg ggataaaaca cagcaaaata aatacgaaac gggacattaa   28860 tacccccttca ttcttcgcgc aaattcatcc ttcagccaac gcacacgcga aatataaat   28920 tctgtattaa catatacatc ctcgaattca tttatcccgg taagatctaa tcgcgcaatt   28980
agatttccgc cttcatcatc agtagctaag catatctttt ctgagtaatt taggctcaac   29040
gcatatataa gatcatttat attttcaggc aatgcacaaa aagggcataa taaatttatt   29100
gaatctcctt ctttttcaat atatattagc acatcatcat caagcatgat tgcttgatca   29160
tcgatatcaa ttaaagggat acccaaggct cggcaaataa catctgctaa atcttccata   29220
tattcctctt atacaaatga cgaatacctt tcaccatat tccatatttt tgggtcccct    29280
attctttcag aataagatag ctctaacgaa gatagcggca attttttcat gactttattt   29340
ccgggcacac cagtattcat ctcttggatt tccatattac cactattcat tagaatagta   29400
gaaaataatc ttttctcttc tgaggataat ttactattta attgagaaaa ctgacctgtt   29460
tcatgttttc ttattatttc tcttttaatt tcagcatcct gcatacctgt tctgtccttc   29520
ccactcttac aattccagca aggtacagca cctatagtat aagccaatag agtcattctt   29580
tgtgacaatt tatacggctc tccattatca ttttttttgta actttttggt tacaatctct   29640
tttatctggt tagccagata tatcacatca ttcttacatg gtggattttt ttctattgct   29700
tctgcagccc aacctccaat cacaccattt ttgaggaaat tatcccccaa caaagaacat   29760
attgattcat cattaagctt gtcaacattc ctccagccta agcccatttt tagcgctaat   29820
tcatttacac caaagttaaa tgtcaccact tttagattaa cgcttacttc tttcagaaga   29880
ccatcactat tccgaattaa taatttcgtt ggctcccccc ttttagagtt taaccctttt   29940
aatgcgttca cctgatcttt taacatactc tcctctcccc cggttaaact ggtcggcgtc   30000
agaagagaag tcgaaacaat cttta aatct actgttttac cagacaaagc ctgtgataat   30060
aactctggtc tgctatataa tgctgcgctt actaactcct cagctttatt acgagcagca   30120
acagctcttt cagatgagtt ttttttcaat ccataggctg atataactcc atgtctgata   30180
cccgaaaaaa tttccttccc ctcatcatcc accacttttg aaagccacat attcgcgata   30240
tgatcactct ctctcgtaga agcacaacaa attccttttc cattatactc tttgacaaat   30300
atatttttat tccctatctt catatgagag gcaggagtta attgaaaacc ataattttc    30360 ccatgatgac taaatattctt gtcgaccggt ccccaattct tattatttaa ataatcagta   30420
aatatttgtt ttattttcgt ttgcaattcc ttttatttt taatgcctag ctgtgctctt    30480
atctcttcac ttattacttt attaagctca ttaatatgtc ttttattaac ttcaccaagt   30540
ttataggtat ctaatcgttc catcatggct ttaattttg acgtatcacc acctgccaac    30600
tttattgcct cgcaaaaaac ttcagctctg tcacgcgcaa acaaaaggct ttttcctgtt   30660
```

```
aagcttgttt ggttctgtaa atataatcga ttaagcgctt cgatcccctt atttctttct    30720
ccattttaa ctctttgata tgaaatcacg cttacacctt tgtgcttcc ggtttcttct    30780
gcgcctttat aggaatctcc gctttgaaat gaaacctgat gcaatcccaa attagttatg    30840
tgcatttaat tatcctcagt cataaatggg gcattgattg cagttttgta cctcgtttta    30900
caacaaaaaa gatacttatt caacagggtt ctctctttt ctataacact ccgagcctga    30960
tacatcaggc actttatctt gtgggatttc atgatgaaac gagcactaca tatgctcacg    31020
aggtacatat tatgtacagc aaaagaaaat ttgattatgt taacaggctc aagtttctaa    31080
atttattaat tgaatatatt ataccaaa tacattttac atccccacaa tcaccaagta    31140
atggagagtt aataaagtat gatcctcaaa attagcaatt tcattgacgc aagcaataca    31200
aaagggccta tacgcgttga agatacgag catggaccta tattgatagc acagaaattc    31260
aacctaaagg atctcttttt cagaacatta agcactatta atgcaaagat aaattcacag    31320
atattaaatg aacaactaaa aaattatcga ctagagaatc aaaaatcctt attgcttttc    31380
ctcaatacat tagctagcga aaaatctgca gaaagtgcgt ttgccgccta tgaagcagct    31440
aaaaactcaa ttcaacactc tttcacaggt agagacatca aattaatgtt gaataccgca    31500
gagcgttttc atggcatcgg tacagccaaa aatcttgaaa gacatttagt ttttcgttgc    31560
tggggaaata gaggcataac ccatttaggg catactagta tcagtataaa aacaattta    31620
ctacaggaac caactcatac ctatctcagc tggtatcccg gcgggaatgt tacaaaagat    31680
acagaaataa actaccttt tgaaaacgc tcaggttaca gtgtcgatac ctataagcaa    31740
gacaaactaa atatgatttc agaccaaaca gccgaaagac ttgatgcagg ccaagaggtt    31800
agaaacttat taaattcaaa acaagatcaa aataacaaca aaaaaatatt ttttcccaga    31860
gctaatcaaa aaaagaccc ctatggttat tggggggtca gtgctgataa agtatacatt    31920
ccattatcag gtgataataa aacaaggat ggtaaaatca gccataacct ttttggcctt    31980
gatgaaacaa acatgtcaaa atttatatgc aaaagaaag cagatgcttt cagacaattg    32040
gcaaattata aattaatcag taaatctgaa actgtgctg gtatggcact taatgttctt    32100
aaagcaggaa attctgaaat atactttcca ctccctgacg ttaaattggt tgctacacct    32160
aacgatgtat acgcgtatgc aaataaagtt aggcaacgca ttgaaagtct caatcagtct    32220
tataacgaaa taatgaagta tattgaatct gattttgatc tttccagatt gactcaatta    32280
cgacgcagct atcttaaaag tttcaataaa attaaccta tccacacacc aaaaacattc    32340
aagcctttat caatttcact ttacaaacat cctactgaaa atgtatcttc agaagacttt    32400
gatgcggtca tcaacgcttg ccactcatac ttagtaaaat cagcacccag caatatgact    32460
cgtgtattaa acgaattaaa aaccgaagca acagataaaa aagaagaaat catcgaaaaa    32520
tcaataaaaa ttattgatta ttacaattct cttaaatcgc cagatcttgg aaccaaactt    32580
tacattcacg acttattaca gatcaataag cttttattga ataactctca ttctaatata    32640
tagaaggcca tagaaatgtg tcgcaaacta tatgataaac tttatgaaat aacaggtgca    32700
aagcttgatt ttaacgataa aaatcaagcc tttatattgc tcgaagaaca ataccctgtt    32760
tgtataacag ataatgatga atacatcttt ttgaccggac ttcttaatga acatgaactt    32820
tttacagaaa atattattaa tccagaacac atactcatcc ttaactactc tttgagtaga    32880
gattatggtt cttctatctg tcttctccct gatactcatc aatgtgtttt gaccaagaaa    32940
cactacaaaa aatatctttc acctgatgaa ctcattgaat ctttgtatga atttttattt    33000
tgtattaaac taaccattgc aaacatcact tcagaagtga actaacatat aggggggtatc    33060
```

```
atgcaaattc taaacaaaat acttccacag gttgaattcg cgattcctcg cccatcattt   33120
gattcgttaa gtcgcaataa gcttgtaaag aaaatattat ctgtttttaa cttaaaacaa   33180
cgctttcctc agaagaattt tggatgcccg gtgaatataa ataaaatcag ggacagcgtc   33240
atagacaaaa taaaagatag taattcgggg aatcaactat tttgttggat gagccaagag   33300
cgaaccactt atgtctcttc aatgataaac agaagtatag atgaaatggc catacacaat   33360
ggagttgttt tgacctcaga taacaaaaaa aacatatttg cagctattga aaaaaaattc   33420
ccggatataa aacttgatga aaaatcagca caaacatcta tcagtcatac agcactaaac   33480
gagattgcct catctggcct cagagcaaag atttaaaac gctatagcag tgacatggat   33540
ttgtttaaca cacaaatgaa ggatcttaca aatctagtat ccagttccgt ctacgataaa   33600
atatttaatg aatcaacaaa agttttacaa atagaaataa gcgcagaggt tctaaaggct   33660
gtataccgtc aaagcaatac aaattaaatc ttttatatta aatcttatac ttattaaagt   33720
aaagcagaca aaaggagac cttatgtctt taaatatcac cgaaaatgaa agcatctcta   33780
ctgcagtaat tgatgcaatt aactctggcg ctacactgaa agatattaat gcaattcctg   33840
atgatatgat ggatgacatt tattcatatg cttatgactt ttacaacaaa ggaagaatag   33900
aggaagctga agttttcttc aggttttttat gtatatacga cttttacaat gtagactaca   33960
ttatgggact cgcagctatt tatcagataa aagaacagtt ccaacaagca gcagaccttt   34020
atgctgtcgc ttttgcatta ggaaaaaatg actatacacc agtattccat actggacaat   34080
gccagcttcg gttgaaagcc cccttaaaag ctaaagagtg cttcgaactc gtaattcaac   34140
acagcaatga tgaaaaatta aaaataaaag cacaatcata cttggacgca attcaggata   34200
tcaaggagta attattatgc ataatgtaag caccacaacc actggttttc ctcttgccaa   34260
aatattggct tccactgagc ttggagacaa tactatccaa gctgcaaatg atgcagctaa   34320
caaattattt tctcttacaa ttgctgatct tactgctaac caaaatatta atacaactaa   34380
tgcacactca acttcaaata tattaatccc tgaacttaaa gcaccaaagt cattaaatgc   34440
aagttcccaa ctaacgcttt taattggaaa ccttattcaa atactcggtg aaaaatcttt   34500
aactgcatta acaaataaaa ttactgcttg gaagtcccag caacaggcaa gacagcaaaa   34560
aaacctagaa ttctccgata aaattaacac tcttctatct gaaactgaag gactaaccag   34620
agactatgaa aaacaaatta ataaactaaa aaacgcagat tctaaaataa aagacctaga   34680
aaataaaatt aaccaaattc aaacaagatt atccgaactc gacccagagt caccagaaaa   34740
gaaaaaatta agccgggaag aaatacaact cactatcaaa aaagacgcag cagttaaaga   34800
caggacattg attgagcaga aaaccctgtc aattcatagc aaacttacag ataaatcaat   34860
gcaactcgaa aagaaaatag actcttttc tgcattttca aacacagcat ctgctgaaca   34920
gctatcaacc cagcagaaat cattaaccgg acttgccagt gttactcaat tgatggcaac   34980
ctttattcaa ctagttggaa aaaataatga agaatcttta aaaaatgatc tggctctatt   35040
ccagtctctc caagaatcaa gaaaaactga atggagaga aaatctgatg agtatgctgc   35100
tgaagtacgt aaagcagaag aactcaacag agtaatgggt tgtgttggga aaatacttgg   35160 ggcacttta actatcgtta gtgttgttgc agcagctttt tctggaggag cctctctagc   35220
actggcagct gttggtttag ctcttatggt tacggatgct atagtacaag cagcgaccgg   35280
caattccttc atgaacaag ccctgaatcc gatcatgaaa gcagtcattg aaccccttaat   35340 caaactcctt tcagatgcat ttacaaaaat gctcgaaggc ttgggcgtcg actcgaaaaa   35400
```

-continued

```
agccaaaatg attggctcta ttctgggggc aatcgcaggc gctcttgtcc tagttgcagc    35460
agtcgttctc gtagccactg ttggtaaaca ggcagcagca aaacttgcag aaaatattgg    35520
caaaataata ggtaaaaccc tcacagacct tataccaaag tttctcaaga attttcttc     35580 tcaactggac gatttaatca ctaatgctgt tgccagatta aataaatttc ttggtgcagc    35640
gggtgatgaa gtaatatcca aacaaattat ttccacccat ttaaaccaag cagttttatt    35700
aggagaaagt gttaactctg ccacacaagc gggaggaagt gtcgcttctg ctgttttcca    35760
gaacagcgcg tcgacaaatc tagcagacct gacattatcg aaatatcaag ttgaacaact    35820
gtcaaaatat atcagtgaag caatagaaaa attcggccaa ttgcaggaag taattgcaga    35880
tctattagcc tcaatgtcca actctcaggc taatagaact gatgttgcaa aagcaatttt    35940
gcaacaaact actgcttgat acaaataagg agaatgttat ggaaattcaa aacacaaaac    36000
caacccagat tttatataca gatatatcca caaaacaaac tcaaagttct tccgaaacac    36060
aaaaatcaca aaattatcag cagattgcag cgcatattcc acttaatgtc ggtaaaaatc    36120
ccgtattaac aaccacatta aatgatgatc aacttttaaa gttatcagag caggttcagc    36180
atgattcaga aatcattgct cgccttactg acaaaaagat gaaagatctt tcagagatga    36240
gtcacaccct tactccagag aacactctgg atatttccag tctttcttct aatgctgttt    36300
ctttaattat tagtgtagcc gttctacttt ctgctctccg cactgcagaa actaaattgg    36360
gctctcaatt gtcattgatt gcgttcgatg ctacaaaatc agctgcagag aacattgttc    36420
ggcaaggcct ggcagcccta tcatcaagca ttactggagc agtcacacaa gtaggtataa    36480
cgggtatcgg tgccaaaaaa acgcattcag ggattagcga ccaaaaagga gccttaagaa    36540
agaaccttgc cactgctcaa tctcttgaaa aagagcttgc aggttctaaa ttagggttaa    36600
ataaacaaat agatacaaat atcacctcac cacaaactaa ctctagcaca aaatttttag    36660
gtaaaaataa actggcgcca gataatatat ccctgtcaac tgaacataaa acttctctta    36720
gttctcccga tatttctttg caggataaaa ttgacaccca gagaagaact tacgagctca    36780
ataccctttc tgcgcagcaa aaacaaaaca ttggccgtgc aacaatggaa acatcagccg    36840
ttgctggtaa tatatccaca tcaggagggc gttatgcatc tgctcttgaa gaagaagaac    36900
aactaatcag tcaggccagc agtaaacaag cagaggaagc atcccaagta tctaaagaag    36960
catcccaagc gacaaatcaa ttaatacaaa aattattgaa tataattgac agcatcaacc    37020
aatcaaagaa ttcgacagcc agtcagattg ctggtaacat tcgagcttaa tatatccaag    37080
agccataata atatatggct cttcctgtaa ggaaataacc atgaatataa caactctgac    37140
taatagtatt tccacctcat cattcagtcc aaacaatacc aacggttcat caaccgaaac    37200
agttaattct gatataaaaa caacgaccag ttctcatcct gtaagttccc ttactatgct    37260
caacgacacc cttcataata tcagaacaac aaatcaggca ttaaagaaag agcttttcaca    37320 aaaaacgttg actaaaacat cgctagaaga aatagcatta cattcatctc agattagcat    37380
ggatgtaaat aaatccgctc aactattaga tattctttcc aggcacgaat atccaattaa    37440
taaagacgca agagaattat tacattcagc tccgaaagaa gccgagcttg atggagatca    37500
aatgatatct catagagaac tgtgggctaa aattgcaaac tccatcaatg atattaatga    37560
acagtatctg aaagtatatg aacatgccgt tagttcatat actcaaatgt atcaagattt    37620
tagcgctgtt ctttccagtc ttgccggctg gatctctccc ggaggtaacg acggaaactc    37680
cgtgaaatta caagtcaact cgcttaaaaa ggcattggaa gaactcaagg aaaaatataa    37740
agataaaccg ctatatccag caaataatac tgttagtcag gaacaagcaa ataaatggct    37800
```

```
tacagaatta ggtggaacaa tcggcaaggt atctcaaaaa aacgggggat atgttgtcag    37860
tataaacatg accccaatag acaatatgtt aaaaagctta gataatctag gtggaaatgg    37920
cgaggttgtg ctagataatg caaaatatca ggcatggaat gccggattct ctgccgaaga    37980
tgaaacaatg aaaaataatc ttcaaacttt agttcaaaaa tacagtaatg ccaatagtat    38040
ttttgataat ttagtaaagg ttttgagtag tacaataagc tcatgtacag atacagataa    38100 acttttctc catttctgag gtgcgccatg cataatgtaa ataatactca agcgccaaca    38160
ttcttatata aggcaacttc accatcatca acagaataca gcgagttaaa aagcaaaata    38220
tccgatatcc atagttcgca aacttctcta aaaacaccag catcagtgtc tgaaaaagaa    38280
aactttgcaa cgtcttttaa tcagaaatgt cttgatttt tatttcttc ctcagggaaa      38340 gaagatgtgt taagaagcat ttattccaac tcaatgaatg cgtatgccaa aagcgagatt    38400
ctcgaatttt caaatgtttt gtactcctta gtacatcaaa atggtcttaa ttttgaaaac    38460
gaaaagggac ttcaaaaaat tgtcgcacag tattcggaac taattataaa agataaatta    38520
tcccaagatt ctgcctttgg accatggtcg gcaaagaata agaaactcca tcaattacga    38580
caaaacattg agcacagact tgcactatta gcacaacaac acacatctgg tgaagcttta    38640
tcattgggac aaaaactcct caatactgaa gtatcatcat ttatcaagaa taatattctt    38700
gctgaattaa agttaagtaa tgaaactgtt tcatctctca aactagatga tttagttgac    38760
gcacaggcaa aacttgcctt tgatagtttg cgcaatcaac gtaaaaatac tattgatagt    38820
aaaggatttg gtataggtaa actgtcaaga gacttaaata cagtagccgt gtttcctgag    38880
ctgttgagaa aagtccttaa tgatatttta gaagatataa aagattcgca tcctatccaa    38940
gatggcctcc ctacacctcc cgaagatatg ccagatggcg gaccaacccc cggagccaat    39000
gagaaaacat cccaacctgt aattcactat catataaata atgataatag aacttacgat    39060
aatagagttt ttgacaacag agtatatgac aatagctatc acgagaaccc agaaaatgat    39120
gcacagtctc ctacttctca gacaaacgat ctattatccc gtaacggaaa ctcattacta    39180
aatccacaaa gagcactagt tcaaaaagta acttccgttc taccacactc tatatcagat    39240
actgtccaga catttgcaaa taattcagct ttagaaaagg ctttcaacca tactccagat    39300
aattcggatg gaataggttc agacctgtta actacgagta gtcaagaaag atctgcaaat    39360
aactctcttt ctcggggaca caggcctctg aacatacaga actcttcaac cacccccct     39420 ctccacccgg aaggagtgac aagcagtaat gataactcat cagatacaac taaaagtagc    39480
gcttctcttt ctcatagagt agcttcgcaa atcaataaat tcaactcaaa cactgattca    39540
aaagtacttc agactgattt tttatcaaga aatggagaca catatttaac acgggaaacg    39600
atatttgaag cttcaaaaaa agtaacaaac tccctaagta atcttatatc tctcattgga    39660
actaaatcag gaacacaaga acgagagtta caggaaaaat caaaggacat tacaaaatcc    39720
acaacgaaac atagaataaa caacaaatta aaagttacag atgcaaatat aagaaactac    39780
gtaacagaaa ccaacgcaga tacaattgat aaaaatcatg cgatctatga aaaggcaaaa    39840
gaagtatcta gcgccctcag caaggtattg tcaaaaattg acgatacctc tgcagaatta    39900
cttacagatg atatatctga tttaaaaaat aacaatgata ttacagctga aaacaataat    39960
atatataaag cagcaaaaga tgtaaccact tccctatcaa agtattaaaa gaatatcaat    40020
aaggattaaa atatgataaa agaaaaaata ttatcaatag tggccttttg ctatggtata    40080
gcgtacagca aactatctga agaaactaaa tttattgaag atctttctgc cgattctctt    40140
```

```
tctctgattg aaatgctgga tatgattagt tttgagttca atctacgtat agatgaatct   40200
acattagaac acattattac tattggagat cttatttctg tagtcaaaaa tagtacaaaa   40260
tcaatatagt aattgataag cattttttca tctatggagc tctcacatca gagctccaca   40320
agaatattat tcttttatcc aataaagata aattgcatca atccagctat taaaatagta   40380
atttttaaga ctaccgttga ctatcatcaa cagttacata caatcttgct cacactgcat   40440 ttaactttg tcaatataaa tcaatatgaa taaacagggt gtgatatggt ggatttgtgc    40500
aacgacttgt taagtataaa ggaaggccaa aagaaagagt ttacactcca ttctggtaat   40560
aaagtttcct ttatcaaagc caagattcct cataaaagga tccaagattt aaccttcgtc   40620
aaccaaaaaa cgaatgtacg cgatcaagaa tccctaacag aagaatcatt agccgatatc   40680
ataaaaacta taaagctaca acaattcttc cctgtaatag gaagggagat tgatggtaga   40740
attgaaattc tggatggcac tcgtagaaga gcatctgcaa tatatgcagg agcagatctt   40800
gaagttctat attcaaaaga atatatatct actcttgatg ccagaaaact agcaaacgat   40860
atacaaacag caaagagca tagcatccga gaacttggta ttggtcttaa ttttctgaaa   40920
gtatcaggga tgtcctataa agacatagcc aaaaagaga atctgtctcg cgcgaaagtc    40980
actcgtgcct ttcaggcagc aagcgttcca caggaaataa tatctctatt tccaatcgcg   41040
tcagaactta actttaatga ctacaagata ttattcaatt attataaagg acttgaaaag   41100
gctaatgaat ctcttagttc tacactacca atattaaagg aagaaataaa agaccttgat   41160
acaaatttgc ccccggacat atataaaaaa gaatttaa acatcataaa gaaaagcaaa    41220
aacagaaagc aaaacccttc gctaaaagtt gactcgttat ttatttctaa agacaaacgg   41280
acttacataa aagaaaaga gaataaaaca aacagaactc taatatttac attatctaaa   41340
ataaacaaaa cagttcagag agaaatagat gaagctattc gggatataat ttctcgccat   41400
ctatcgtctt cataaacatc gaacactgat gtaaactgcc caattcagat aataaaaatc   41460
ttcgttgaac ttgactttca gccggtgggg taattccgtc ggctatctgt tattcaatcc   41520
ccacgcactg tgtttcctta aaattacggt gaaaactcat accctgctga ccacgagaaa   41580
attatctggt gaaattagta atattcatat cattgaaaat gaattgtgca actaagggat   41640
gcggcatgat ggtcaaaatt ttatgtgaat atgagtgact ggccgaaaat attcagcgta   41700
tttttaatcg tttcaataaa aacagcgagg attagcagtc aacgctttta ctactcaatt   41760 tttttttacat ggtgataaac aaaaaaatcca ccattaacag acttcgttca cagtatcaaa  41820
aaagctttaa gaatatatta gcagatttct caaatataat tactgtttta ttctcctaat   41880
cttcccataa aatgaccgac ttacattatt ttataattat aaacaagttt gattttaaaa   41940
tcatattaat tattaacaag agatttattt ttctaacccc aaaagttatg cttggtcaaa   42000
gagtaactta taatatccat acccctcata gggcttacag tttaaattgc gggtataaaa   42060
tacatctatt ttcaaataaa ataaagcata ctccaattac aacgagtgac taaaataaaa   42120
atatcatcca agtcaatcac tgtttgctct gcaaatatg tcagccttct caaacttacc    42180
agcacttaaa tatttaagca cacaatcatt ccttgaggga gttcacttat ttcaagagaa   42240
acatttcgtc ttcccacaca actaatccgc ccaatatagc taaatttgta ctcagtaata   42300
tcatttgtta tgccccccac cccaaaatat tcaagctcct tcacagataa aaaacgacaa   42360
tttacaaagc ctcattagtt ataactatgg aaatacctat tttagtatat cctataaagt   42420
tagaattact tcttcttgca cctaattcca tagttgaaaa acaagaataa ttttctccta   42480
cagctggatc catatagctt ccatcaggtc tacacaacac ccagtggagg ccgacaggaa   42540
```

```
ctccaataaa ggatacagca acagcttcca aaactctttg gttagaagat aacacatctc   42600
gttgatgtac tatattacat cccatgccaa ttaataagtc ccttgcatcg ggataaataa   42660
aactaattac ttgcgaaaaa atgttacttt cttcaacgac ataagcattc aatccaagaa   42720
gcctcgtagc catgactatc ttatcaggca tagaataacc ggcatccgcg atattatctt   42780
tgtgtattct cggattataa ttaccactag ttattaagta taaatcccgc tcacaacgat   42840
tatccaaatc aagagaactc ttccttgtca tttcggacat agacccttttg tattgtggta   42900 ttttatcaac ccctaattcc tttgcagcac agagtaaact ggcagctcca caagaattgt   42960
catacatctg cttcctcgcc aaaaaacaac cttgttcgtt tactctattc tcatttaccc   43020
tcacatcagt ctgatgagat atcatatatt ctcttggtat agcccctgc aataaaaccc    43080 catataacat aacacctgta tgaatacatc cccgtttgca aggcttccgt tgttccgaca   43140
tcgacgagta attgcagcac agtattgcat ccagcaatgc gaactactat gagaattagc   43200
tgaccgggtc cttattcccc gaacgaactt taaatccaaa acctcatact cttttccgtc   43260
gtcatcacgt ccgtcaccat aacaaccttt cagcatccac ccttttatta agagttaatg   43320
tccatcagca tcagcaatta ataccgcctg atactgacat atttttgtcg tatttacgtc   43380
cataatcggt tattgtgata caggtcacac cagcttattt gctattgtta caataaccac   43440
cttggttgag agctgttttt tcaactttgt tatcaactcc cccaactcct tggtcagtaa   43500
ggctgccgac cgagcacagt gaatagatag tatccgcagg taccaccatg cttacttaat   43560
actcagaagg cgaacatatg aatatcctcc ttagttccta ttccgaagtt cctattctct   43620
agaaagtata ggaacttcga agcagctcca gcctacacgg cccgggcggc cgctcagctc   43680
cagtcttcag ttctcaggcc gcccacacgt tcaaattccc gggtgttatt agtcacaata   43740
atcagccccc gactgcgggc atgacctgcg atcatttgat caaatggccc gacagggcgt   43800
ccctgacggg caagttctgc tcttatctgg ccggtgtgtg tggctgcagc agcgtcgtaa   43860
tccagaacat caatgcggga aacaaatccc tcgatcacag cgagattacg ttcaggcatc   43920 tggcttttttt ctgcaccata tatcagctcc atcagggtga ccgaactgat acacattttc   43980
ccctggttca ggttaaaacg ctccctgacg ctggcgggtt tgttctttat cgtaaaaatg   44040
cagatgttgg tatcgagcat aaacttcagc atcagaatga ctcccttttct tgcatgccgg   44100 gctgttccct gttatccata aaatcggtgc tgacgctgtg tccgtcgaac cattcgtccc   44160
atgtctctcc ggctggcgta atgattctgg ttcgtccgac agcaatcact tcaacgcgtt   44220
ttacgttttc cggcaatgca accgcttttg gcagtctgac cgcctggctg cggttgctga   44280
gaaatacggt ggtttccatt atttgcctcc ttatgtggat atgtcttgtg tatatctatt   44340
gtgggattga tacccctaggc ctattaatat tccggagtat acgtagccgg ctaacgttaa   44400
caaccgcgat cgcacatgta catgatcaac aacaggtacc ttaaattttt ttatgatata   44460
agtaaaattt ctttggagtt ataccataat attcattaaa tttccttata aaataagatg   44520
ggcttgatat tccgataagt cttgatacat cattaatata gctttgacta ttcaataaaa   44580
gctttgctgc atgatgcatg cgaatatcaa gaaggatttg ttgaaatgtt aatttttcac   44640
tctccaatcg ttttctaaca gctatttctg ataaattcaa gttatttgaa atatcagaaa   44700
gacgccatct cttctcgatg ttttttttcaa caatcttcct tatctgatca gaaaaactaa   44760
gagaagaagc tatcgatatc gaagtatata aagcttcctc atcagaaaca gctgataaaa   44820
ggcaagctaa actatagatc tttctttttgc cgaaaggcat ctctttata gatttgaaca   44880
```

-continued

```
aatcgataga aacctcctcc tcagagagga ggaatatttt tttgtttaac cccctttttct  44940
cctcagaata ggagtgttga aatgaataaa ttggttccat tattctaata atgcttaata  45000
ataaatttct gtcaaggctt ataatctcaa atggattaat gctatcagat ttttttatgg  45060
agacgtttat ttgtatattt cgctctataa aagcaatttg cccttcatcg atagtcaaag  45120
tttcattgcc tgagctaacc gtcattgaac acctttttgc atataaaata atatagttat  45180
gcaagcgaac ctttatatct attttgtttt tatgtcccat atccatcata aattcaacag  45240
aatataccaa actatattta gtgtttacag agtaactaag aaatttctgt aacagtgatt  45300
gtatacaaaa tctttccgtt attaagatag attaagtaat ttttcctata tttaacttta  45360
tttacatttt ttgaagaaag agcttatgca gcttctattt ctctgtgcaa caagctaagt  45420
atttgcactg aaagggacta taaccatatt atggtttcac ttttcttagg caatatctgt  45480
gtaaatgttc ggaaaggagt ggagcttcgc aaaactccag catcataata tcctatacgg  45540
aacgcataaa gccccttcag actggaggct ccacaaatcc ggttggtgtt gatattggta  45600
agcgttaacc gaatgccgca ttgacgattc tcccgatgac agcgtt                45646
```

SHIGELLA-BASED MINIMAL PLASMID RECOMBINANT INVASION CONSTRUCT

RELATED APPLICATIONS

This application claims priority to U.S. Provisional Application No. 63/021,463, filed May 7, 2020, which is incorporated by reference in its entirety.

STATEMENT AS TO RIGHTS OR INVENTIONS MADE UNDER FEDERALLY SPONSORED RESEARCH AND DEVELOPMENT

The invention was made with government support from the Walter Reed Army Institute of Research, a subordinate organization of the United States Army Medical Research and Materiel Command. The United States Government has certain rights in the invention.

SEQUENCE LISTING

The instant application contains a Sequence Listing, which has been submitted electronically in ASCII format and is hereby incorporated by reference in its entirety. Said ASCII copy, created on May 3, 2021, is named "WRAIR_18_28_PCT_ST25.txt" and is 113,272 bytes in size.

BACKGROUND

Live, attenuated strains of bacteria have been successfully used as vaccines to protect humans and animals from disease. The successful vaccine strain is modified to reduce its ability to cause disease to an acceptable level while it retains sufficient pathogenic potential to stimulate a protective immune response in the vaccinated host. Therefore a delicate balance must be achieved as extensive attenuation generally results in reduced immunity.

*Shigella* is a genus of Gram-negative bacteria belonging to the family Enterobacteriaceae and the etiologic agent of bacillary dysentery or shigellosis, the symptoms of which include abdominal pain, diarrhea, fever, vomiting, and blood or mucus in the stool. *Shigella* is transmitted by a fecal-oral route, typically through contaminated food or water. As a result, *Shigella* is more of a public health threat in developing countries where proper sanitation and hygiene are lacking.

The development of an effective live, attenuated strain of *Shigella* to protect humans against bacillary dysentery (shigellosis) has been hampered by the inability to strike a balance between a need for the strain to invade the intestinal epithelium and reduction of pathogenicity to an acceptable level. Invasive strains that are protective tend to be "reactogenic," i.e., they cause diarrhea and/or fever in the host. The conventional approach to attenuate *Shigella* is to mutate or delete genes on the *Shigella* invasion plasmid in the hopes of reducing the reactogenicity of the vaccine strain while preserving immunogenicity. Levine, M. et al. 2007. Clinical trials of *Shigella* vaccines: two steps forward and one step back on a long, hard road. Nat Rev Microbial 5:540-553. This strategy is a "top-down" approach starting with a wild type, virulent strain of *Shigella*. Genes are then systematically inactivated until the strain is sufficiently attenuated to be clinically safe to administer yet still stimulate a robust immune response. For example, the attenuating mutation in *S. flexneri* 2a strain SC602 is a deletion of virG (icsA) which abolishes the ability of the bacterium to spread from cell to cell after invasion. Coster, T. S. et al. 1999. Vaccination against shigellosis with attenuated *Shigella flexneri* 2a strain SC602. Infect. Immun. 67:3437-3443. A gene on the invasion plasmid that encodes an enterotoxin and another enterotoxin gene on the chromosome were targets in construction of *S. flexneri* 2a strain CVD1207 leading to attenuation and reduced reactogenicity. Kotloff, K. L. et al. 2000. *Shigella flexneri* 2a strain CVD 1207, with specific deletions in virG (icsA), sen, set, and guaBA, is highly attenuated in humans. Infect Immun 68:1034-1039. A major disadvantage of this strategy is that the attenuated strains that are protective have the undesirable side effect of causing diarrhea and/or fever. Further, to achieve the appropriate balance in the approach between preserving immunogenicity and reducing reactogenicity, other genes on the invasion plasmid (also known as the virulence plasmid), and possibly the chromosome as well, that may contribute to reactogenicity must be identified and inactivated.

An alternate strategy is disclosed in U.S. Pat. No. 9,434,772. Vectors described in this application were designed starting with the minimal set of genes from the *Shigella* invasion plasmid that mediate invasion of and multiplication within host epithelial cells. These genes were cloned into a plasmid to produce *Shigella* minimal invasion plasmid (SMIP). The SMIP can be transferred into a plasmid-cured strain of *Shigella* or an enteroinvasive *Escherichia coli* (EIEC), where it can be used as a vaccine strain. Additionally, the SMIP can serve as a platform to which other genes can be added in an attempt to improve immunogenicity of the vaccine strain. This strategy is an improvement over the "top-dawn" strategy because it allows one to directly determine the contribution of any putative virulence gene by adding it back to the SMIP, i.e., the role of the gene can be measured in the context of the minimal gene complement required for invasion rather than in the larger context of all of the genes normally present on the invasion plasmid.

Inventors have discovered a different approach using PRISM and PRISM-G minimal plasmid constructs described in this application provide an improved platform for developing a live, attenuated vaccine strain of *Shigella* or enteroinvasive *Escherichia coli* (EIEC), that achieves the balance between immunogenicity and reduced reactogenicity in patients. In addition to inserting other *Shigella* or EIEC genes into the recombinant *Shigella* minimal invasion plasmid, it is also possible to insert a gene that encodes an immunogenic protein from a pathogen other than *Shigella* or EIEC or some other non-*Shigella* or non-EIEC protein of interest. In other words, a pRISM and PRISM-G *Shigella* or EIEC strain comprising the recombinant *Shigella* minimal invasion plasmid can be used as a broad antigen delivery system for delivering any antigen of interest. *Shigella* or EIEC invasion into colonic mucosa stimulates a strong immune response in the intestinal mucosa. Furthermore, *Shigella* or EIEC invasion in the colon can also stimulate lymphoid tissues adjacent to the colon, and, thus, it could stimulate a strong mucosal immune response in the reproductive tract. Thus, the recombinant *Shigella* minimal invasion plasmid can be used as a live vaccine platform for delivery or expression of recombinant antigens in host cells. That is, the recombinant *Shigella* minimal invasion plasmid can be used as a vehicle for delivering DNA vaccines to mucosal lymphoid tissues or for expression and delivery of recombinant antigens. As such, the recombinant *Shigella* minimal invasion plasmid can be used in methods of inducing an immune response in a subject. In one embodiment, the immune response is directed to *Shigella*. In other embodiments, the immune response is directed to a bacterial, viral, fungal, parasitic, or mammalian protein of interest.

SUMMARY

It has been discovered that the recombinant *Shigella* minimal invasion plasmid constructs pRISM and pRISM-G can be used as a vehicle for delivering DNA vaccines to mucosal lymphoid tissues or for expression and delivery of recombinant antigens. As such, the recombinant *Shigella* minimal invasion plasmid can be used in methods of inducing an immune response in a subject.

In one embodiment, the immune response is directed to *Shigella*. In other embodiments, the immune response is directed to a bacterial, viral, fungal, parasitic, or mammalian protein of interest.

A recombinant *Shigella* minimal invasion plasmid construct, pRISM. In some embodiments, PRISM comprises SEQ ID NO: 1. A recombinant *Shigella* minimal invasion plasmid constructs pRISM-G. In some embodiments, pRISM-G comprises SEQ ID NO: 2. In one embodiment A composition comprising the *Shigella* or *E. coli* bacterium comprising a recombinant *Shigella* minimal invasion plasmid constructs PRISM and a pharmaceutically acceptable excipient. A composition comprising the *Shigella* or *E. coli* bacterium comprising a recombinant *Shigella* minimal invasion plasmid constructs pRISM-G and a pharmaceutically acceptable excipient.

A vaccine composition comprising the *Shigella* or *E. coli* bacterium comprising a recombinant *Shigella* minimal invasion plasmid constructs PRISM and at least one pharmaceutically acceptable adjuvant.

A vaccine composition comprising the *Shigella* or *E. coli* bacterium comprising a recombinant *Shigella* minimal invasion plasmid constructs pRISM-G and at least one pharmaceutically acceptable adjuvant.

A method of inducing an immune response to *Shigella* in a subject, the method comprising the step of: administering a composition further comprising a recombinant *Shigella* minimal invasion plasmid construct PRISM or pRISM-G to the subject in an amount sufficient to induce an immune response to *Shigella* in the subject.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 1 shows a plasmid map of a recombinant *Shigella* minimal invasion plasmid construct, pRISM (SEQ ID NO: 1).

FIG. 2 shows a plasmid map of a recombinant *Shigella* minimal invasion plasmid construct, pRISM-G (SEQ ID NO: 2).

FIG. 3 shows PRISM construct colony D1 used for DNA preparation.

FIG. 4 shows pRISM-G construct colony D1 used for DNA preparation.

FIGS. 5A and 5B show growth curves of pRISM constructs compared to the virulence plasmid-cured *Shigella* strain BS103 and SMIP (FIG. 5A) and SMIP-G (FIG. 5B).

FIG. 6 shows mean titers of serum IgA responses in naive guinea pigs or guinea pigs immunized with pRISM or pRISM-G assayed by ELISA from serum and eyewash samples collected on Day 0, Day 28 and Day 56. Upper and lower error bars together represent one standard deviation from the GMT. A. Serum IgA response to Invaplex. B. Serum IgA response to LPS.

FIG. 7 shows mean titers of serum IgG responses in naive guinea pigs or guinea pigs immunized with PRISM or pRISM-G assayed by ELISA from serum and eyewash samples collected on Day 0, Day 28 and Day 56. Upper and lower error bars together represent one standard deviation from the GMT. A. Serum IgA response to Invaplex. B. Serum IgA response to LPS.

FIG. 8 shows mean titers of mucosal IgA responses in naive guinea pigs or guinea pigs immunized with pRISM or pRISM-G assayed by ELISA from serum and eyewash samples collected on Day 0, Day 28 and Day 56. Upper and lower error bars together represent one standard deviation from the GMT. A. Serum IgA response to Invaplex. B. Serum IgA response to LPS.

FIG. 9 depicts average results of two colonies/*Shigella* minimal plasmid strains for the ability to invade HeLa epithelial cells in a gentamicin protection assay. Invasiveness is plotted as percentages of the invasiveness of a wild-type 2457T Congo red-positive invasion-positive isolate. BS103 is a Congo red-negative invasion negative colony.

FIG. 10 shows that pRISM and pRISM-G constructs are invasive and comparable to SMIP and SMIP-G constructs.

DETAILED DESCRIPTION

Reference will now be made in detail to various exemplary embodiments. It is to be understood that the following detailed description is provided to give the reader a fuller understanding of certain embodiments, features, and details of aspects of the invention, and should not be interpreted as a limitation of the scope of the invention. In order that the present invention may be more readily understood, certain terms are first defined. Additional definitions are set forth throughout the detailed description.

*Shigella* is a genus of Gram-negative bacteria belonging to the family Enterobacteriaceae and the etiologic agent of bacillary dysentery or shigellosis, the symptoms of which include abdominal pain, diarrhea, fever, vomiting, and blood or mucus in the stool. There are four species of *Shigella: Shigella dysenteriae, Shigella flexneri, Shigella boydii*, and *Shigella sonnei* (also referred to as serogroups A, B, C, and D, respectively). *Shigella* is transmitted by a fecal-oral route, typically through contaminated food or water. *Shigella* is very closely related to enteroinvasive *Escherichia coli* (EIEC), which also cause dysentery, with recent evidence suggesting that *Shigella* and EIEC are derived from multiple origins of *E. coli* and form a single pathovar. Yang et al., (2005) Nucleic Acids Res., 33 (19): 6445-58. Certain O-antigens associated with EIEC are identical to those found in *Shigella* spp. and many plasmid-associated virulence determinants are common to both EIEC and *Shigella*. Id. *Shigella* and EIEC invade colonic epithelial multiply intracellularly, and spread to neighboring cells. The genetic elements responsible for these invasive properties are located on the bacterial chromosome and on a large (about 220 kb) plasmid called the invasion or virulence plasmid that is unique to the virulent strains of *Shigella* and EIEC. *Shigella* variants that have lost the invasion plasmid also lose their invasive properties. In addition to the invasion plasmid, many chromosomal genes also contribute to virulence, including set1A, set1B (enterotoxin), iucA-D (aerobactin production and transport), iutA (iron uptake), pic (serine protease/mucinase), and sigA (protease).

Virulence of *Shigella* is dependent on temperature. At 37° C. *Shigella* are fully virulent, whereas at 30° C. *Shigella* lose the ability to both invade epithelial cells and provoke keratoconjunctivitis in guinea pigs. Maurelli et al., (1984) Infect. Immun. 43 (1): 195-201. When *Shigella* grows at 37° C., the VirF protein induces the expression of the VirB protein, which in turn activates the ipa, mxi, and spa promoters, causing the activation of the spa and mxi operons. This results in the synthesis of a protein complex called the Mxi-Spa translocon. Contact between the bacterium and the host epithelial cell activates the translocon, leading to the secretion of invasion plasmid antigens (Ipa). IpaA, IpaB, and IpaC form a complex that interacts with the cellular membrane and induces a signal cascade that causes the bacterium to be internalized into the cytoplasm via an endosome. The Ipa proteins also mediate the release of the bacterium from the endosome.

Figure 5A:
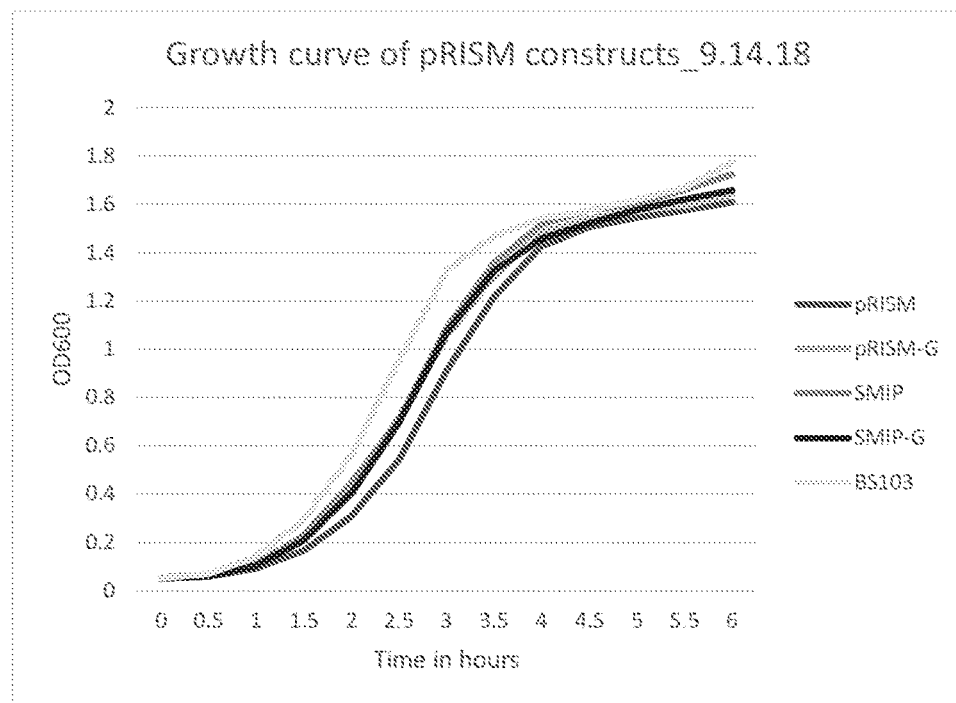
Figure 5B:
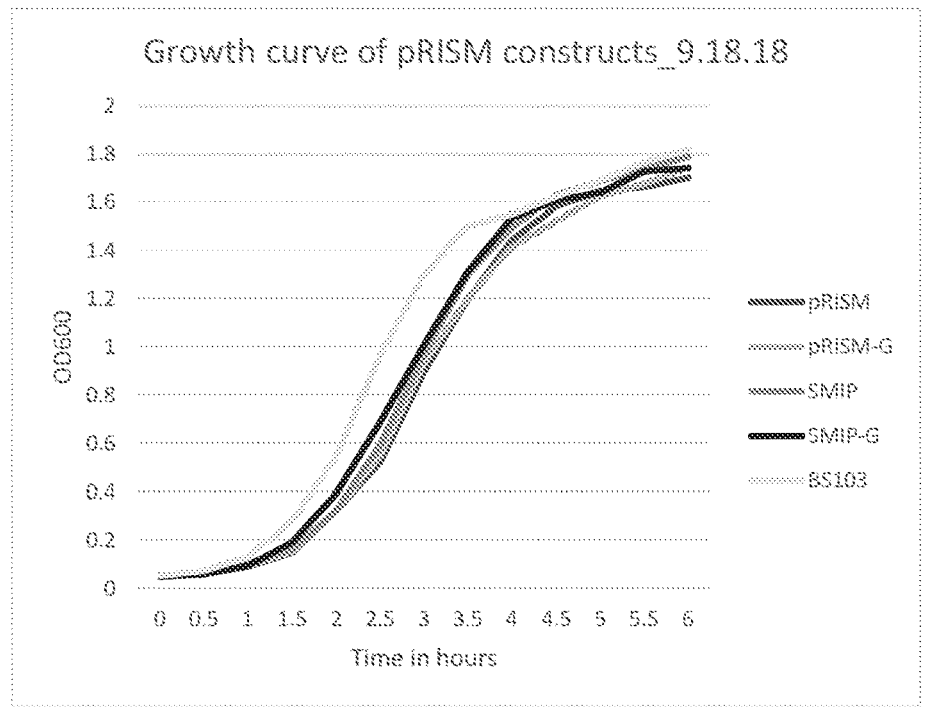

A cell entry region of about 30 kb is generally conserved in invasion plasmids and includes the mxi-spa gene locus, the virB gene, the ipa gene locus, and the ipg gene locus. Yang et al., (2005) Nucleic Acids Res., 33 (19) 6445-58. See FIG. 5. The cell entry region is bracketed by insertion sequence 100 and insertion sequence 600 in all invasion plasmids, suggesting the transmission of a common invasion plasmid in *Shigella* or the transmission of a cell entry region to all invasion plasmids from a common source. Yang et al., (2005) Nucleic Acids Res., 33 (19): 6445-58. The cell entry region has the markings of a typical pathogenicity island (PAI), such as G+C content distinctly different from the surrounding genes, indicating genetic instability. The remaining .about. 190 kb of virulence plasmid DNA sequence has a mosaic character. It contains genes related to IncFIIA-type plasmids. In addition, the plasmid is littered with copies of IS elements and remnants of IS elements that account for 53% of the open reading frames on the plasmid as well as a class of virulence genes known as the osp genes. These virulence genes encode secreted effector molecules that are transported by the type III secretion system (T3SS). Given the unusual mosaic makeup of the virulence plasmid, it is likely that it was formed by sequential gene acquisition and possibly gene duplication and rearrangement. The presence of three separate and distinct ospD genes on the *S. flexneri* 2a plasmid is evidence that argues for gene duplication after gene acquisition. In any event, it is apparent that the virulence plasmid present in contemporary strains of *Shigella* spp. arose in a step-wise fashion.

In addition to invasion, a fully virulent strain of *Shigella* has several other hallmark phenotypes, including intracellular replication, intercellular spread, the ability to induce apoptosis in macrophages, the ability to protect a host mammalian cell from apoptosis, the ability to signal polymorphonuclear leukocyte migration across a model monolayer of polarized epithelial cells, and the ability to generate a strong inflammatory reaction in the guinea pig model for keratoconjunctivitis (Sereny test). Post-invasion phenotypes are important for full virulence and the state of the art for identifying genes responsible for these phenotypes has been to inactivate a gene and test for loss or reduction of virulence phenotypes.

The present disclosure provides a recombinant vector comprising the cell entry region of a *Shigella* or EIEC invasion plasmid and a virF gene from a *Shigella* or EIEC invasion plasmid and optionally a selection gene. In one embodiment, the cell entry region is from a *Shigella flexneri* invasion plasmid. In yet another embodiment, the recombinant vector comprises an ipa gene locus from a *Shigella* or EIEC invasion plasmid, an ipg gene locus from a *Shigella* or EIEC invasion plasmid, a virB gene from a *Shigella* or EIEC invasion plasmid, a mxi-spa gene locus from a *Shigella* or EIEC invasion plasmid, and a virF gene from a *Shigella* or EIEC invasion plasmid. The recombinant vector is capable of directing the expression of genes that have been inserted into the vector. Thus, in certain aspects, the recombinant vector further comprises a nucleic acid encoding one or more foreign proteins, including, for example, one or more bacterial viral, fungal, parasitic, or mammalian proteins, or an immunogenic portion thereof. The recombinant vector can be used to express any protein of interest. In one embodiment, the protein is from an enterohemorrhagic or enterotoxigenic *E. coli*, including, but not limited to the intimin protein, the colonization factor antigen I fimbrial adhesion, or the heat labile toxin (LT) subunit B. In another embodiment, the protein is from *Salmonella*, including, for example, a type III secretion system-1 secreted protein.

The nucleic acid encoding the one or more bacterial, viral, fungal, parasitic, or mammalian proteins, or an immunogenic portion thereof or the one or more *Shigella* or EIEC proteins, or an immunogenic portion thereof, may be inserted into a replicable vector for cloning (amplification of the DNA) or for expression. Various vectors are publicly available. The appropriate nucleic acid sequence may be inserted into the vector by a variety of procedures known in the art. For example, DNA may be inserted into an appropriate restriction endonuclease site(s) in the vector using techniques known in the art. As compared to other mutated *Shigella* invasion plasmids (Coster, T. S. et al., Infect. Immun. 67:3437-3443; Kotloff, K. L. et al. 2000. Infect Immun 68:1034-1039. Levine, M. M. et al., Nat Rev Microbiol 5:540-553), the recombinant vectors provided in this application contain a substantially smaller portion of the invasion plasmid. In one embodiment, the recombinant vector comprises no more than about 30, 40, 50, 60, 70, 80, 90, 100, 110, 120, 130, 140, 150, 160, 170, 180, 190, or 200 kilobase pairs of a *Shigella* or EIEC invasion plasmid. Preferably the recombinant vector comprises no more than about 30-50 kilobase pairs of the invasion plasmid. The recombinant vectors disclosed herein can also be much smaller in overall size than the mutated invasion plasmids generated using a conventional approach. Thus, in certain embodiments, the recombinant vector has no more than about 40, 50, 60, 70, 80, 90, 100, 110, 120, 130, 140, 150, 160, 170, 180, 190, or 200 kilobase pairs. Preferably the recombinant vector has no more than about 40-100 kilobase pairs. More preferably the recombinant vector has no more than about 40-60 kilobase pairs.

Suitable vectors may be chosen or constructed to contain appropriate regulatory sequences, including promoter sequences, terminator sequences, enhancer sequences, a selection gene, and other sequences. Typical selection genes encode proteins that (a) confer resistance to antibiotics or other toxins, e.g., ampicillin, neomycin, kanamycin, chloramphenicol, or tetracycline, (b) complement auxotrophic deficiencies, or (c) supply critical nutrients not available from complex media, e.g., the gene encoding D-alanine racemase. Such selection genes are well known in the art. Construction of suitable vectors containing one or more of these regulatory sequences employs standard ligation techniques which are known to the skilled artisan. See e.g., Sambrook et al., Molecular Cloning: A Laboratory Manual, 3rd ed., Cold Spring Harbor Laboratory Press (2001). Many established techniques used with vectors, including the manipulation, preparation, mutagenesis, sequencing, and transfection of DNA, are described in Current Protocols in Molecular Biology, Ausubel et al. eds., John Wiley & Sons (2010).

The invention further provides a host cell that comprises at least one recombinant vector described herein. Systems for cloning and expressing polypeptides in a variety of host cells are known in the art. Suitable host cells include mammalian cells, insect cells, plant cells, yeast cells, or prokaryotic cells, e.g., *E. coli*. Preferably the host cell is a bacterium. In some embodiments, the host cell is a *Shigella* (e.g., *Shigella dysenteriae, Shigella flexneri, Shigella boydii,* and *Shigella sonnei*) or EIEC bacterium comprising the recombinant vector described in this application. In one embodiment, the *Shigella* or EIEC bacterium is a plasmid-cured bacterium that does not contain an invasion plasmid. A further aspect of the disclosure provides a method of introducing the recombinant vector into a host cell. For eukaryotic cells, suitable transfection techniques may include calcium phosphate, DEAE-Dextran, electroporation, or liposome-mediated transfection. For bacterial cells, suitable techniques may include, but are not limited to, calcium chloride transformation, electroporation, and transfection using bacteriophage. These techniques are well known in the art. See e.g., Current Protocols in Molecular Biology, Ausubel et al. eds., John Wiley & Sons (2010). DNA introduction may be followed by a selection method (e.g., antibiotic resistance) to select cells that contain the vector.

The vectors and bacterial strains disclosed in this invention provide an improved platform for developing an attenuated vaccine strain of *Shigella* or EIEC that achieves the balance between immunogenicity and reduced reactogenicity in a subject. In one embodiment, the attenuated strain is a plasmid-cured *Shigella* or EIEC comprising a recombinant vector as described in this application (hereinafter referred to as "vaccine strain"). As noted above, in one embodiment, the recombinant vector of the vaccine strain further comprises a nucleic acid encoding one or more foreign proteins, including, for example, one or more bacterial, viral, fungal, parasitic, or mammalian proteins, or an immunogenic portion thereof. As noted above, in another embodiment, the recombinant vector of the vaccine strain further comprises a nucleic acid encoding one or more *Shigella* or EIEC proteins, or an immunogenic portion thereof. Also disclosed is a composition comprising the vaccine strain, at least one pharmaceutically acceptable excipient, and optionally an adjuvant (hereinafter referred to as "vaccine composition").

The pharmaceutically acceptable excipient can be chosen from, for example, diluents such as starch, microcrystalline cellulose, dicalcium phosphate, lactose, sorbitol, mannitol, sucrose, methyl dextrins; binders such as povidone, hydroxypropyl methylcellulose, dihydroxy propylcellulose, and sodium carboxymethylcellulose; and disintegrants such as crospovidone, sodium starch glycolate, croscarmellose sodium, and mixtures of any of the foregoing. The pharmaceutically acceptable excipient can further be chosen from lubricants such as magnesium stearate, calcium stearate, stearic acid, glyceryl behenate, hydrogenated vegetable oil, glycerine fumerate and glidants such as colloidal silicon dioxide, and mixtures thereof. In some embodiments of the present invention, the pharmaceutically acceptable excipient is chosen from microcrystalline cellulose, starch, talc, povidone, crospovidone, magnesium stearate, colloidal silicon dioxide, sodium dodecyl sulfate, and mixtures of any of the foregoing. The excipients of the present invention can be intragranular, intergranular, or mixtures thereof.

The vaccine composition can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form. After formulation, the vaccine composition can be incorporated into a sterile container which is then sealed and stored at a low temperature (e.g., 4° C.), or it can be freeze dried. The vaccine composition can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccine composition can comprise agents that enhance the protective efficacy of the vaccine, such as adjuvants. Adjuvants include any compound or compounds that act to increase an immune response to *Shigella* or to any antigen delivered by the recombinant vector, thereby reducing the quantity of antigen necessary in the vaccine, and/or the frequency of administration necessary to generate a protective immune response. Adjuvants can include for example, emulsifiers, muramyl dipeptides, pyridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), Mycobacterialphlei (*M. phlei*) cell wall extract (MCWE) (U.S. Pat. No. 4,744,984), *M. phlei* DNA (M-DNA), and *M. phlei* cell wall complex (MCC). Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonium bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (PCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp. Immunomodulatory cytokines can also be used in the vaccine compositions to enhance vaccine efficacy, for example, as an adjuvant. Non-limiting examples of such cytokines include interferon alpha (IFN-.alpha.) interleukin-2 (IL-2), and granulocyte macrophage-colony stimulating factor (GM-CSF), or combinations thereof. The vaccine composition can be prepared using techniques well known to those skilled in the art including, but not limited to, mixing, sonication and microfluidation. The adjuvant can comprise from about 10% to about 80% (v/v) of the vaccine composition, more preferably about 20% to about 50% (v/v), and more preferably about 20% to about 30% (v/v), or any integer within these ranges.

The vaccine composition can be administered to any animal, and preferably is a mammal such as a human, mouse, rat, hamster, guinea pig, rabbit, cat, dog, monkey, cow, horse, pig, and the like. Humans are a preferred embodiment. Administration of the vaccine composition can be by infusion or injection (e.g., intravenously, intramuscularly, intracutaneously, subcutaneously, intrathecal, intraduodenally, intraperitoneally, and the like). The vaccine composition can also be administered intranasally, vaginally, rectally, orally, intratonsilar, or transdermally. Additionally, the vaccine composition can be administered by "needle-free" delivery systems. The effective amount of the vaccine composition may be dependent on any number of variables, including without limitation, the species, breed, size, height, weight, age, overall health of the patient, the type of formulation, or the mode or manner or administration. The appropriate effective amount can be routinely determined by those of skill in the art using routine optimization techniques and the skilled and informed judgment of the practitioner and other factors evident to those skilled in the art. Preferably, a therapeutically effective dose of the vaccine composition described herein will provide the therapeutic preventive benefit without causing substantial toxicity to the subject. The vaccine composition can be administered to a patient on any schedule appropriate to induce and/or sustain an immune response against *Shigella* or any other protein of interest. For example, patients can be administered a vaccine composition as a primary immunization as described and exemplified herein, followed by administration of a secondary immunization, or booster, to bolster and/or maintain protective immunity. The vaccine administration schedule, including primary immunization and booster administration, can continue as long as needed for the patient, for example, over the course of several years, to over the lifetime of the patient. The frequency of primary vaccine and booster administration and dose administered can be tailored and/or adjusted to meet the particular needs of individual patients, as determined by the administering physician according to any means suitable in the art. The vaccine composition may be administered prophylactically (before exposure to *Shigella*, EIEC, or other foreign pathogen) or therapeutically (after exposure to *Shigella*, EIEC, or other foreign pathogen).

In another aspect, the vaccine strain or vaccine composition can be used in a method of inducing an immune response. The immune response can be induced in a naive subject who has not previously been exposed to *Shigella* or EIEC (or some other foreign pathogen). Alternatively, the immune response can be induced in a subject who has been previously exposed to *Shigella* or EIEC (or some other foreign pathogen) and used to enhance an existing immune response. In one embodiment, the method comprises administering to a subject a vaccine strain or a vaccine composition, wherein the administration of the vaccine strain or the vaccine composition induces an immune response against a protein, or immunogenic portion thereof, encoded by the recombinant vector in the vaccine strain or the vaccine composition.

In certain embodiments, the recombinant vector comprises a nucleic acid encoding a foreign protein, or an immunogenic portion thereof, as discussed previously. In other embodiments, the recombinant vector comprises a nucleic acid encoding a *Shigella* or EIEC protein, or an immunogenic portion thereof, as discussed previously. Alternatively, the recombinant vector may comprise a first nucleic acid encoding a foreign protein, or immunogenic portion thereof, and a second nucleic acid encoding a *Shigella* or EIEC protein, or immunogenic portion thereof. One embodiment is directed to a method of inducing an immune response against *Shigella* or EIEC in a subject, the method comprising administering to the subject a vaccine strain or a vaccine composition in an amount sufficient to induce an immune response to *Shigella* or EIEC in the subject. In certain aspects, the vaccine strain or the vaccine composition induces significantly less transepithelial migration of polymorphonuclear neutrophils (PMNs), as compared to the 2457T *Shigella flexneri* strain or, in certain embodiments, does not induce transepithelial migration of PMNs. Transepithelial migration of PMNs can be measured using routine methods, such as those described in this application.

Another embodiment is directed to a method of inducing an immune response to a bacterial, viral, fungal, parasitic, or mammalian protein in a subject, the method comprising administering to the subject a vaccine strain or a vaccine composition in an amount sufficient to induce an immune response to the bacterial, viral, fungal, parasitic, or mammalian protein in the subject. In these methods of inducing an immune response, the immune response can be measured using routine methods in the art, such as those disclosed in this application. These routine methods include, but are not limited to, measuring an antibody response, such as an antibody response directed against the protein encoded by the recombinant vector, and measuring cellular proliferation, including, for example, by measuring tritiated thymidine incorporation or cytokine (e.g., IFN-gamma.) production.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1 pRISM Construct

Construction of a recombinant *Shigella* minimal invasion plasmid construct, PRISM (SEQ ID NO: 1.)

A core plasmid called SMIP for *Shigella* minimum invasion plasmid was constructed comprising the following features, as summarized in FIG. 1 (SEQ ID NO: 1).

Example 2 pRISM-G Construct

Construction of a recombinant *Shigella* minimal invasion plasmid construct, pRISM-G A core plasmid called SMIP for *Shigella* minimum invasion plasmid was constructed comprising the following features, as summarized in FIG. 2 (SEQ ID NO: 2).

PRISM construct colony D1 used for DNA preparation (FIG. 3). PRISM-G construct colony D1 used for DNA preparation (FIG. 4).

HeLa cell invasion assay: Live attenuated strains of *Shigella* are expected to retain the ability to invade non-phagocytic cells in order to generate protective immune responses in the host. The *Shigella* minimal plasmid constructs that invade and become intracellular will be protected from the effects of gentamicin whereas extracellular bacteria will be killed. PRISM and pRISM-G minimal plasmid constructs in a non-invasive *Shigella* background were evaluated for their invasiveness by the gentamycin protection assay with Hela cells. Alongside, wild type invasive *S. flexneri* 2a strain 2457T, non-invasive strain BS103 (positive and negative controls respectively) and SMIP and SMIP-G were also tested.

Gentamicin protection assay with Hela cells was performed as follows. HeLa monolayers were grown to semi-confluence in a 75 $cm^2$ flask in complete medium (cMEM) containing 10% heat-inactivated fetal bovine serum, 2 mM L-glutamine and 2 mM pyruvate. One flask was trypsinized with 0.25% trypsin and concentration of cells was adjusted to $2\times10^5$ cells/ml in cMEM. Twenty four well-plates were seeded with 2 ml of Hela cells and grown overnight at 37° C. in 5% $CO_2$. Log phase cultures of bacteria (grown in LB medium with appropriate antibiotics for strain maintenance if needed) were added at an estimated multiplicity of infection of 10. After addition of bacteria, the plate was centrifuged in a Sorvall swinging bucket rotor at 500×g for 5 minutes at 25° C. and the plate was incubated at 37° C. in 5% $CO_2$ for 1.5 h. The plates were washed three times with Hank's balanced salt solution and then incubated with cMEM containing 50 μg/ml gentamycin for 2 h at 37° C. in 5% $CO_2$. Hela cells were then lysed in a 0.1% Triton X-100 solution in PBS for 10 minutes. The bacteria in the lysate were plated on Tryptic Soy Agar plates and bacterial colonies counted after growth at 37° C. for 18 h. The figure below shows that pRISM and pRISM-G constructs are invasive and comparable to SMIP and SMIP-G constructs.

*Shigella* minimal plasmid strains were tested for the ability to invade HeLa epithelial cells in a gentamicin protection assay. Invasiveness is plotted as percentages of the invasiveness of a wild-type 2457T Congo red-positive invasion-positive isolate. BS103 is a Congo red-negative invasion negative colony. Average for two colonies/strain are shown in FIG. 9.

HeLa cell invasion assay: Live attenuated strains of *Shigella* are expected to retain the ability to invade non-phagocytic cells in order to generate protective immune responses in the host. The *Shigella* minimal plasmid constructs that invade and become intracellular will be protected from the effects of gentamicin whereas extracellular bacteria will be killed. PRISM and pRISM-G minimal plasmid constructs in a non-invasive *Shigella* background were evaluated for their invasiveness by the gentamycin protection assay with Hela cells. Alongside, wild type invasive *S. flexneri* 2a strain 2457T, non-invasive strain BS103 (positive and negative controls respectively) and SMIP and SMIP-G were also tested.

Gentamicin protection assay with Hela cells was performed as follows. HeLa monolayers were grown to semi-confluence in a 75 $cm^2$ flask in complete medium (cMEM) containing 10% heat-inactivated fetal bovine serum, 2 mM L-glutamine and 2 mM pyruvate. One flask was trypsinized with 0.25% trypsin and concentration of cells was adjusted to $2\times10^5$ cells/ml in cMEM. Twenty four well-plates were seeded with 2 ml of Hela cells and grown overnight at 37° C. in 5% $CO_2$. Log phase cultures of bacteria (grown in LB medium with appropriate antibiotics for strain maintenance if needed) were added at an estimated multiplicity of infection of 10. After addition of bacteria, the plate was centrifuged in a Sorvall swinging bucket rotor at 500×g for 5 minutes at 25° C. and the plate was incubated at 37° C. in 5% $CO_2$ for 1.5 h. The plates were washed three times with Hank's balanced salt solution and then incubated with cMEM containing 50 μg/ml gentamycin for 2 h at 37° C. in 5% $CO_2$. Hela cells were then lysed in a 0.1% Triton X-100 solution in PBS for 10 minutes. The bacteria in the lysate were plated on Tryptic Soy Agar plates and bacterial colonies counted after growth at 37° C. for 18 h. FIG. 10 shows that pRISM and pRISM-G constructs are invasive and comparable to SMIP and SMIP-G constructs.

*Shigella* minimal plasmid strains were tested for the ability to invade HeLa epithelial cells in a gentamicin protection assay. Invasiveness is plotted as percentages of the invasiveness of a wild-type 2457T Congo red-positive invasion-positive isolate. BS103 is a Congo red-negative invasion negative colony. Average for two colonies/strain are shown.

Growth curves of pRISM constructs compared to the virulence plasmid-cured *Shigella* strain BS103 and SMIP and SMIP-G. PRISM and SMIP constructs were transformed into BS103 (FIGS. 5A and 5B).

Immunogenicity and Efficacy of pRISM and pRISM-G Constructs:

Guinea pigs were immunized ocularly on Day 0 and day 14 with ~$1\times10^8$ CFUs of either PRISM or PRISM-G while the control group received only saline. Eyes were observed and scored for disease 4 days post-treatment. Serum and eye wash samples were collected from all the guinea pigs on Day 0 (pre-immune sample) and Day 28 (2 weeks after the second immunization) for immune responses. One month after the second immunization, the three groups were ocularly challenged with ~$1\times10^5$ CFUs of virulent *Shigella flexneri* strain 2457T to determine vaccine efficacy. The eyes were scored for disease (intensity of keratoconjunctivitis or Sereny reaction) for 4 days post-challenge. The protective efficacy of the pRISM constructs were assessed using a scoring criteria established in the lab. The guinea pig eyes which were immunized with PRISM or PRISM-G showed an overall protective efficacy of 92% ($p<0.0557$) and 100% ($p<0.0096$) respectively compared to the control group. The guinea pigs were euthanized at the end of the scoring period on Day 56 when serum samples were collected by heart bleed.

SBA is a measure of antibodies capable of killing *Shigella* in a serotype-specific manner in the presence of exogenous complement. SBA titers are used as a measure of immune response and vaccine efficacy. Serum bactericidal activity (SBA) assay was conducted on serum samples from Day 0, day 28 and Day 56 and eye wash samples of guinea pigs on Day 0 and Day 28. Results of the assays are shown below in Table 1.

TABLE 1

|  |  | Serum | | Eyewash | |
| --- | --- | --- | --- | --- | --- |
|  |  | Avg KI* | Fold increase over baseline | Avg KI* | Fold increase over baseline |
| PRISM | Day 0 | 20 |  | 20 |  |
|  | Day 28 | 869 | 43 | 2991 | 150 |
|  | Day 56 | 4868 | 234 |  |  |
| PRISM-G | Day 0 | 20 |  | 20 |  |
|  | Day 28 | 458 | 23 | 2430 | 122 |
|  | Day 56 | 8956 | 448 |  |  |
| Control | Day 0 | 20 |  | 20 |  |
|  | Day 28 | 23 | 0 | 20 |  |
|  | Day 56 | 399 | 20 |  |  |

*Killing Index when 50% of bacteria are killed by the serotype specific antibody SBA titers clearly show a serotype-specific killing response after receiving two doses of the vaccine on day 28 in serum and mucosal samples of guinea pigs immunized with pRISM and pRISM-G constructs.

Figure 6:
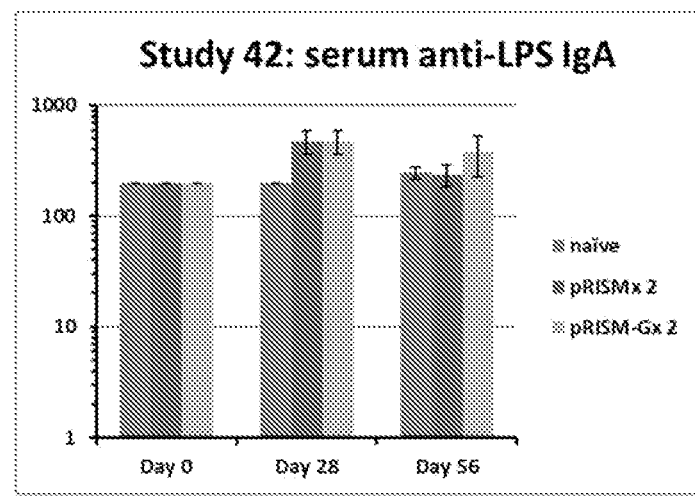
Figure 6:
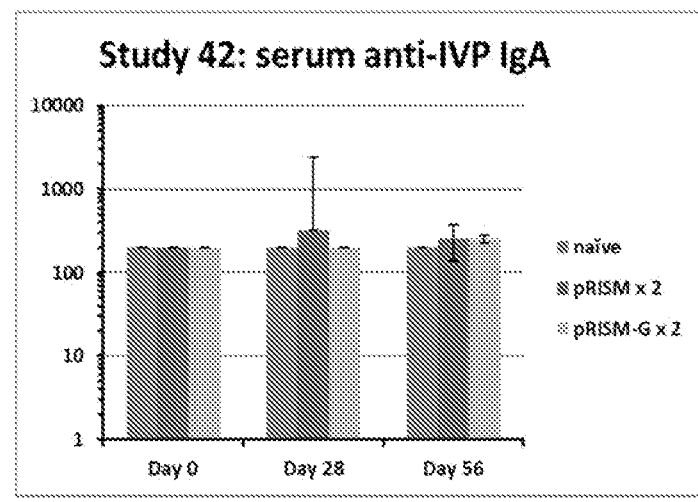
Figure 7:
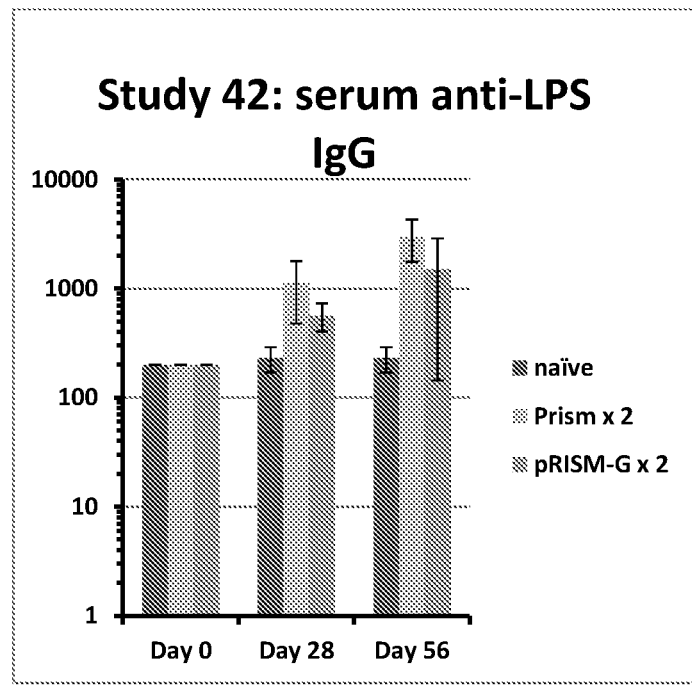
Figure 7:
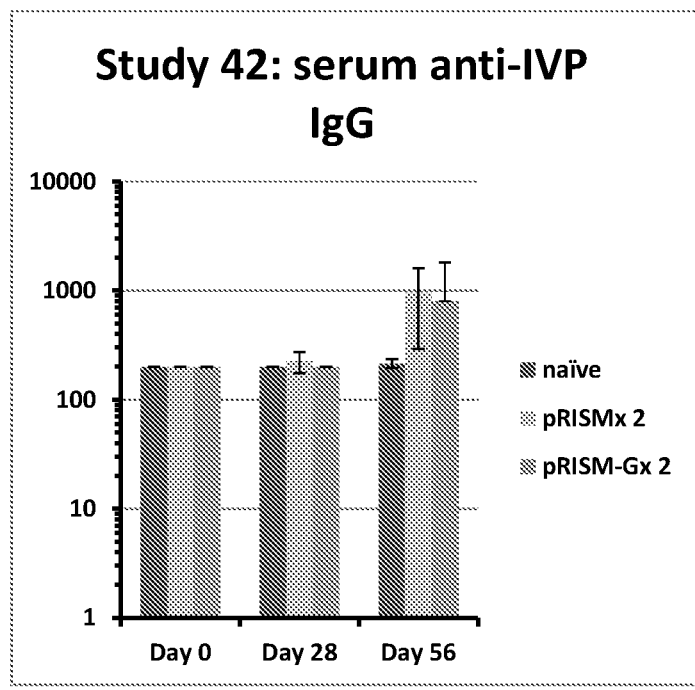
Figure 8:
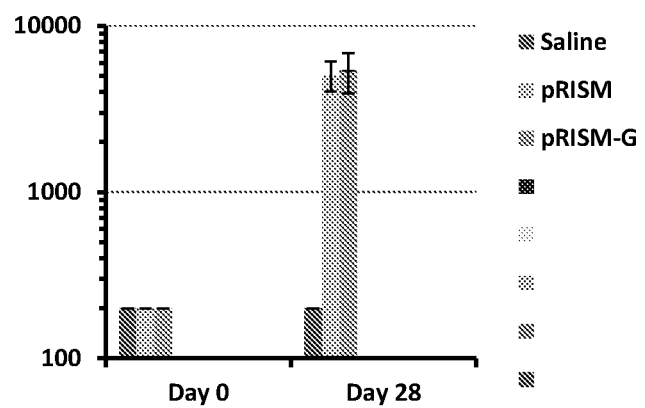
Figure 8:
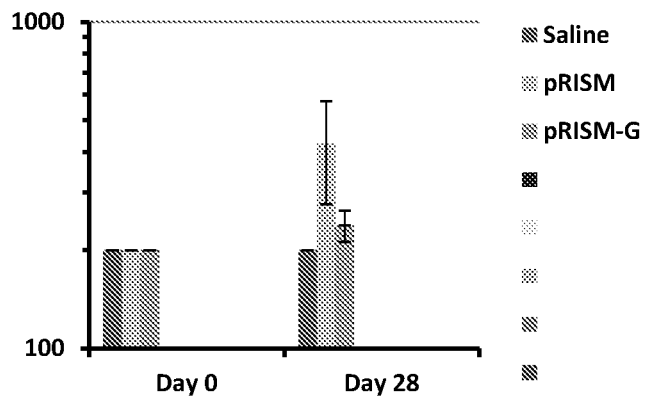
Figure 9:
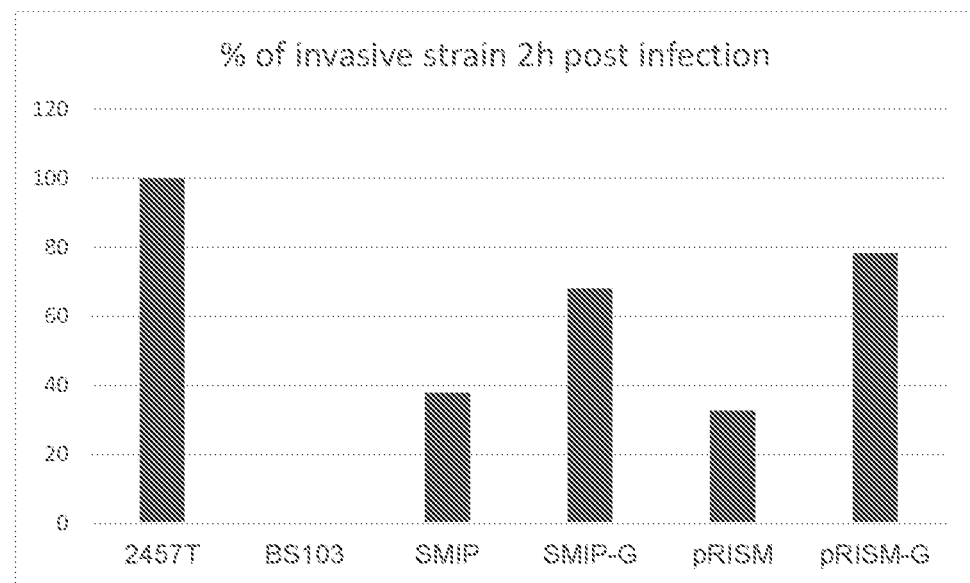
Figure 10:
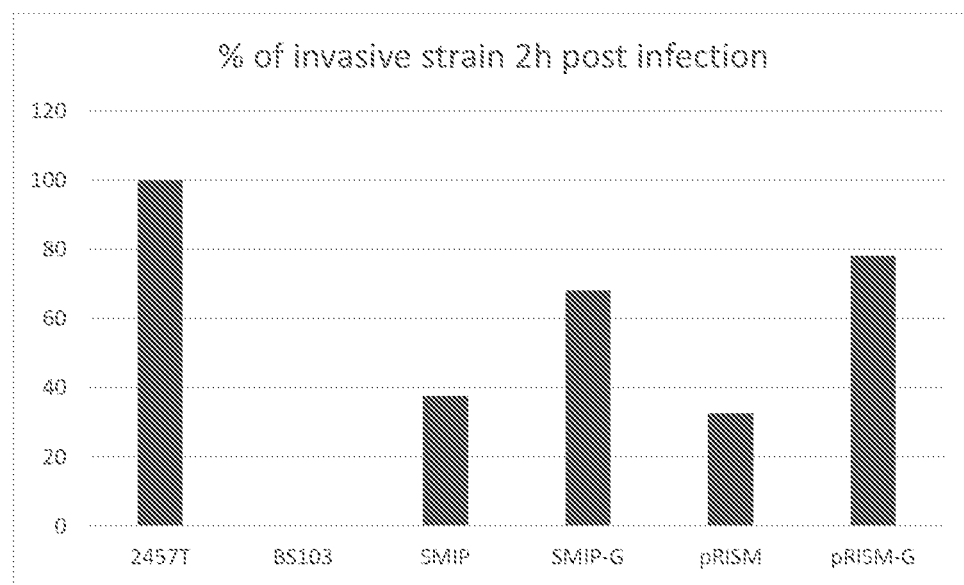

IgA and IgG to LPS and Invaplex (IVP, an aqueous extract of virulent *Shigella* containing a macromolecular complex of LPS, IpaB and IpaC) were also assayed by ELISA from serum and eyewash samples collected on Day 0, Day 28 and Day 56. Results are shown below (FIGS. 6-8).

Serum IgG to LPS: On day 28 PRISM and pRISM-G immunized guinea pig sera had a 5.6 fold and 3 fold increase in mean titer respectively compared to control sera. On day 56 there was an increase in the IgG responses. PRISM sera showed 15 fold increase and pRISM-G sera showed 7.5 fold increase in mean titer compared to control.

Serum IgG to IVP: pRISM sera showed 4.75 fold increase and pRISM-G sera showed 4 fold increase over control on day 56. On day 28 no significant increase was seen.

Serum IgA to IVP: On day 28 PRISM sera had about 2 fold increase in mean titer over control whereas pRISM-G sera IgA titers were comparable to control. On day 56 PRISM and pRISM-G sera did not show any significant difference compared to control sera.

Mucosal IgA to LPS: On day 28 PRISM and pRISM-G samples had ~25 fold increase in mean titer compared to control samples.

Mucosal IgA to IVP: pRISM and pRISM-G samples had a ~2fold increase in mean titer compared to control samples.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A recombinant *Shigella* minimal invasion plasmid construct, PRISM, comprising SEQ ID NO: 1, wherein the PRISM optionally comprises a selection gene or recombinant *Shigella* minimal invasion plasmid construct, pRISM-G, comprising SEQ ID NO: 2, wherein the pRISM-G optionally comprises a selection gene.

2. A recombinant *Shigella* minimal invasion plasmid construct of claim 1, wherein the PRISM or pRISM-G comprises a *Shigella* cell-entry region from a *Shigella flexneri* bacterium.

3. The recombinant *Shigella* minimal invasion plasmid construct of claim 1, wherein the selection gene is an antibiotic resistance gene.

4. A *Shigella* or *E. coli* bacterium comprising a recombinant *Shigella* minimal invasion plasmid construct, PRISM, comprising SEQ ID NO: 1, or a recombinant *Shigella* minimal invasion plasmid construct, pRISM-G, comprising SEQ ID NO: 2.

5. A composition comprising the *Shigella* or *E. coli* bacterium of claim 4 and a pharmaceutically acceptable excipient.

6. The composition of claim 5, further comprising an adjuvant.

7. A method of inducing an immune response in a subject, the method comprising administering a composition comprising a recombinant *Shigella* minimal invasion plasmid construct, pRISM, comprising SEQ ID NO: 1, or a recombinant *Shigella* minimal invasion plasmid construct, pRISM-G, comprising SEQ ID NO: 2, or a *Shigella* or *E. coli* bacterium comprising either pRISM or pRISM-G, to the subject in an amount sufficient to induce the immune response.

8. The method of claim 7, wherein the immune response is against a pathogen.

9. The method of claim 8, wherein the pathogen is a virus, bacterium, fungus or parasite.

10. The method of claim 9, wherein the pathogen is *Shigella* or *E. coli.*

11. The method of claim 7, wherein the pRISM or pRISM-G comprise a nucleic acid encoding a bacterial, viral, fungal, parasitic, or mammalian protein of interest, or an immunogenic portion thereof.

12. The *Shigella* or *E. coli* bacterium of claim 4, wherein the pRISM or pRISM-G comprise a nucleic acid encoding a bacterial, viral, fungal, parasitic, or mammalian protein of interest, or an immunogenic portion thereof.

* * * * *